(12) United States Patent
Campagna

(10) Patent No.: US 12,245,879 B2
(45) Date of Patent: Mar. 11, 2025

(54) PATIENT PLATFORM, WITH COORDINATION VIA BILATERAL STRAIGHT-LINE MECHANISM

(71) Applicant: Michael Campagna, Naperville, IL (US)

(72) Inventor: Michael Campagna, Naperville, IL (US)

( * ) Notice: Subject to any disclaimer, the term of this patent is extended or adjusted under 35 U.S.C. 154(b) by 751 days.

(21) Appl. No.: 17/347,545

(22) Filed: Jun. 14, 2021

(65) Prior Publication Data
US 2022/0378385 A1 Dec. 1, 2022

Related U.S. Application Data

(60) Provisional application No. 63/062,846, filed on Aug. 7, 2020, provisional application No. 63/038,743, filed on Jun. 12, 2020.

(51) Int. Cl.

| | |
|---|---|
| *A61B 6/04* | (2006.01) |
| *A61B 5/00* | (2006.01) |
| *A61G 7/012* | (2006.01) |
| *A61G 7/018* | (2006.01) |
| *A61G 13/02* | (2006.01) |
| *A61G 13/06* | (2006.01) |
| *F16H 21/18* | (2006.01) |
| *F16H 21/36* | (2006.01) |

(52) U.S. Cl.
CPC ............ *A61B 6/0407* (2013.01); *A61B 5/704* (2013.01); *A61G 7/012* (2013.01); *A61G 7/018* (2013.01); *A61G 13/02* (2013.01); *A61G 13/06* (2013.01); *F16H 21/36* (2013.01); *A61B 6/04* (2013.01); *F16H 21/18* (2013.01)

(58) Field of Classification Search
CPC ......... A61B 6/0407; A61B 6/04; A61B 5/704; F16H 21/36; F16H 21/18; F16H 21/16; A61G 7/005; A61G 7/012; A61G 7/015; A61G 7/018; A61G 13/02; A61G 13/04; A61G 13/06; A61G 13/08
USPC ....... 5/601, 600, 610, 611; 378/20, 208, 209
See application file for complete search history.

(56) References Cited

U.S. PATENT DOCUMENTS

| | | | | |
|---|---|---|---|---|
| 4,528,860 | A * | 7/1985 | Barr .................. | B65G 25/04 74/52 |
| 8,381,330 | B2 * | 2/2013 | Roussy ............... | A61G 7/0528 296/20 |
| 9,101,516 | B2 * | 8/2015 | Roussy ............... | A61G 1/017 |
| 11,098,791 | B2 * | 8/2021 | Rajendran ........... | F16H 21/36 |
| 11,224,549 | B2 * | 1/2022 | Trimble ............... | A61G 7/018 |
| 11,339,859 | B2 * | 5/2022 | Rajendran ........... | F16H 29/00 |
| 11,771,607 | B2 * | 10/2023 | Trimble ............... | A61G 7/1013 5/613 |
| 2011/0113556 | A1 * | 5/2011 | Roussy ............... | A61G 1/0237 5/611 |
| 2013/0180051 | A1 * | 7/2013 | Roussy ............... | A61G 7/012 5/611 |
| 2018/0209523 | A1 * | 7/2018 | Rajendran ........... | F16H 29/20 |
| 2019/0003564 | A1 * | 1/2019 | Rajendran ........... | F16H 21/36 |

(Continued)

FOREIGN PATENT DOCUMENTS

| | | | | |
|---|---|---|---|---|
| CA | 2518162 | C * | 2/2014 | ............ A61G 1/017 |
| GB | 2423245 | A * | 8/2006 | ............ A61G 1/017 |

(Continued)

*Primary Examiner* — Robert G Santos

(57) ABSTRACT

A bilateral straight line mechanism that is part of a patient support mechanism.

17 Claims, 55 Drawing Sheets

(56) References Cited

U.S. PATENT DOCUMENTS

| | | | |
|---|---|---|---|
| 2019/0192365 A1* | 6/2019 | Trimble | A61G 1/04 |
| 2019/0316662 A1* | 10/2019 | Rajendran | F16H 29/00 |
| 2022/0096298 A1* | 3/2022 | Trimble | A61G 7/1013 |
| 2022/0378385 A1* | 12/2022 | Campagna | A61B 6/0407 |
| 2023/0404826 A1* | 12/2023 | Trimble | A61G 7/1013 |

FOREIGN PATENT DOCUMENTS

| | | | |
|---|---|---|---|
| GB | 2427131 A * | 12/2006 | A61G 1/017 |
| WO | WO-2004080363 A2 * | 9/2004 | A61G 1/017 |
| WO | WO-2024115943 A1 * | 6/2024 | |

* cited by examiner

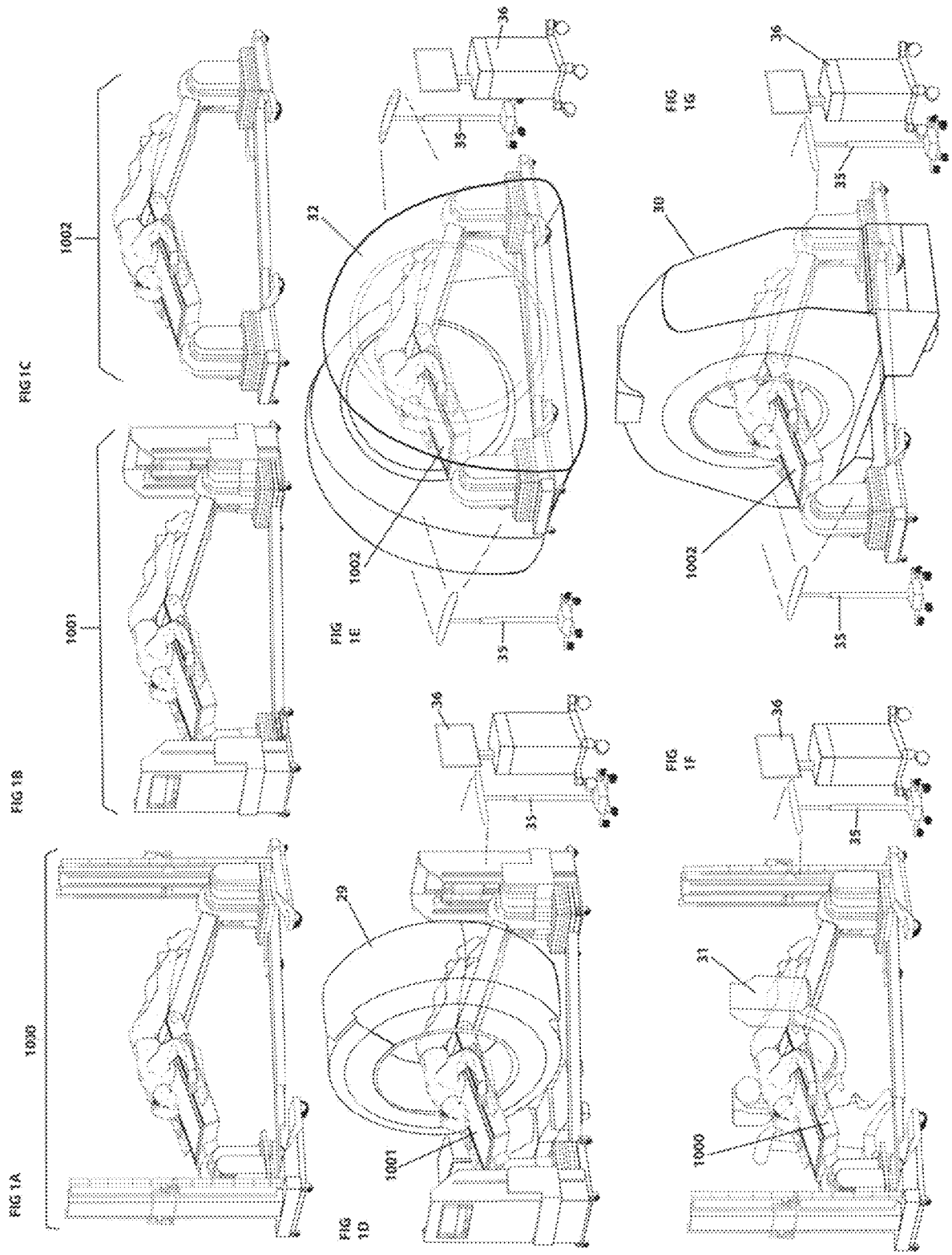

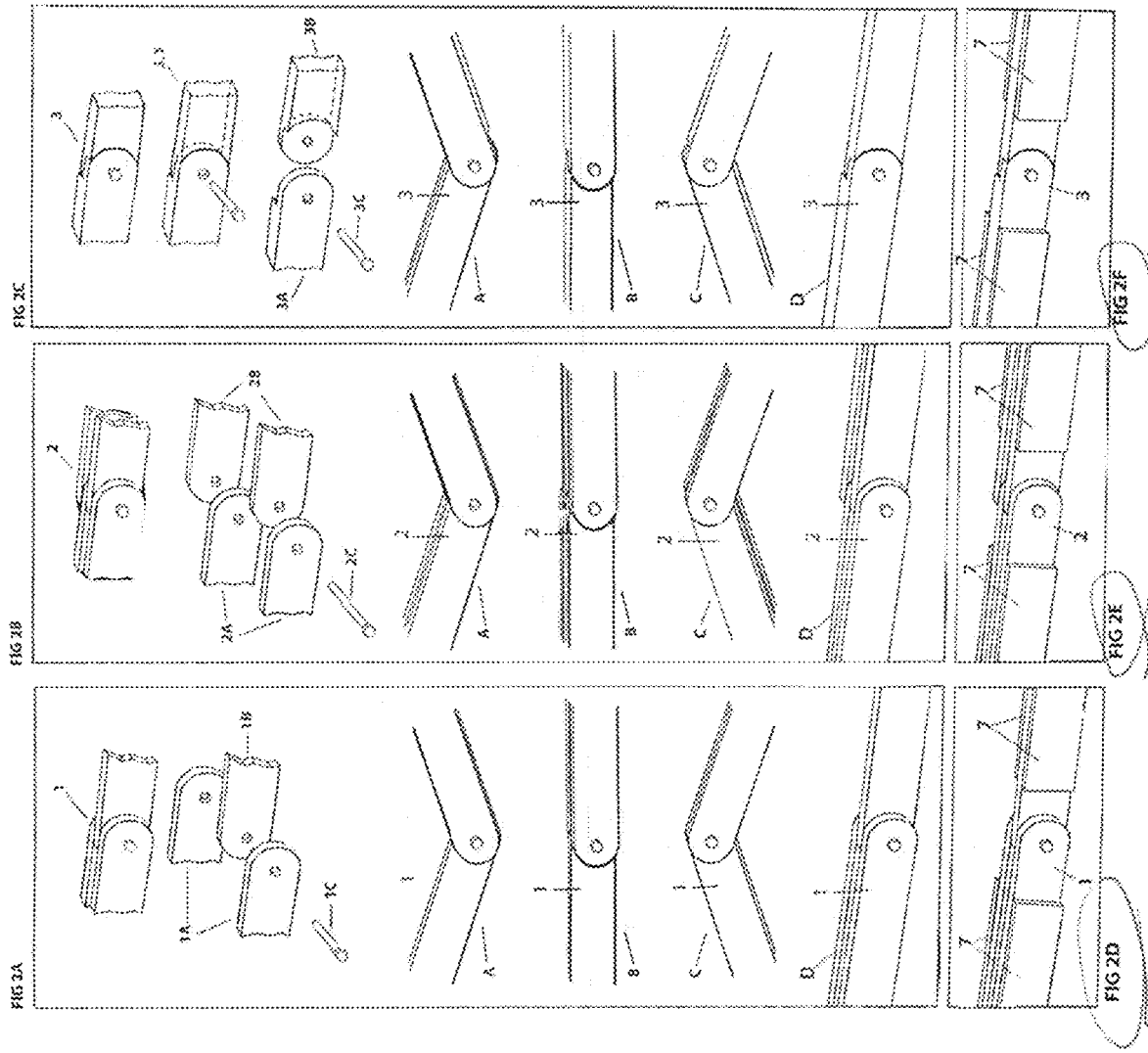

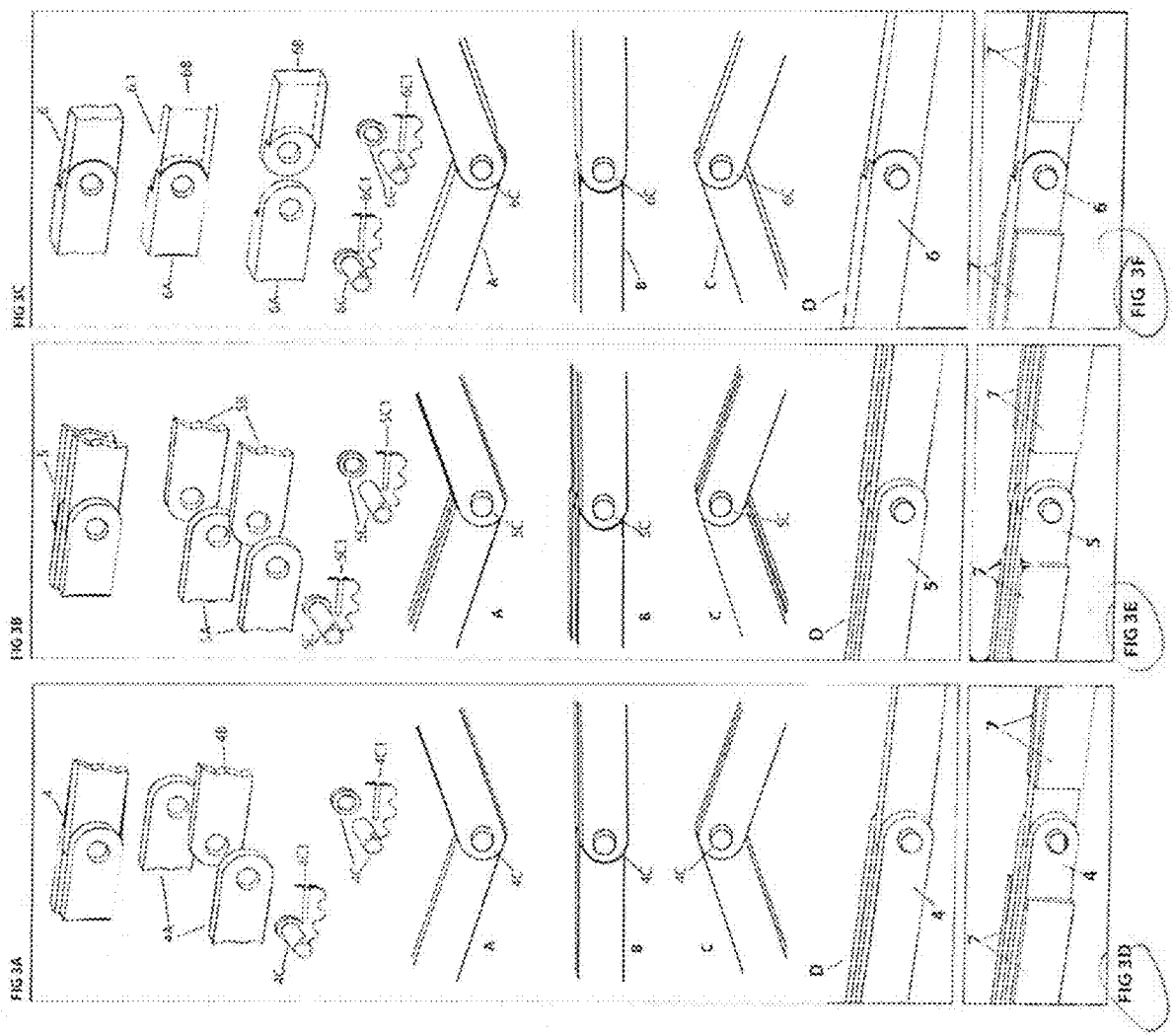

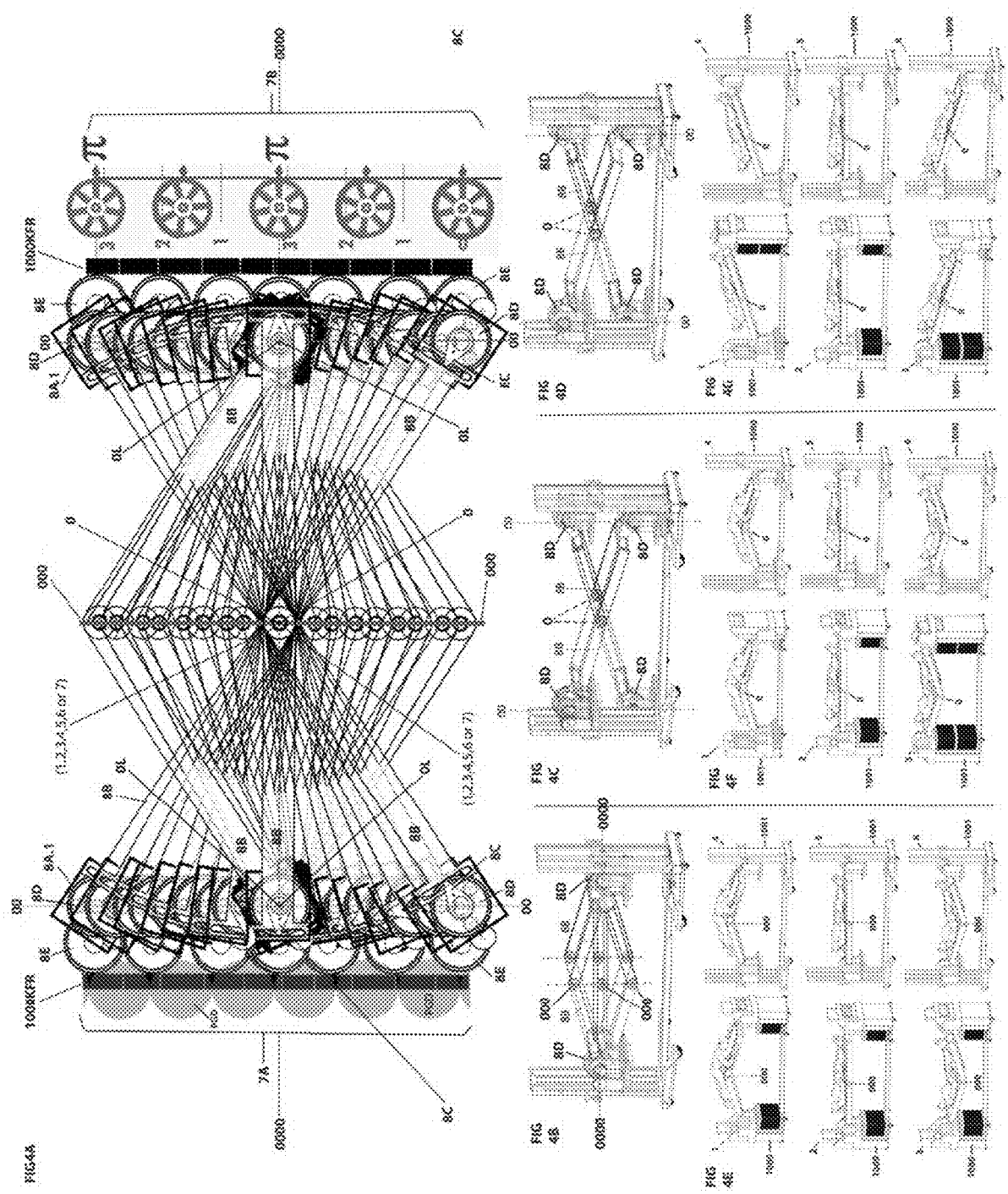

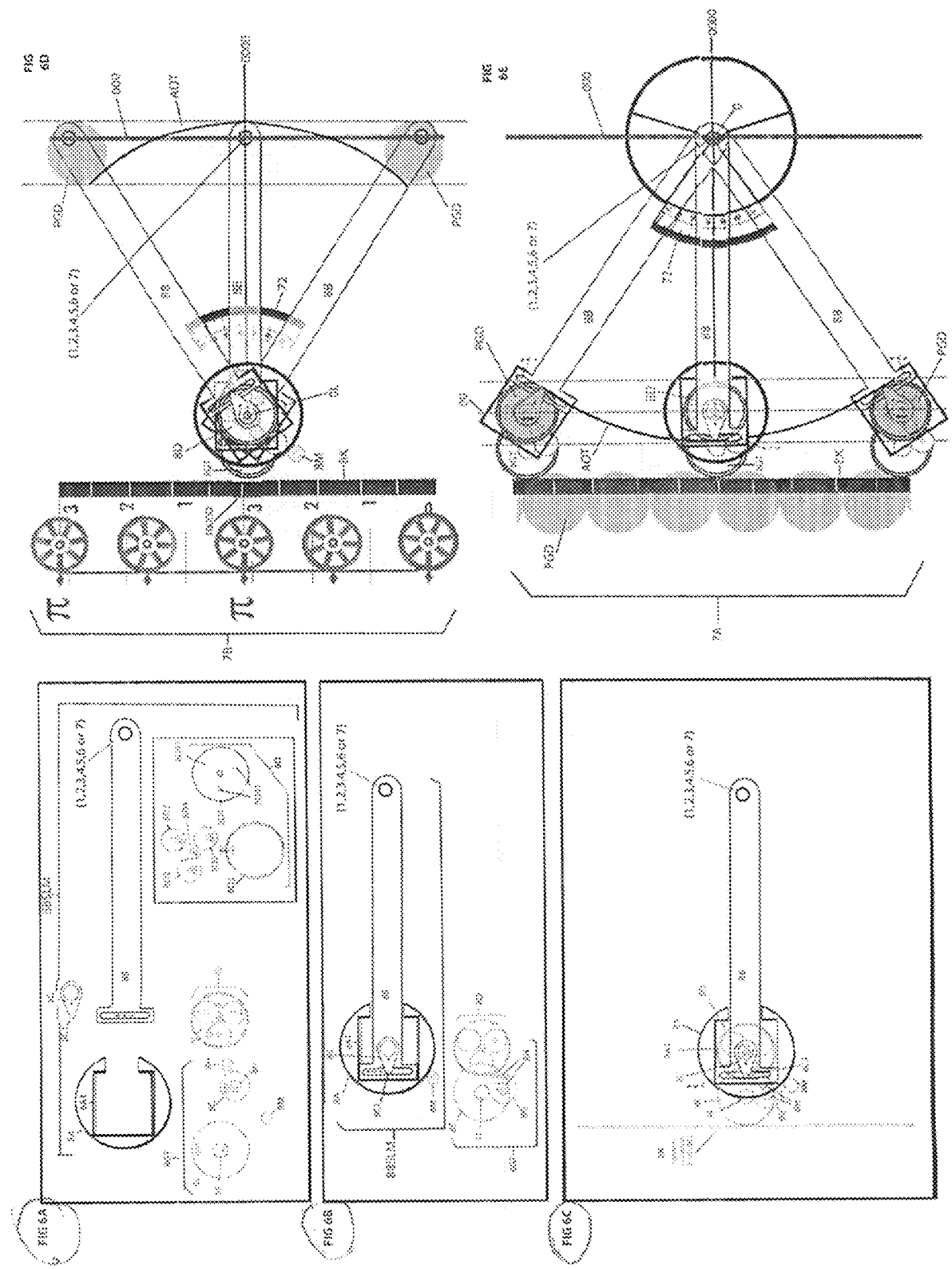

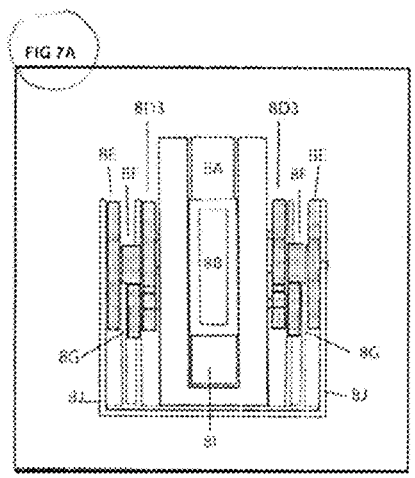
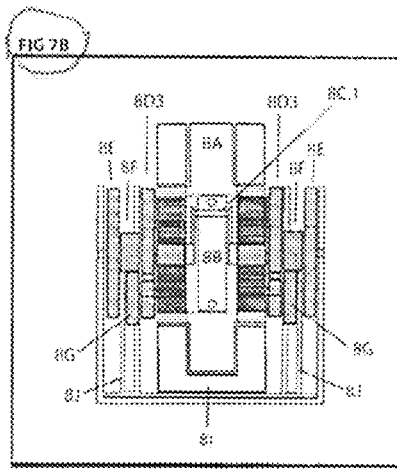
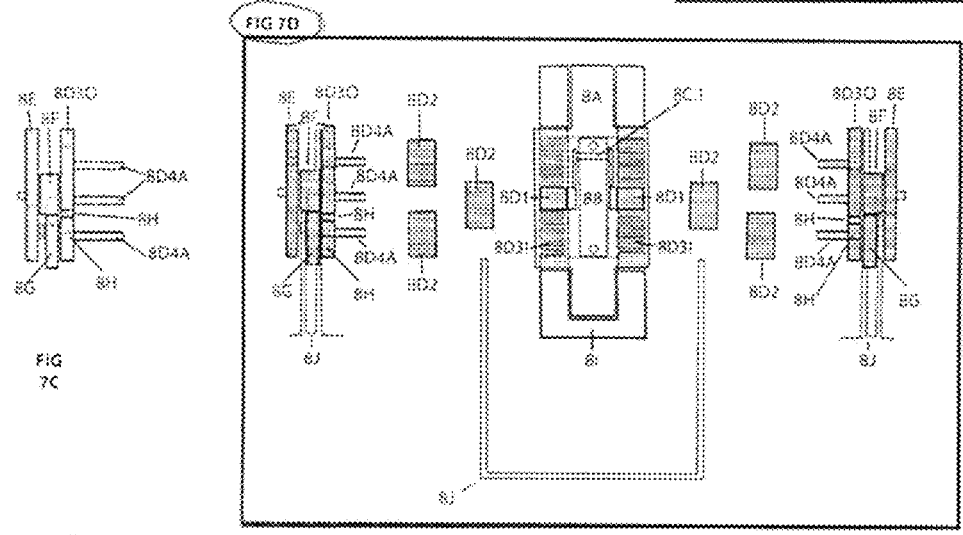
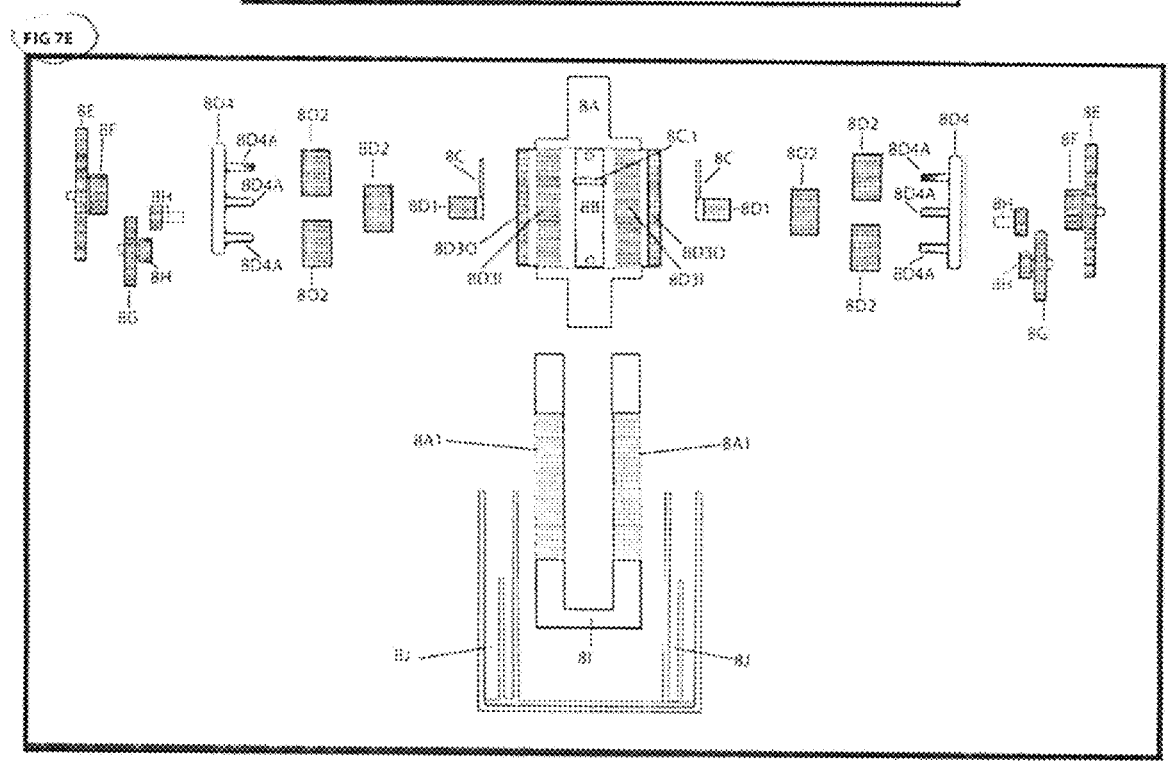

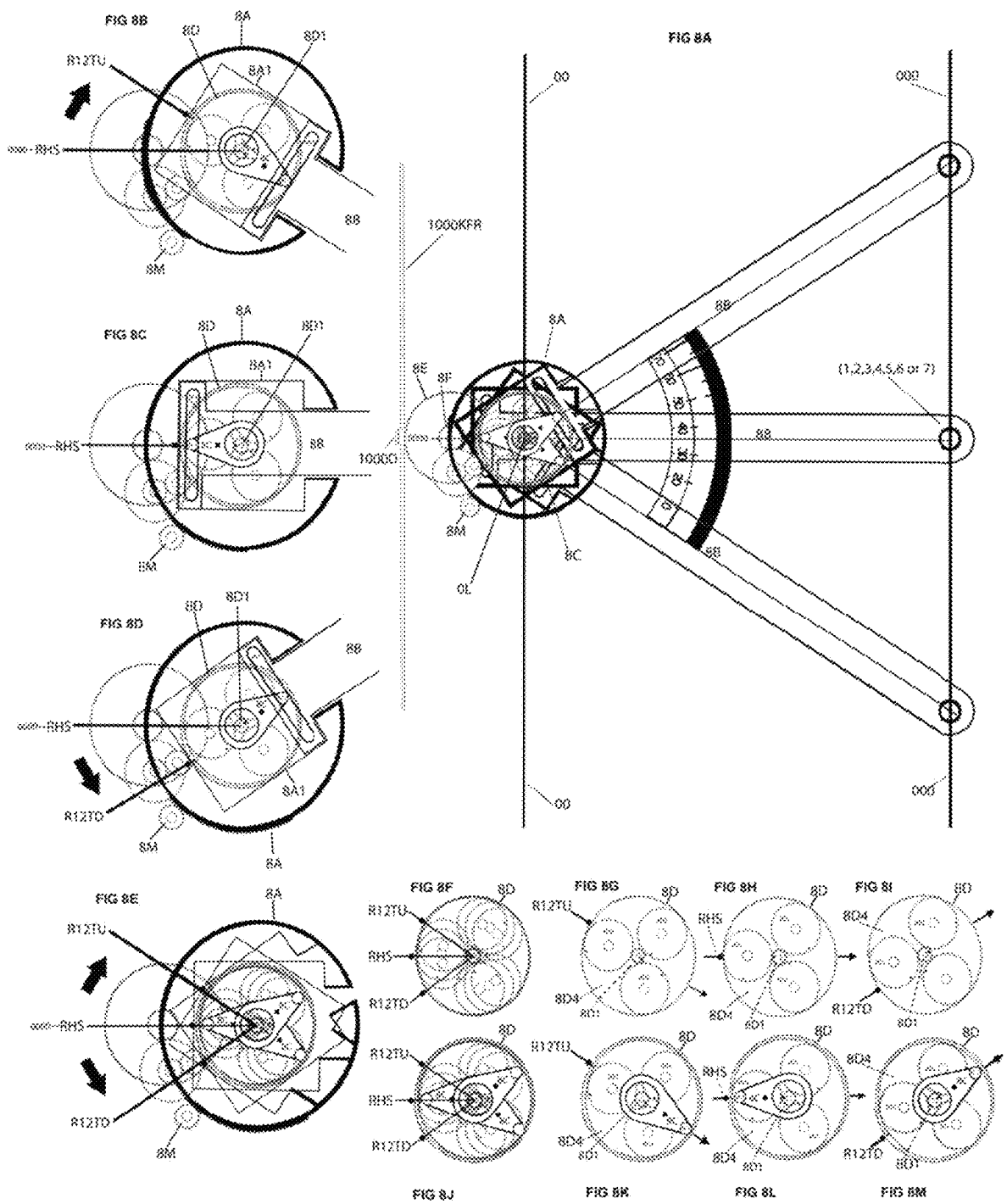

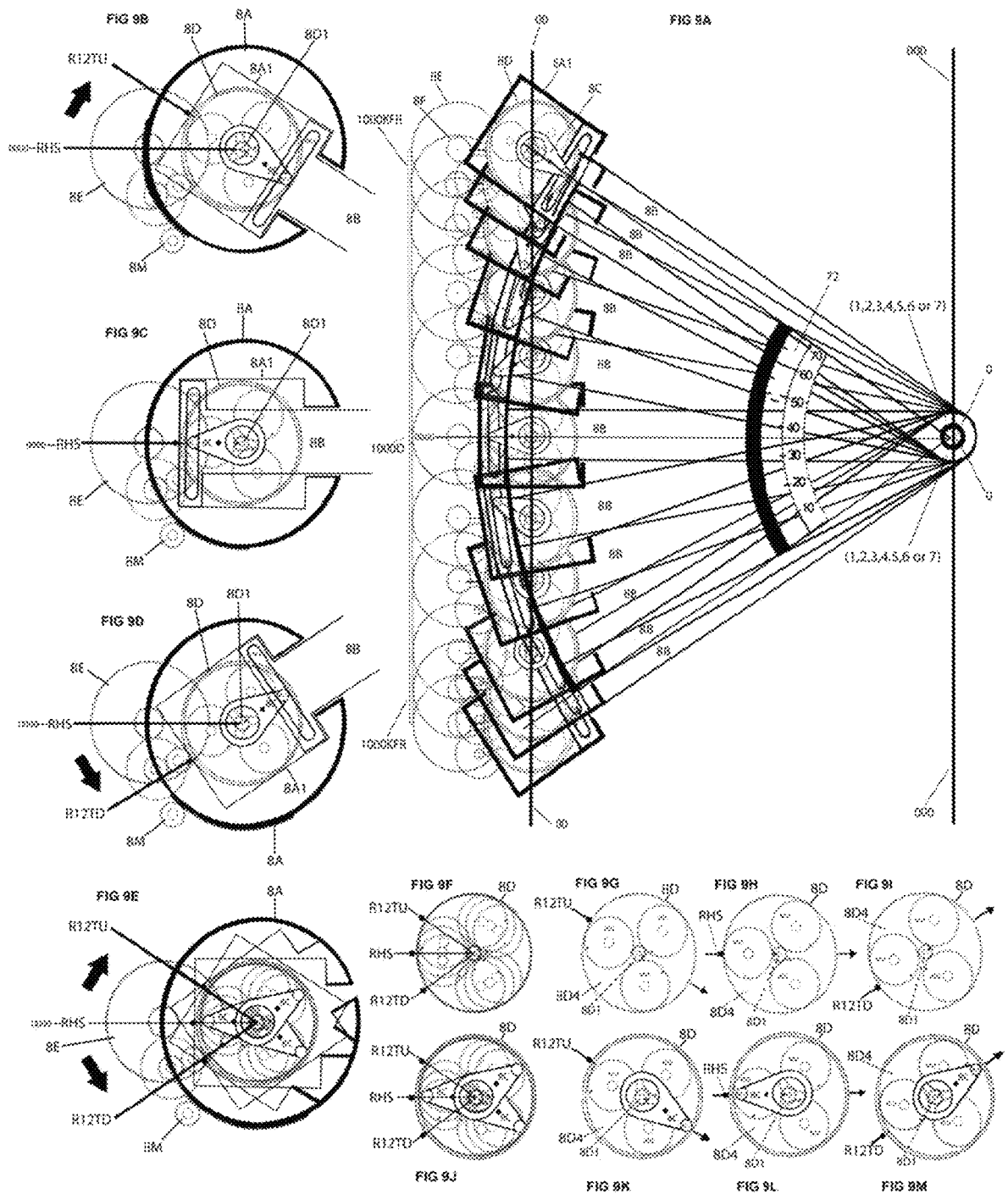

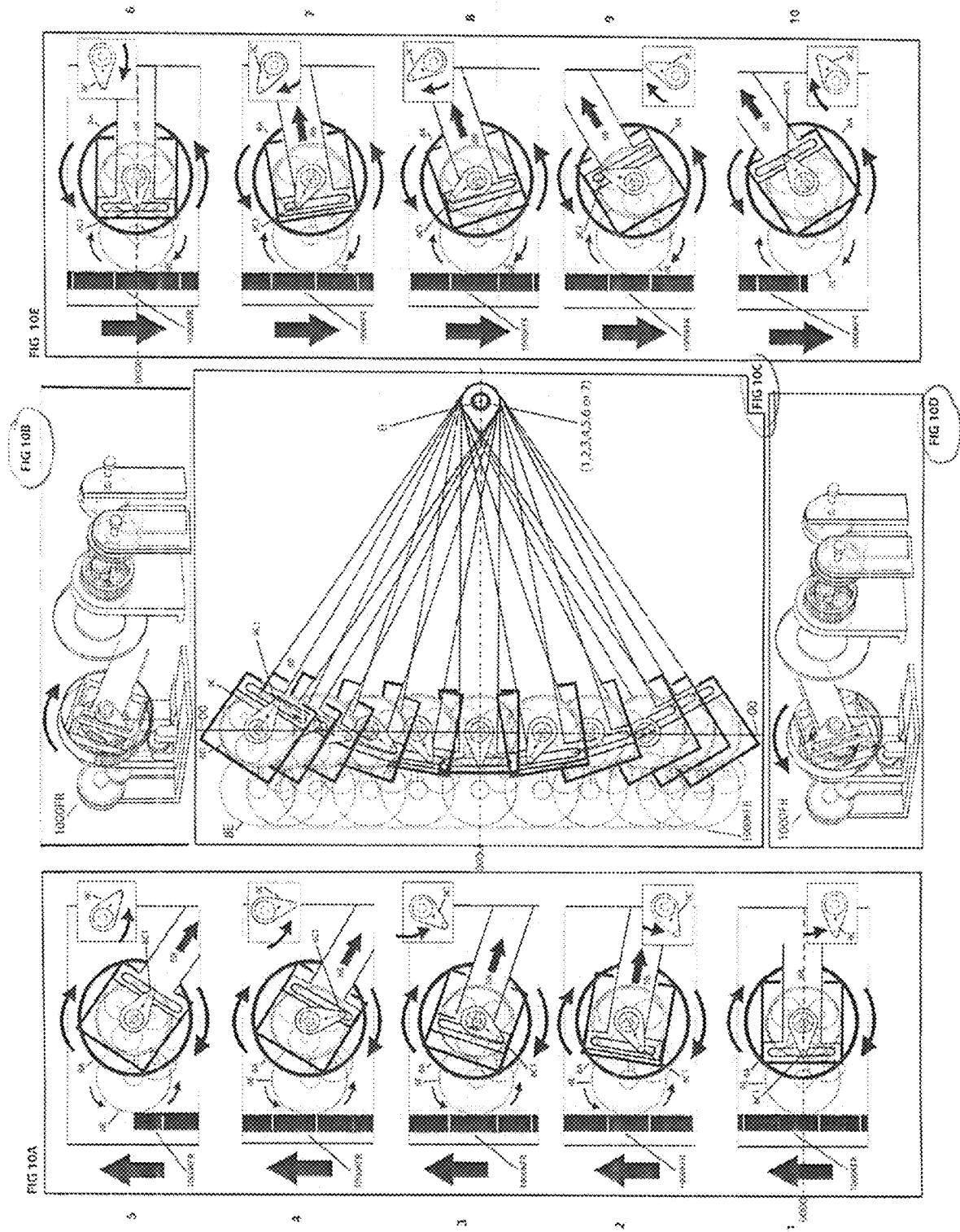

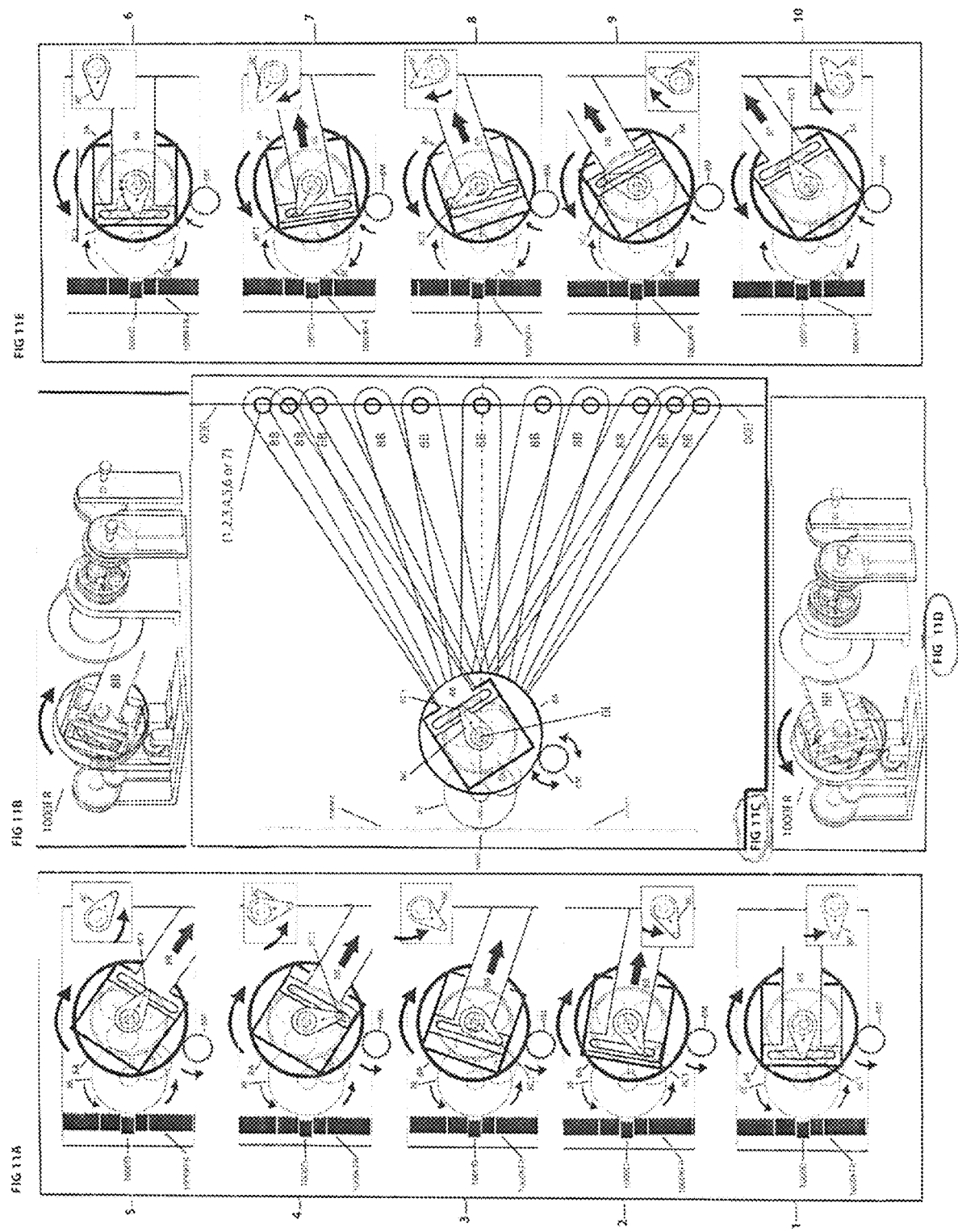

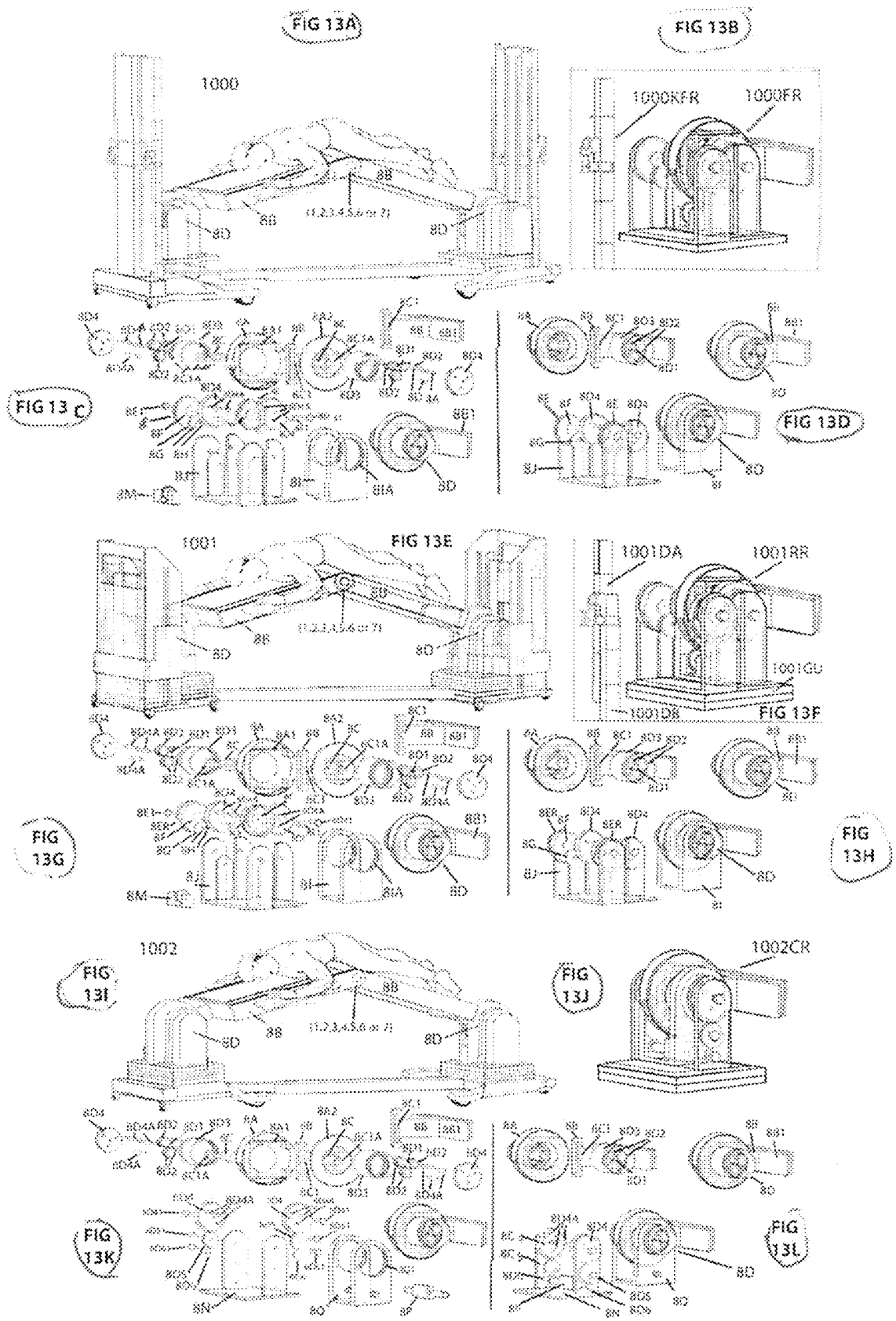

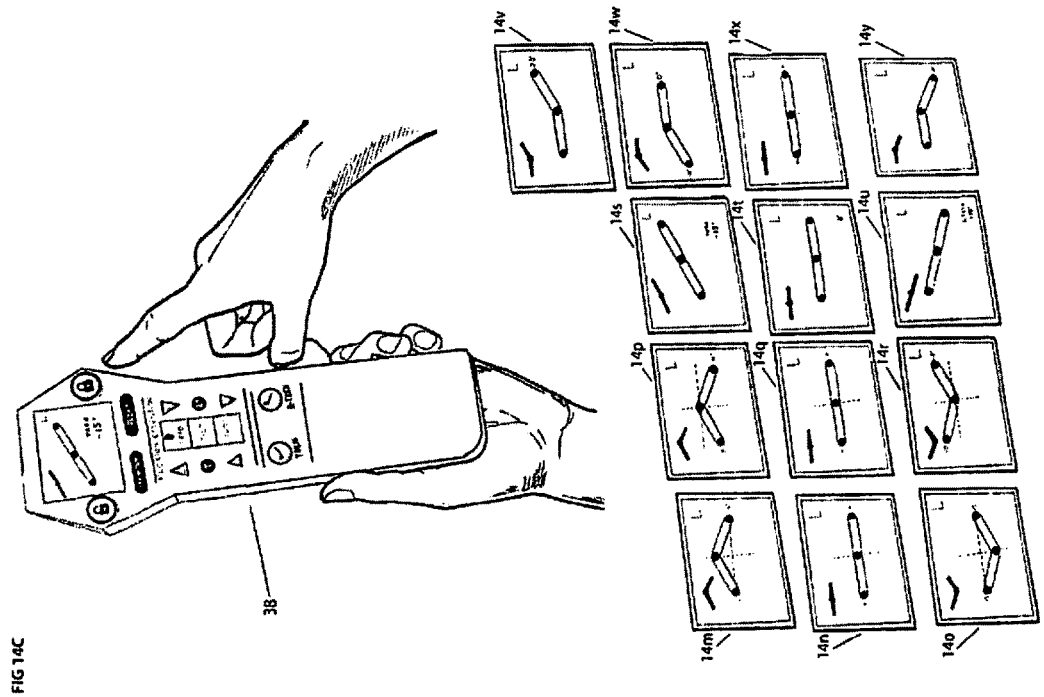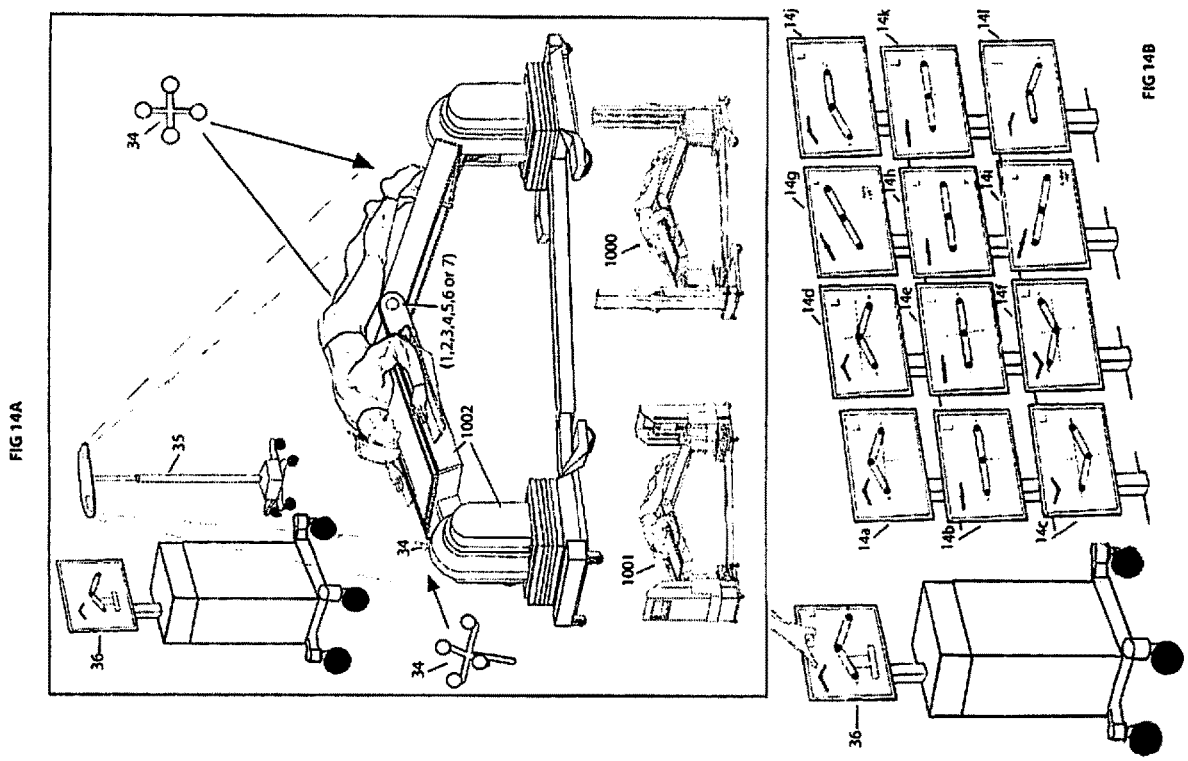

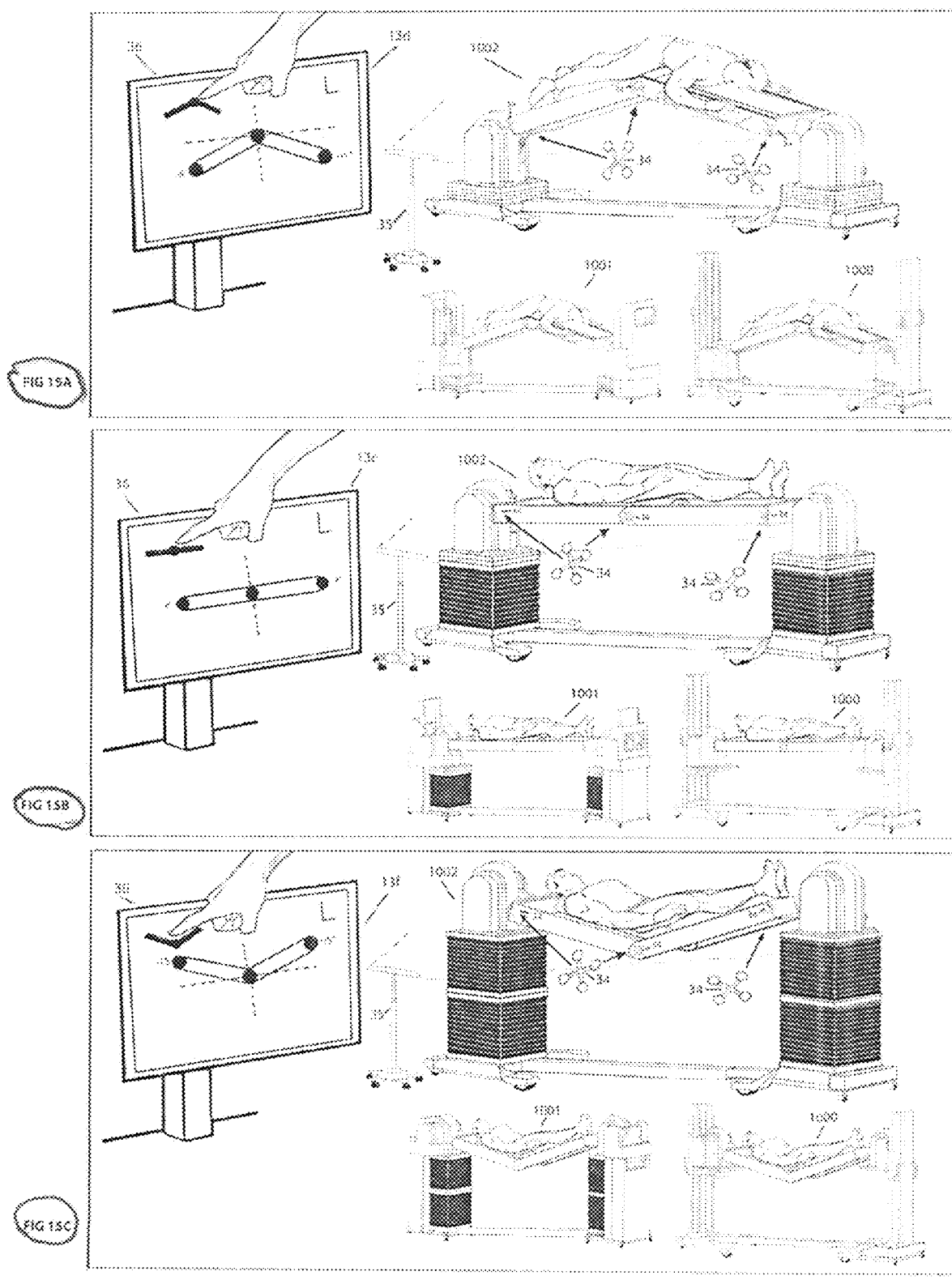

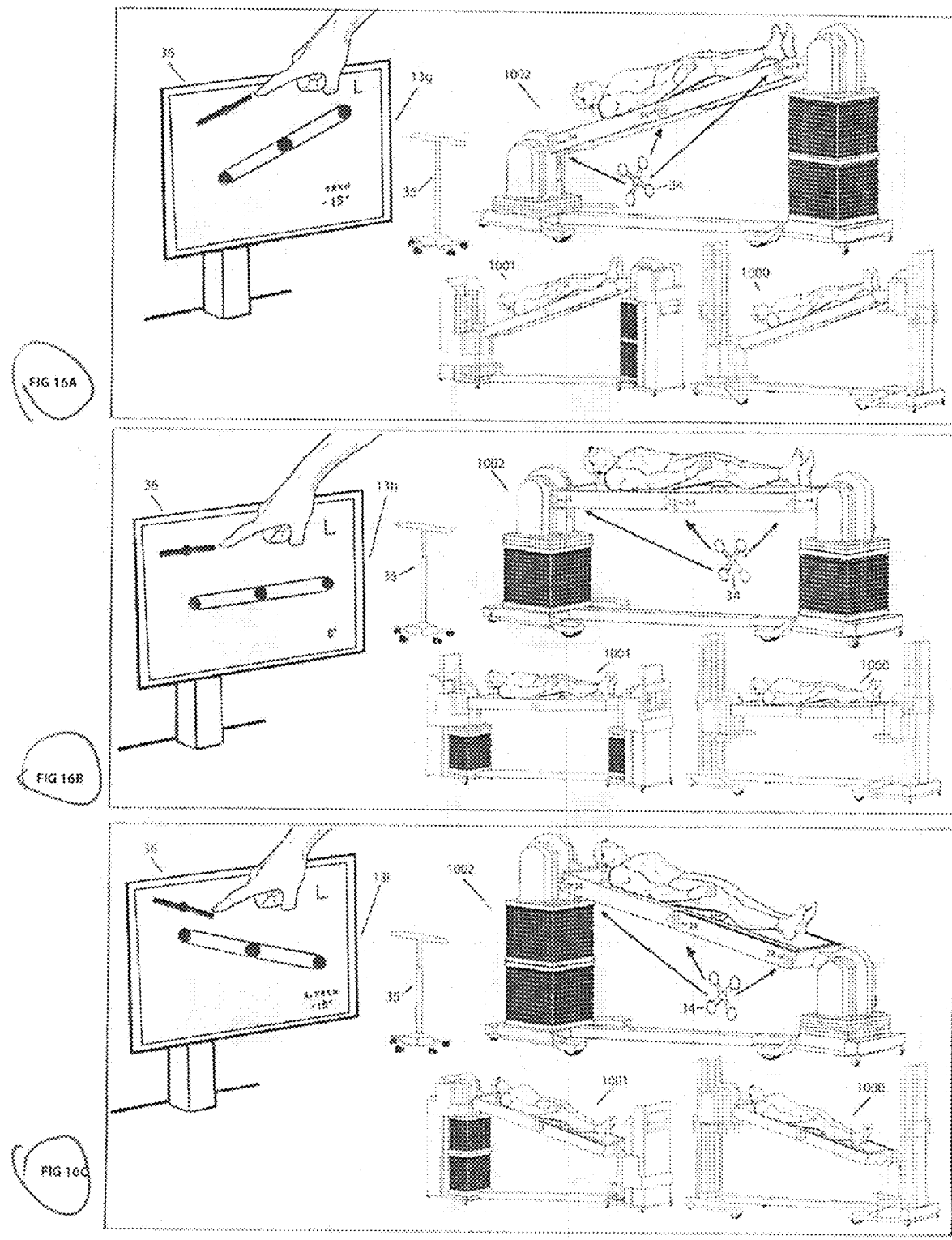

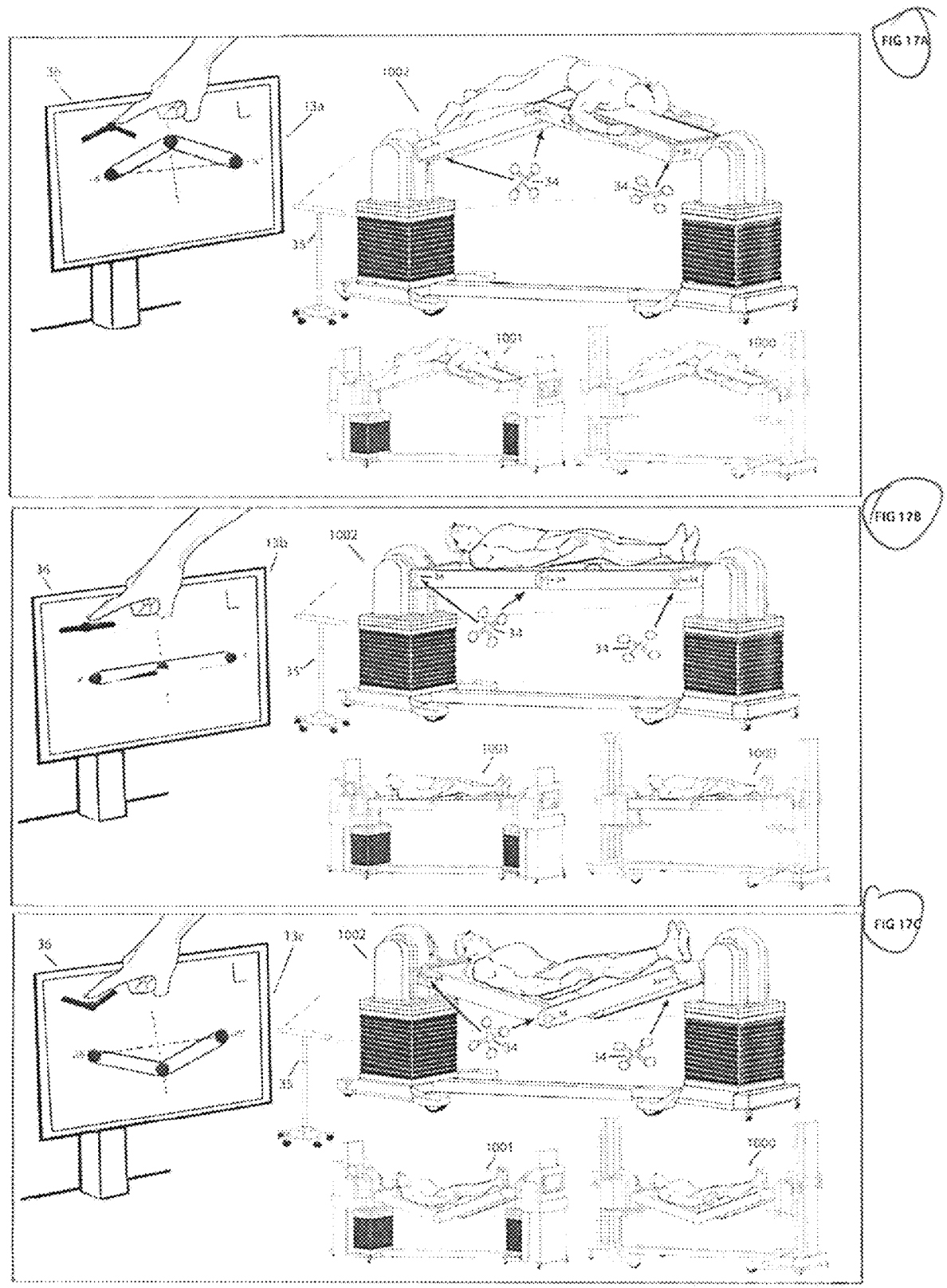

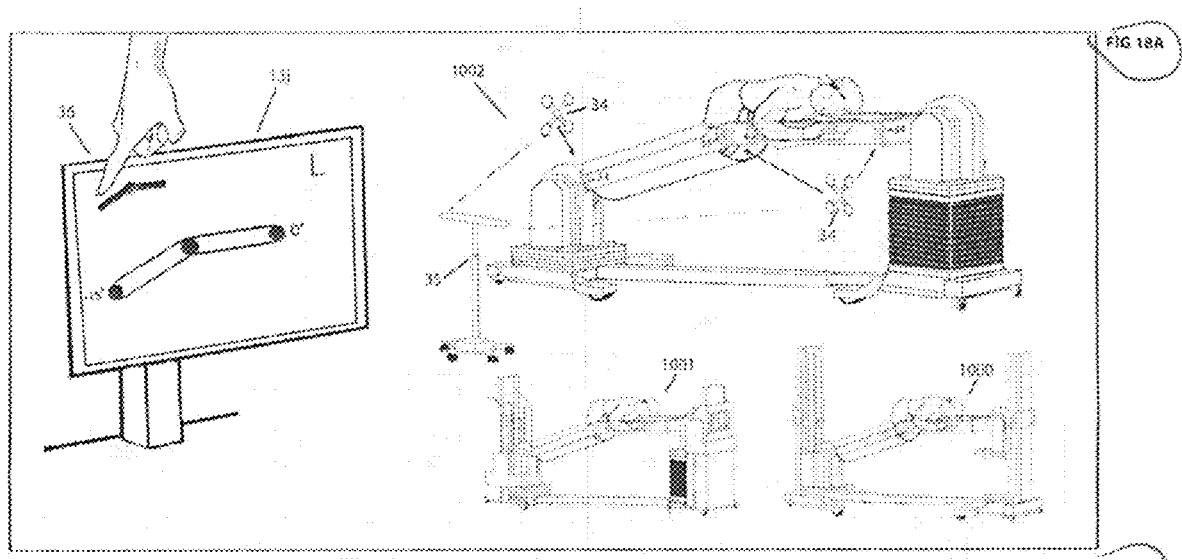
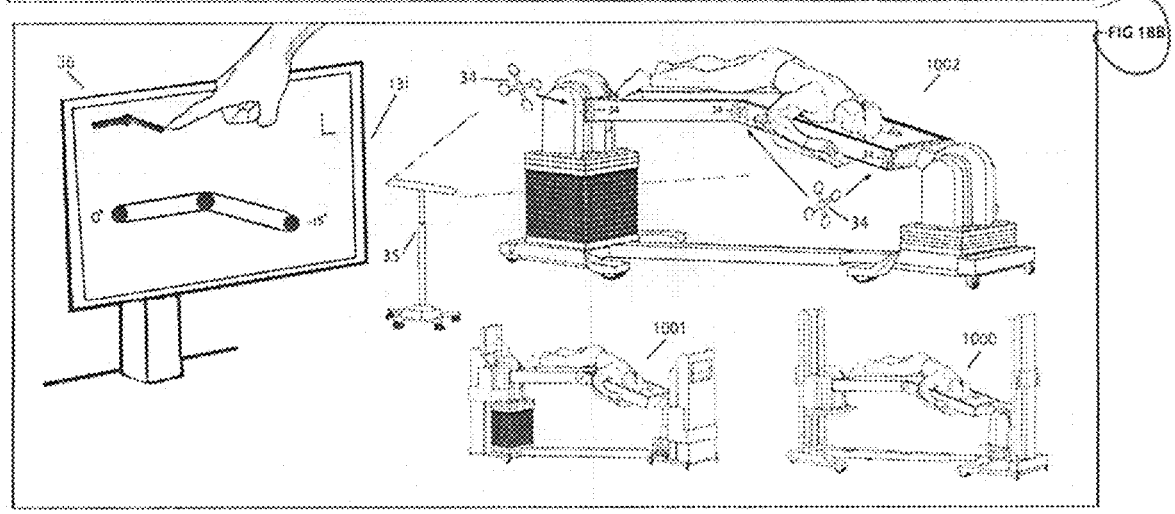

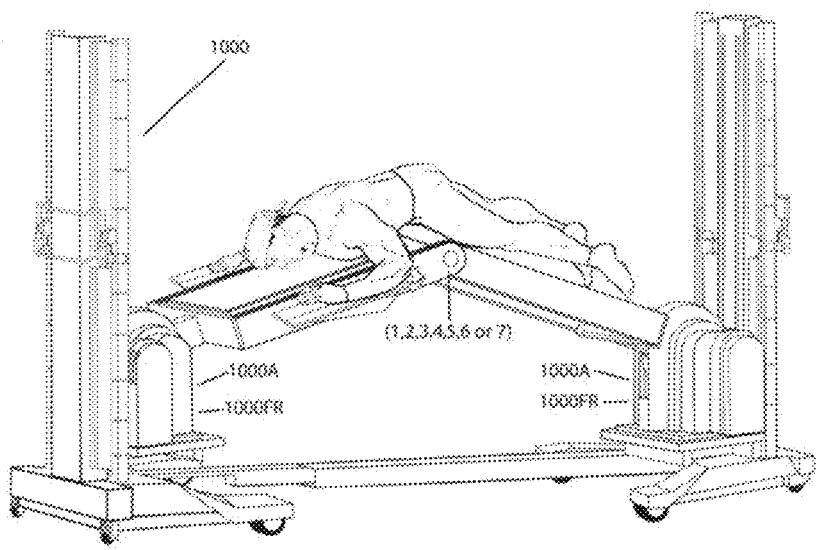
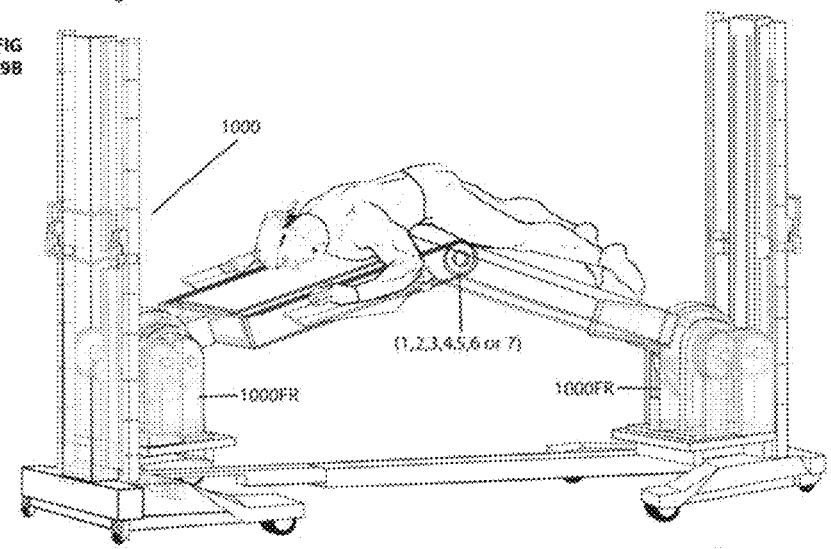
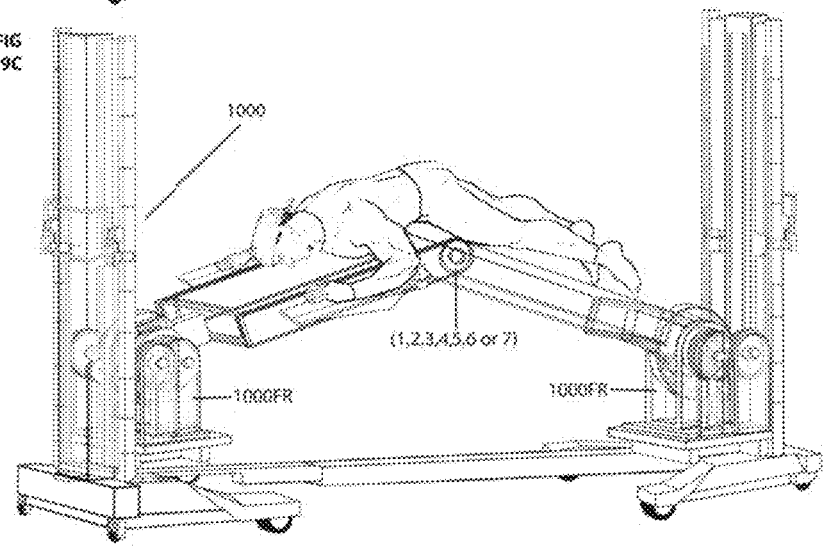

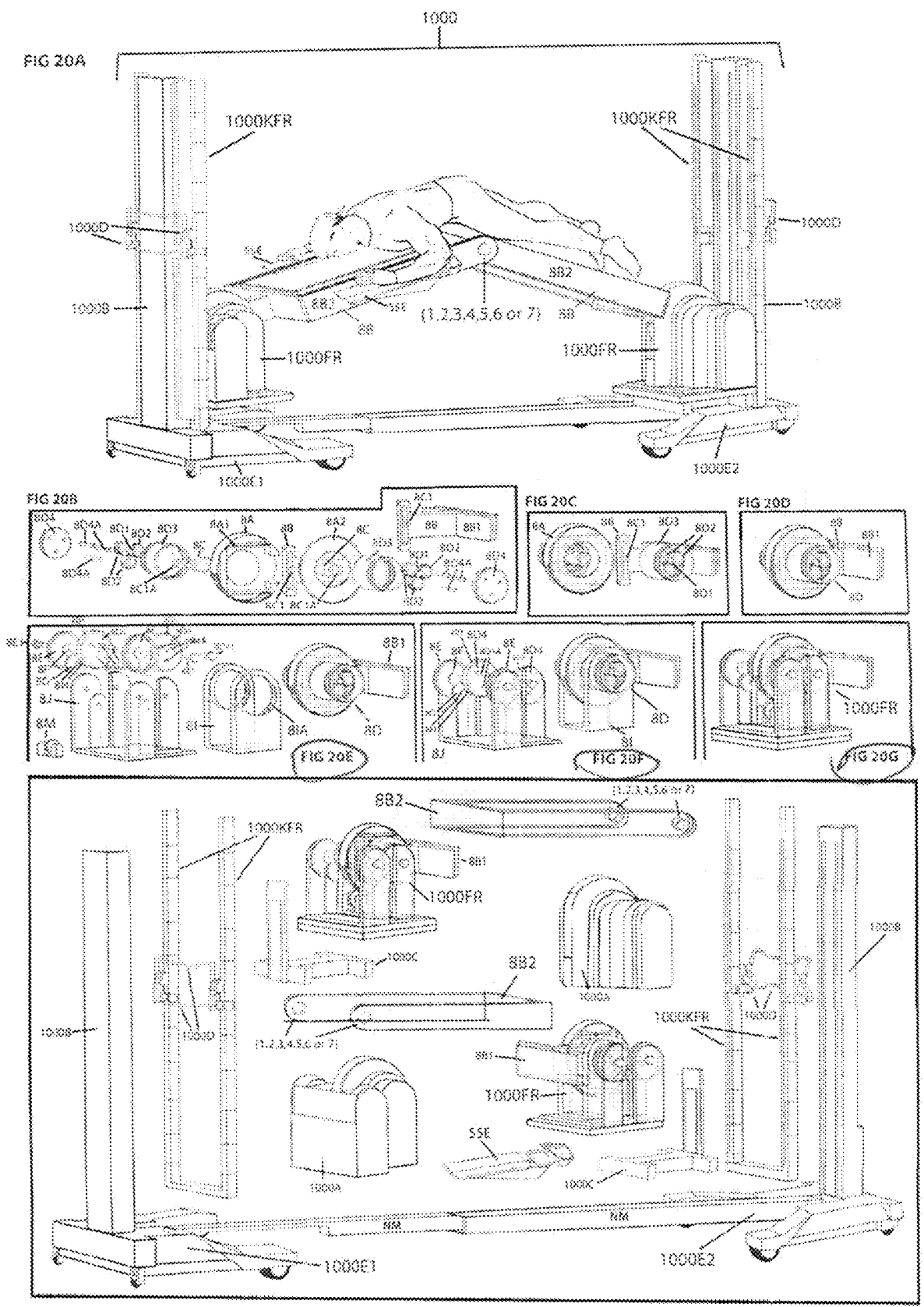

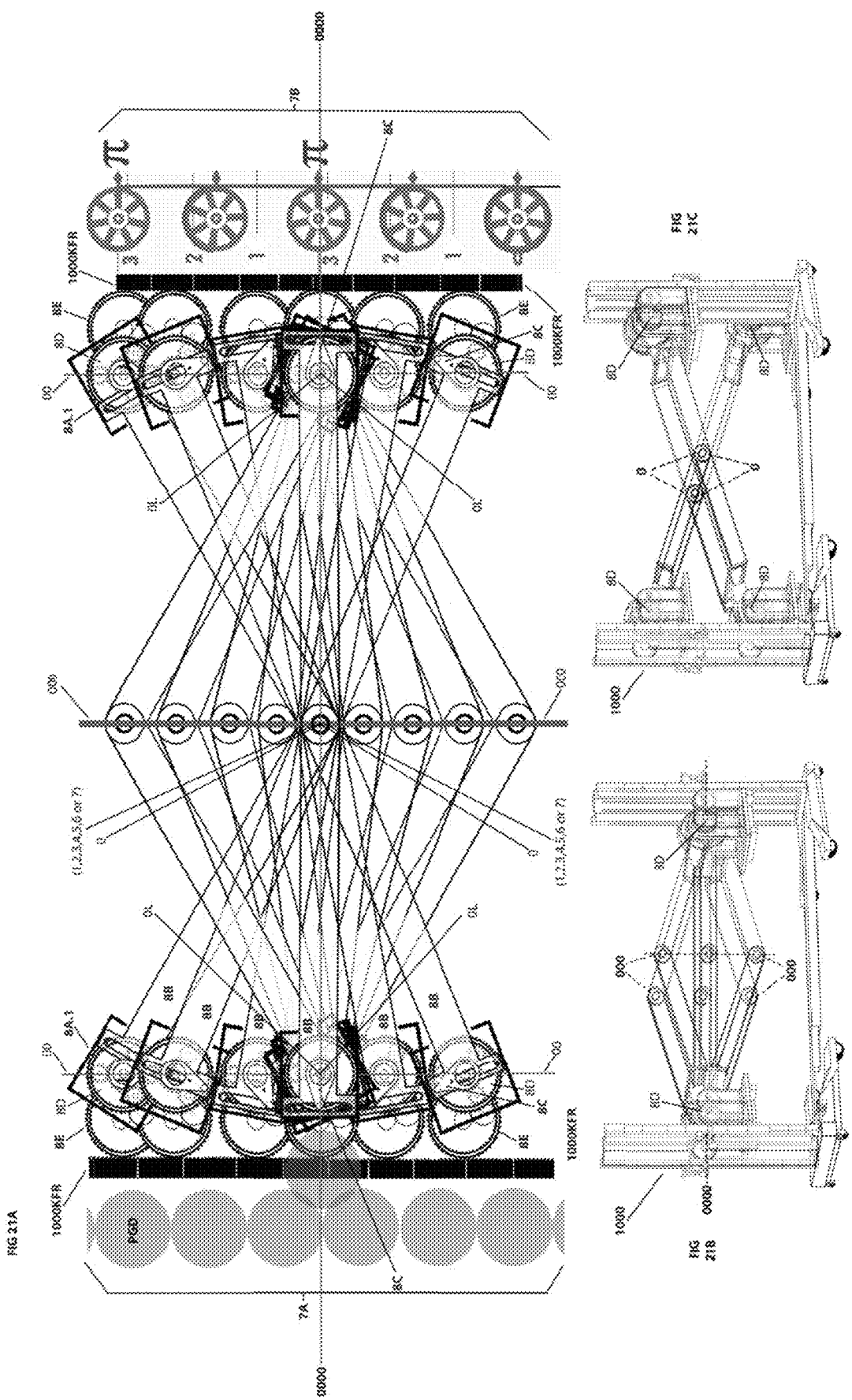

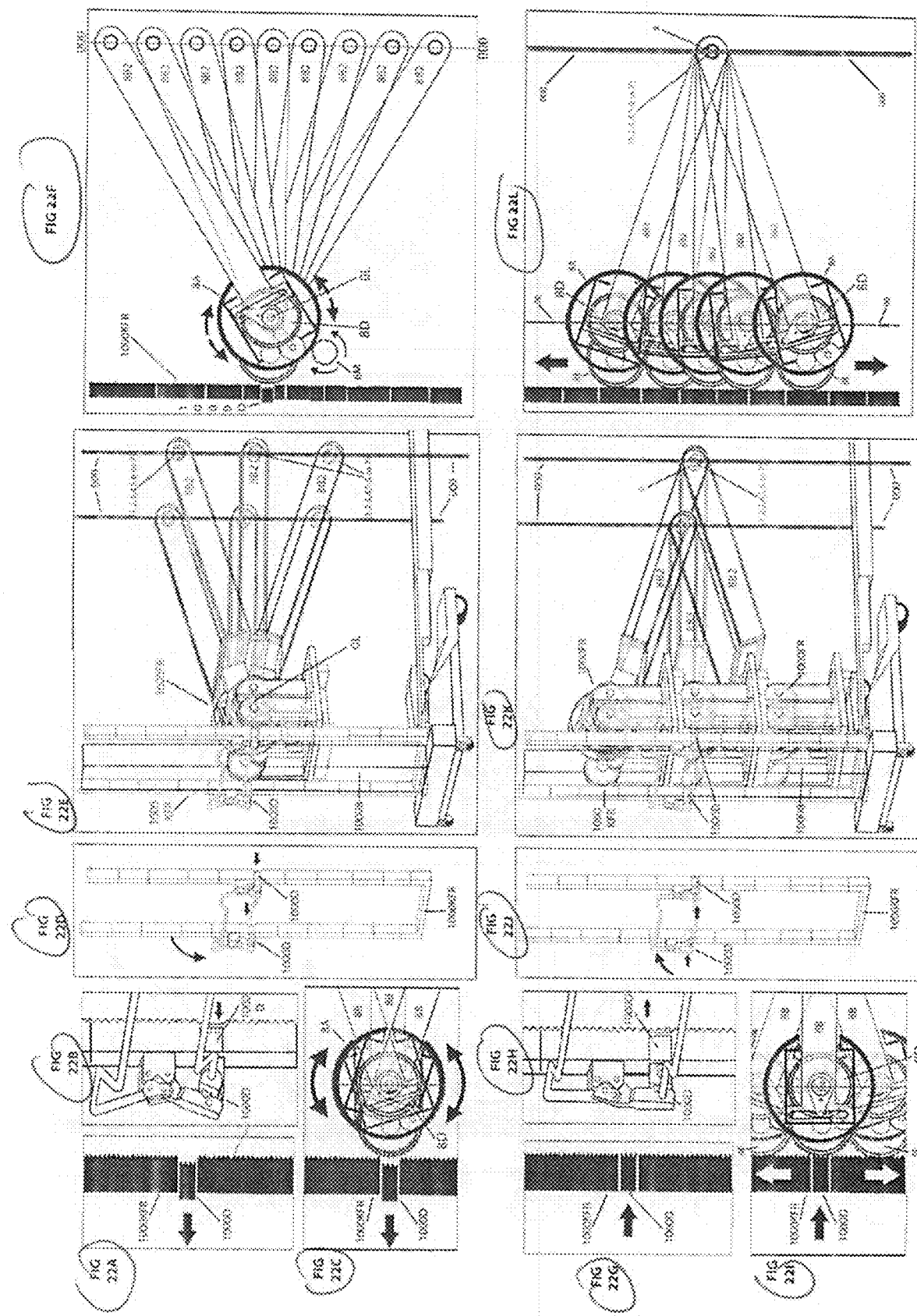

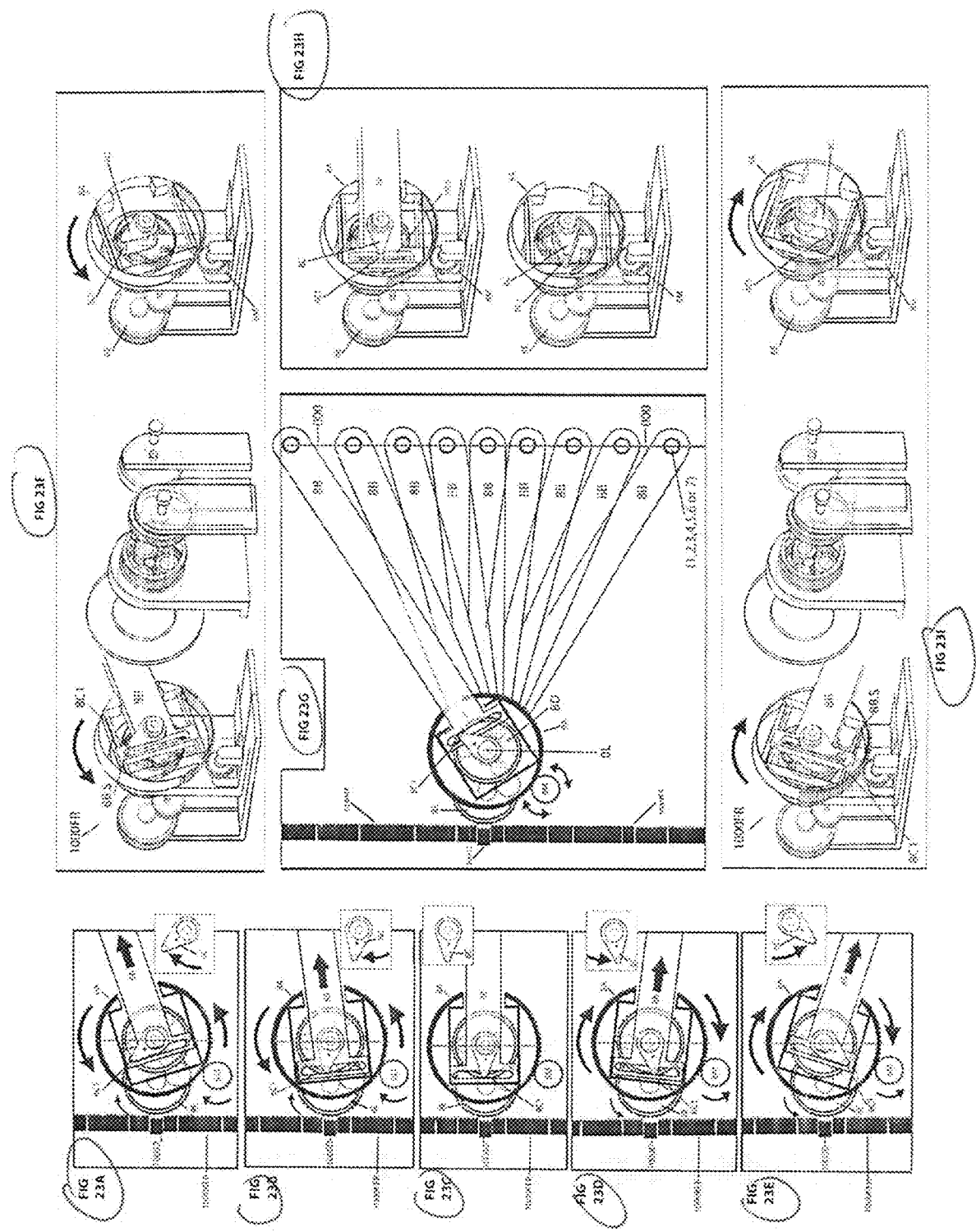

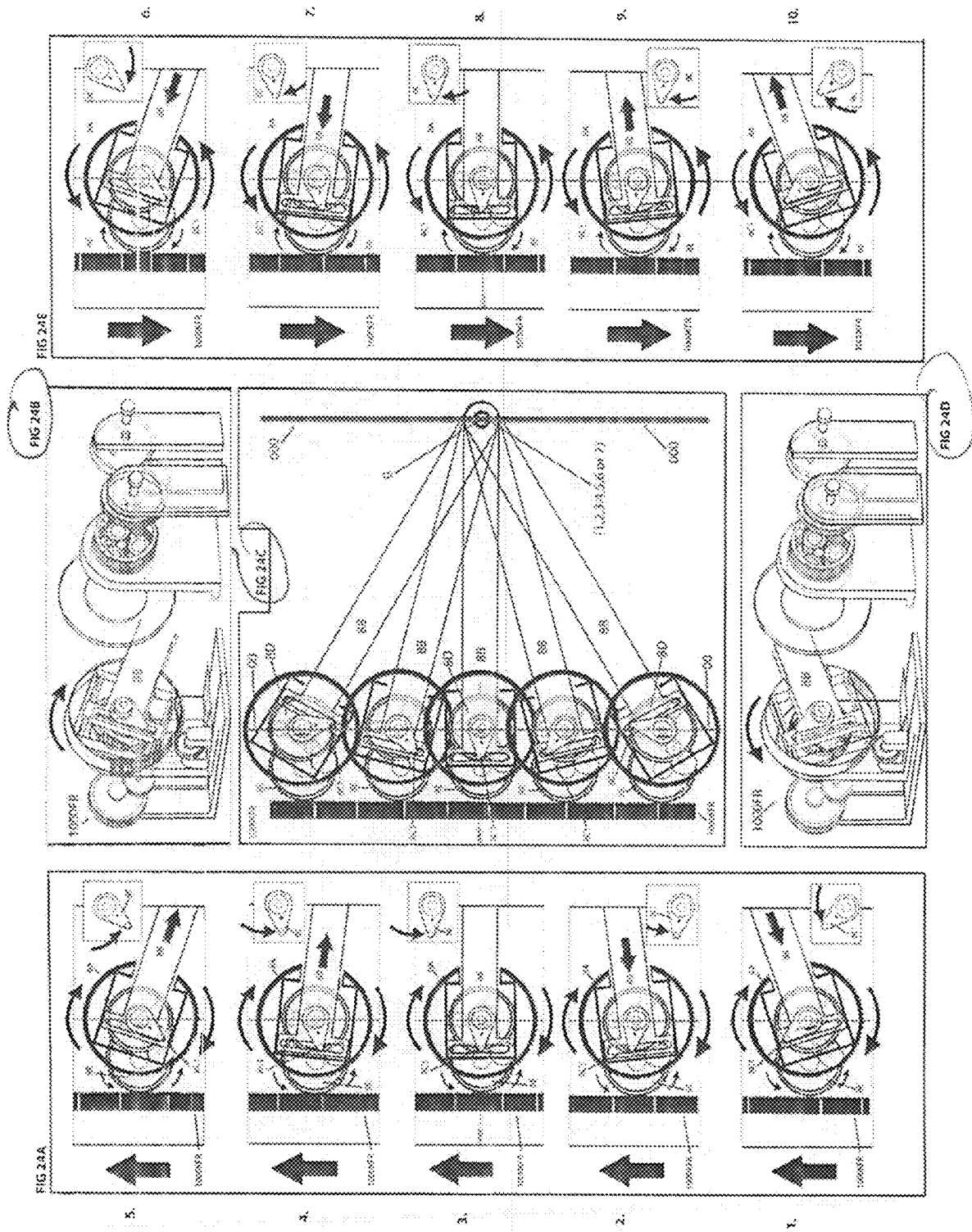

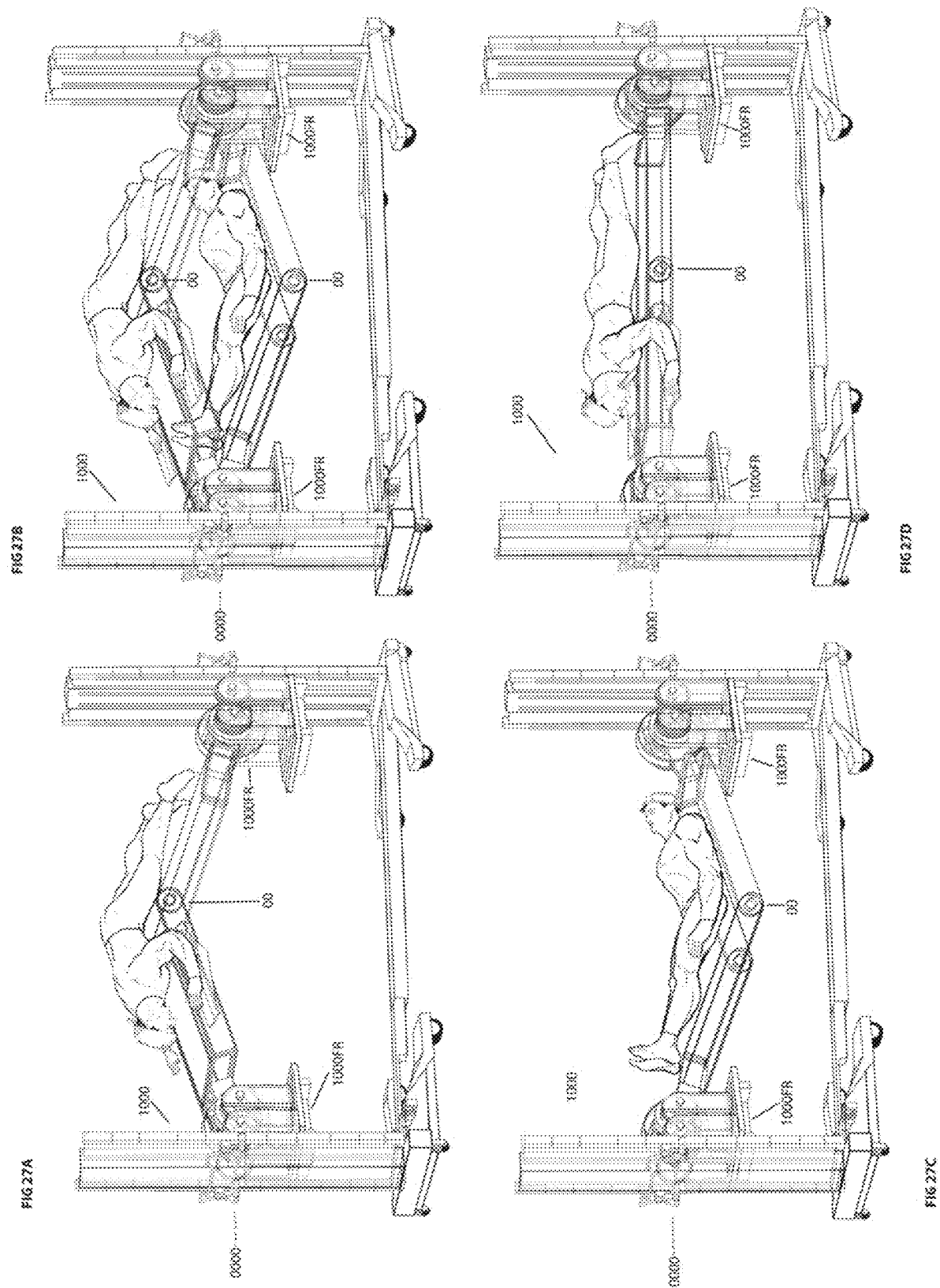

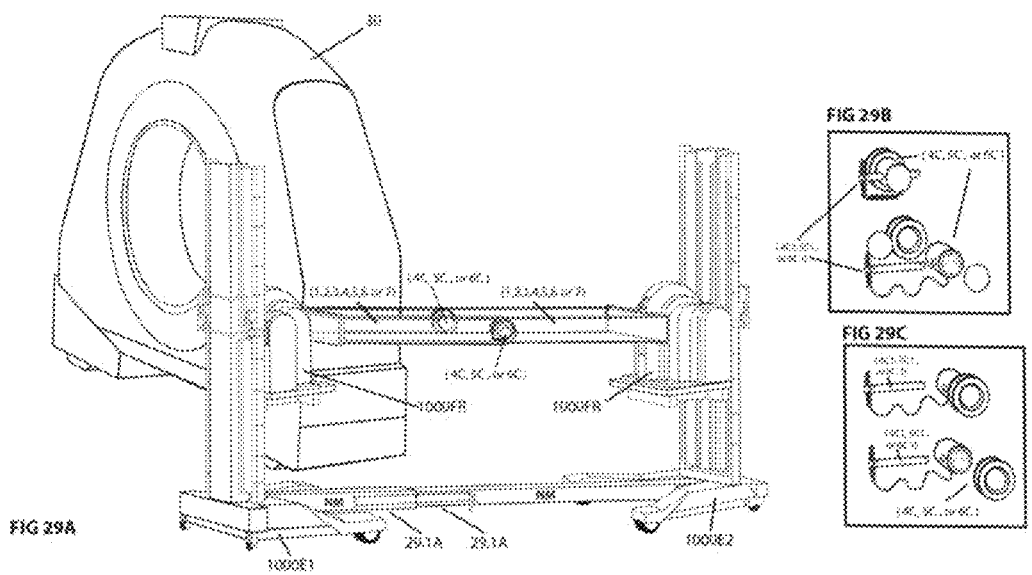
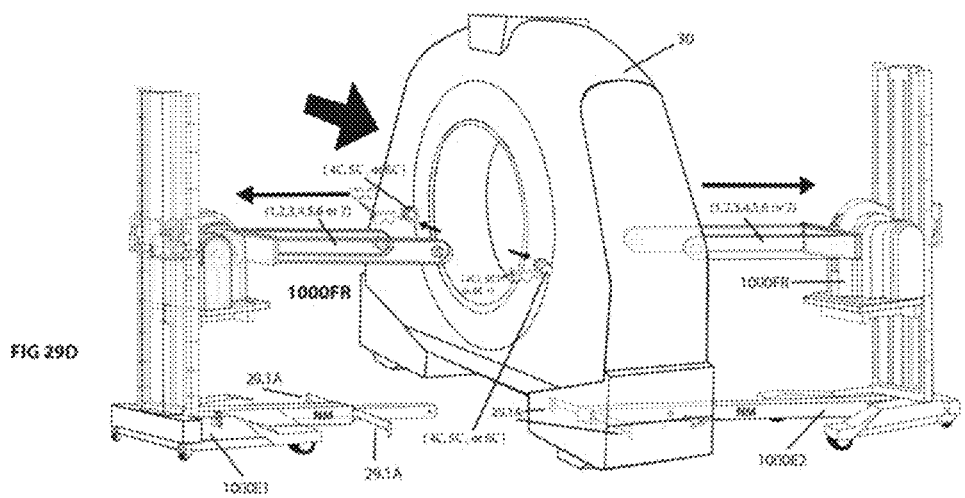
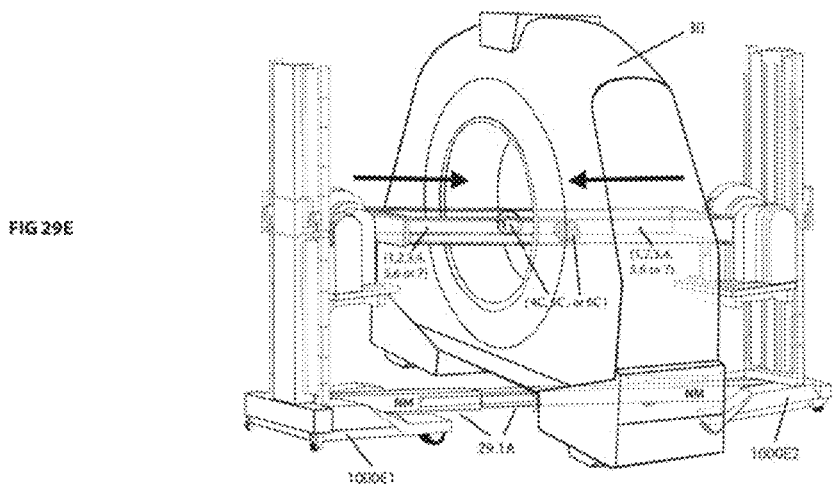

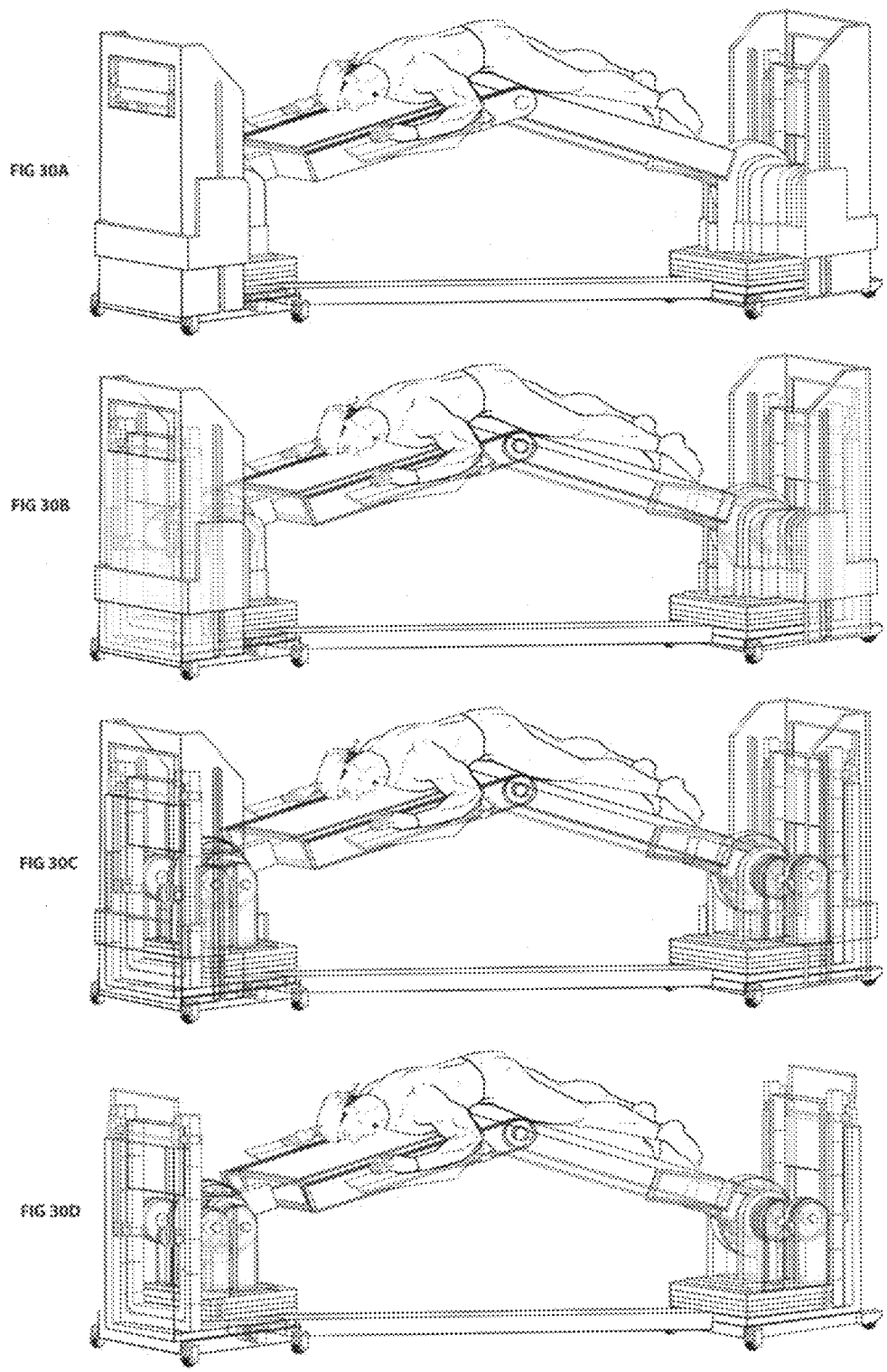

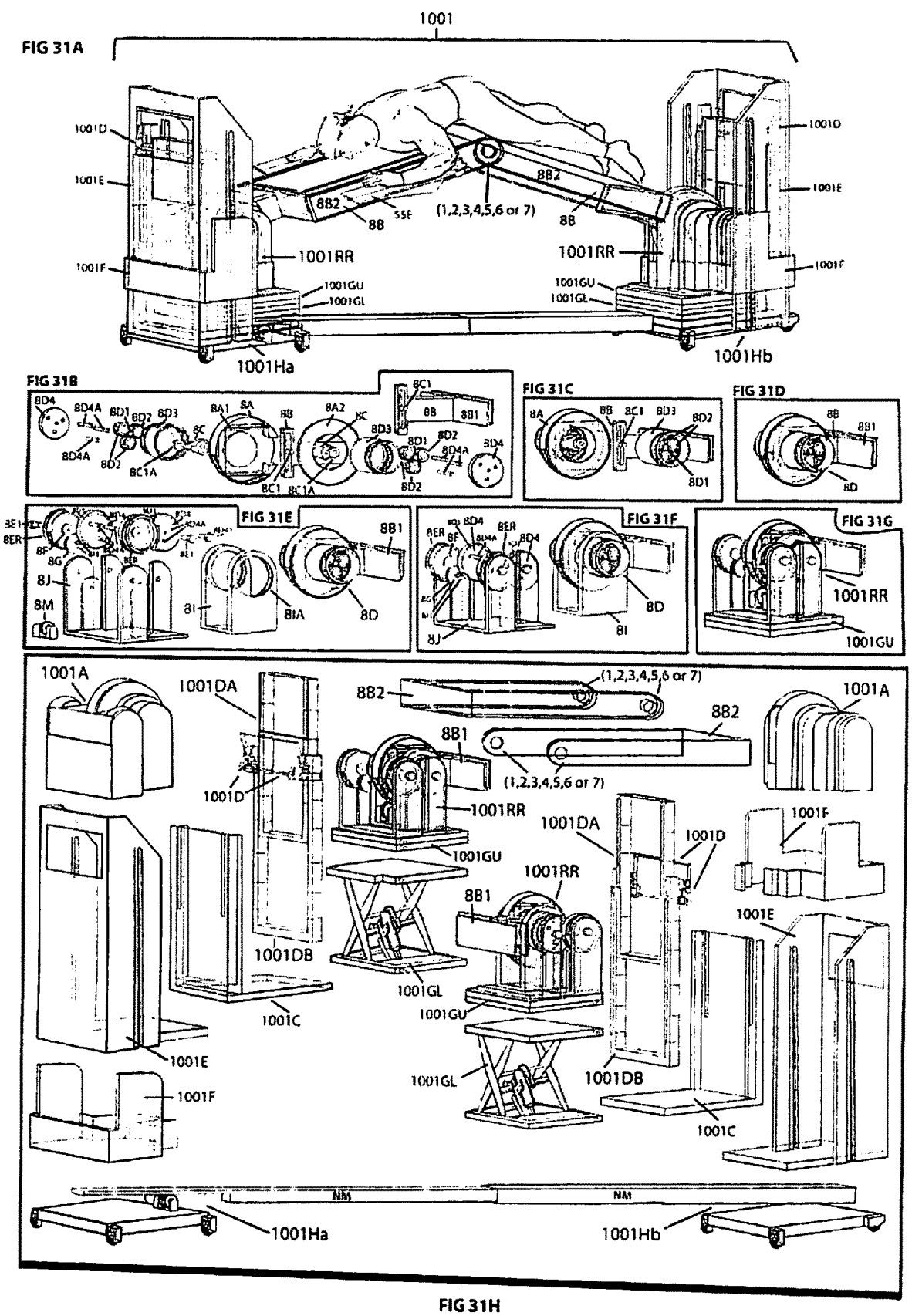

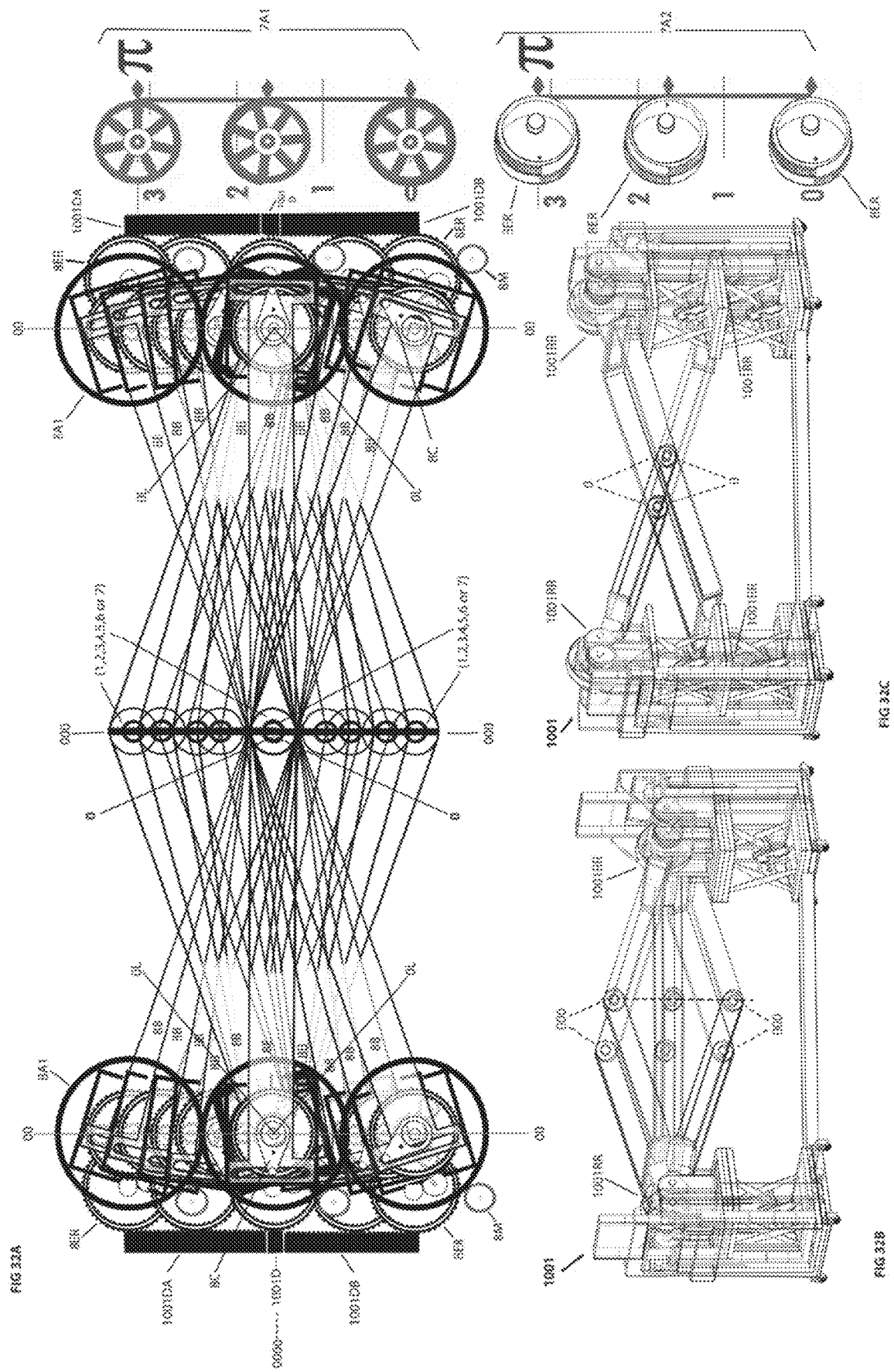

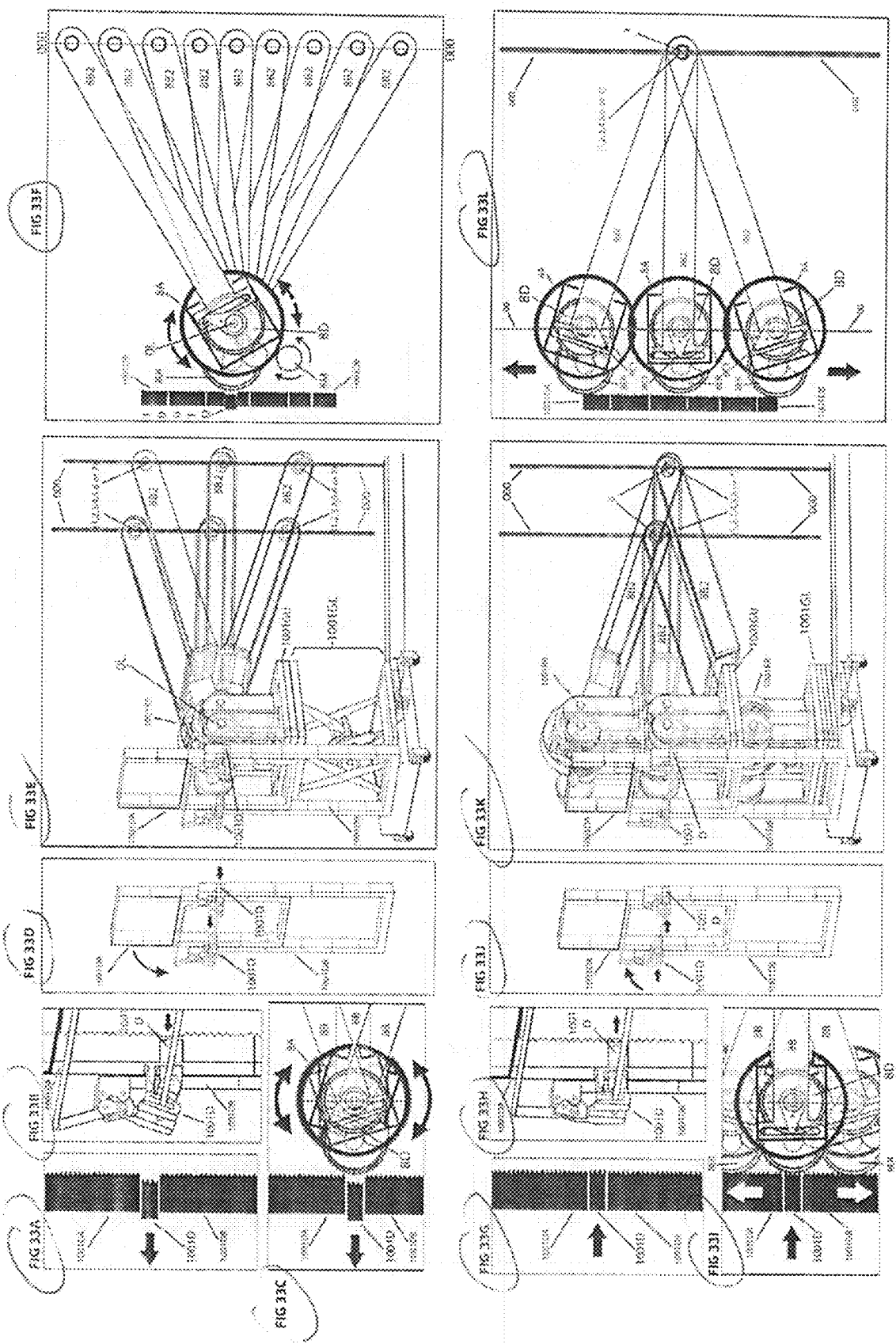

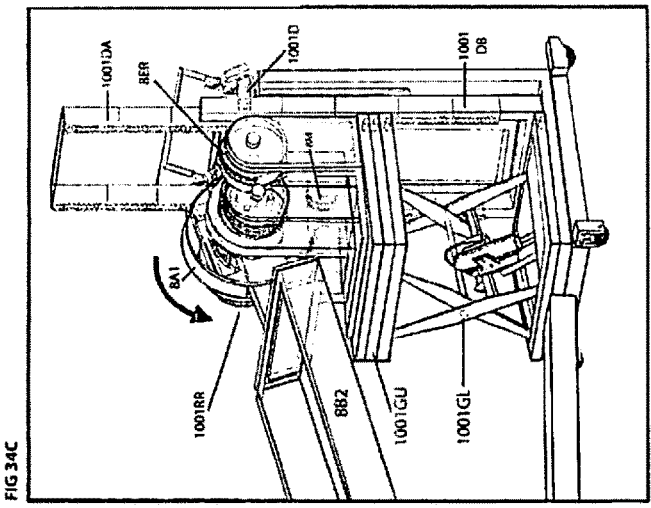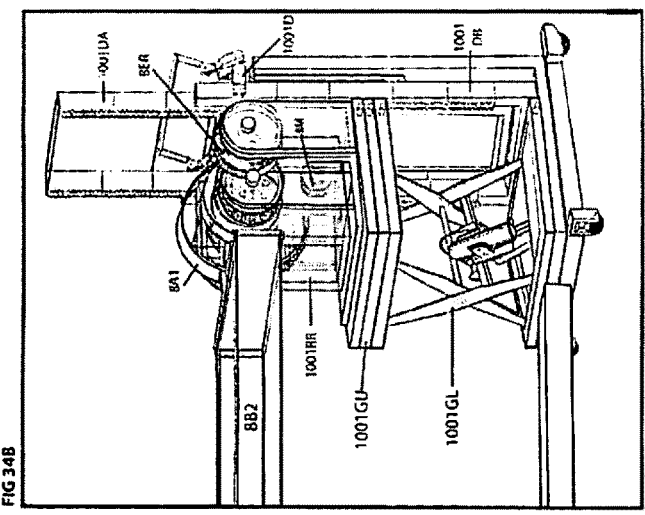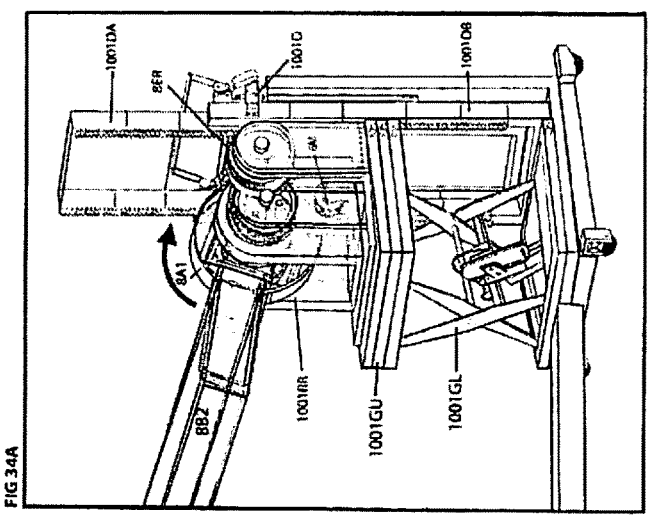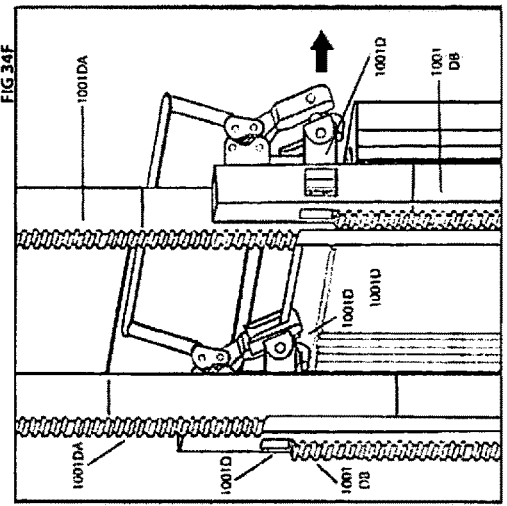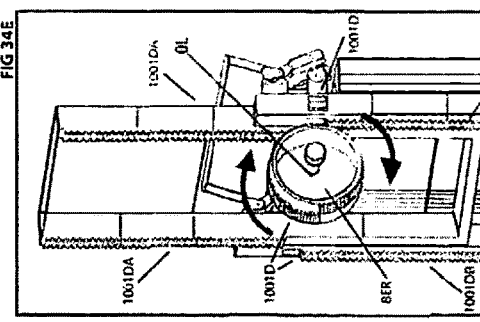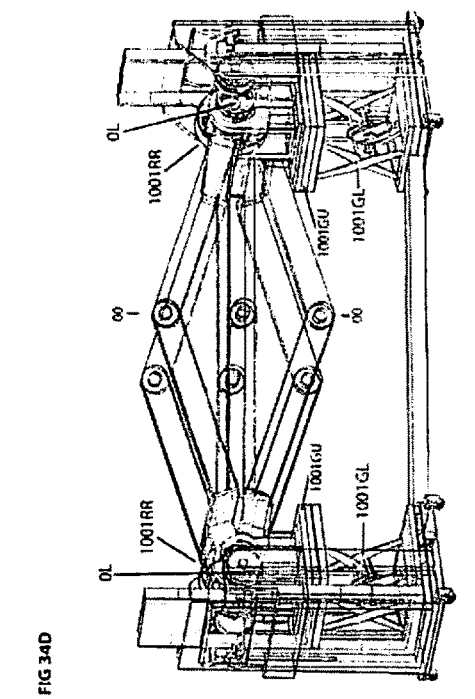

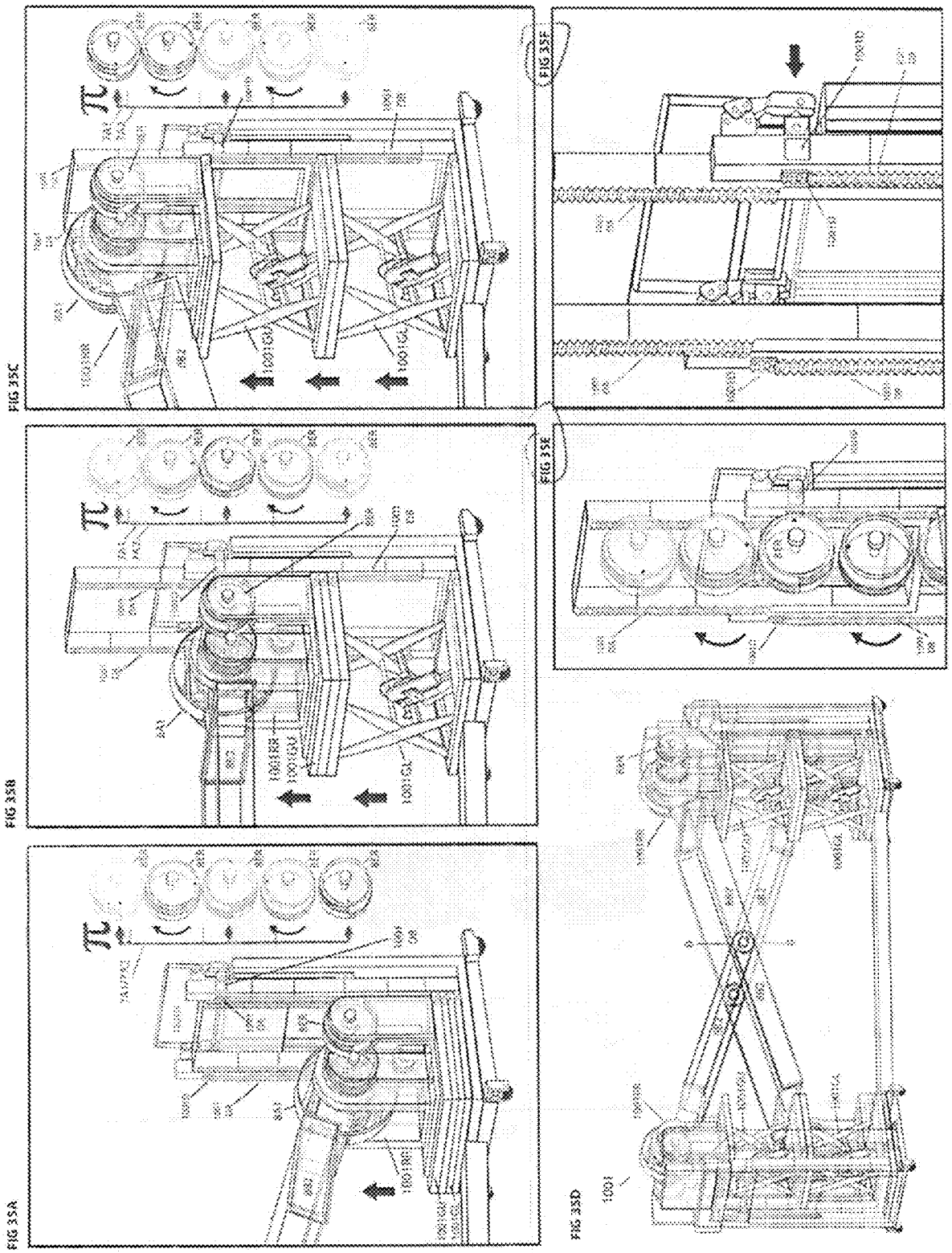

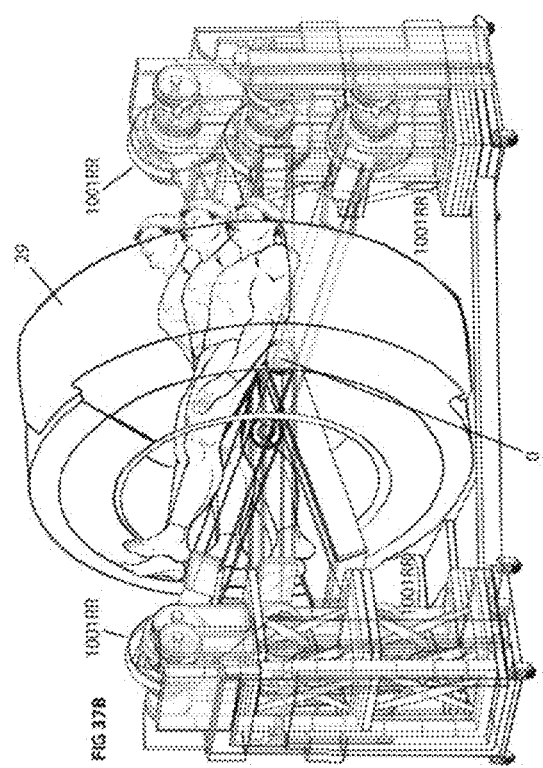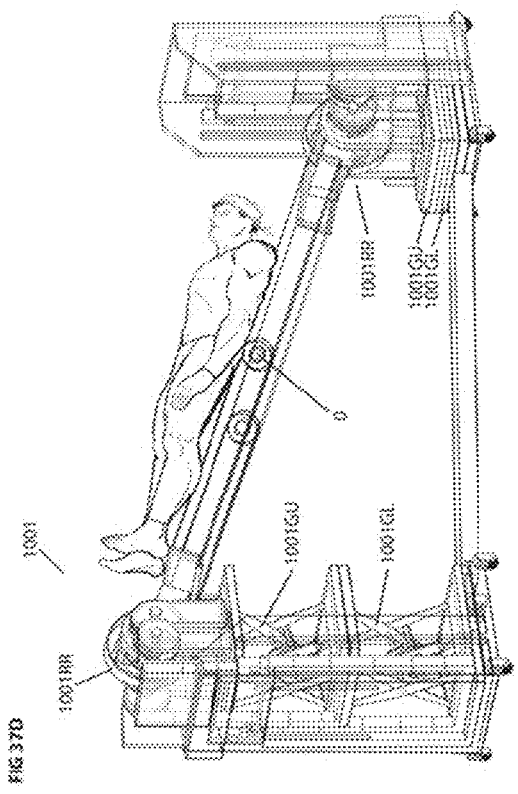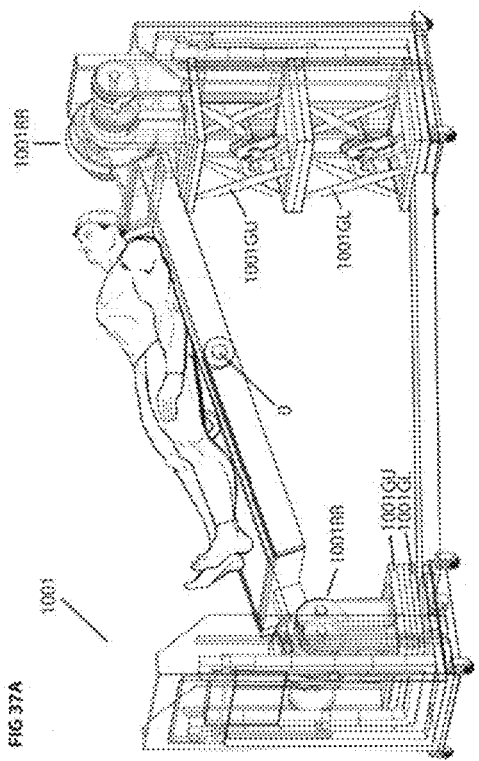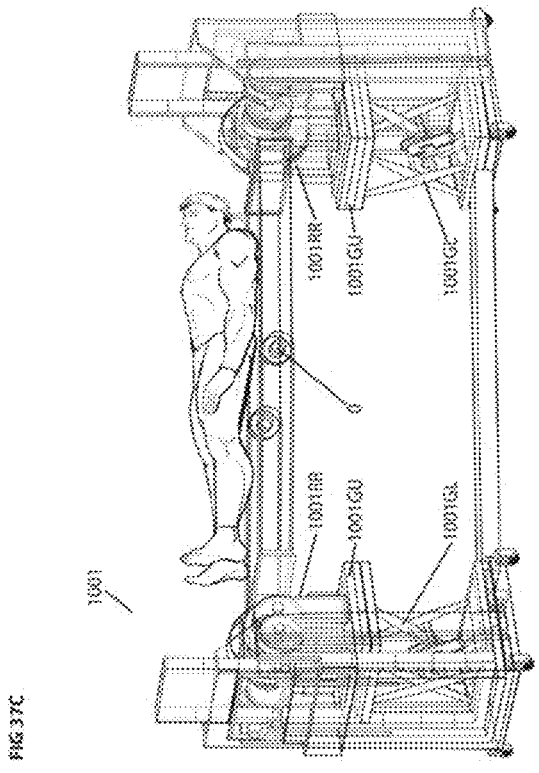

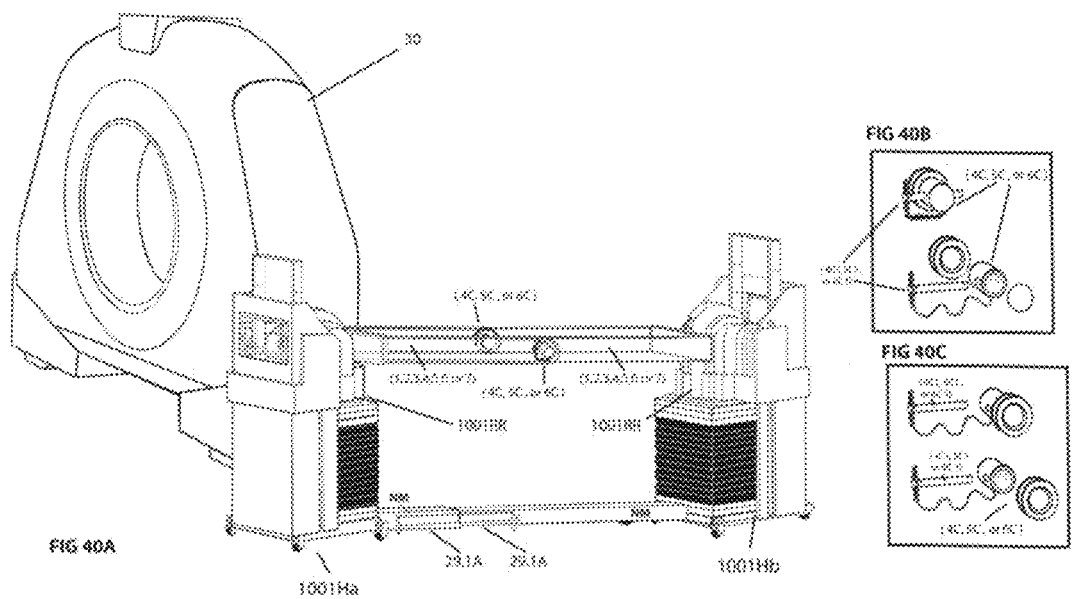
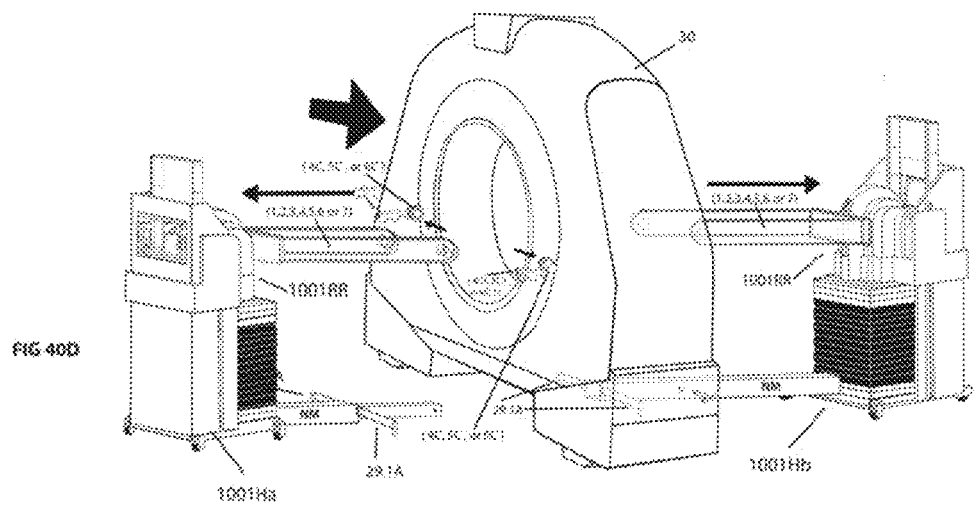
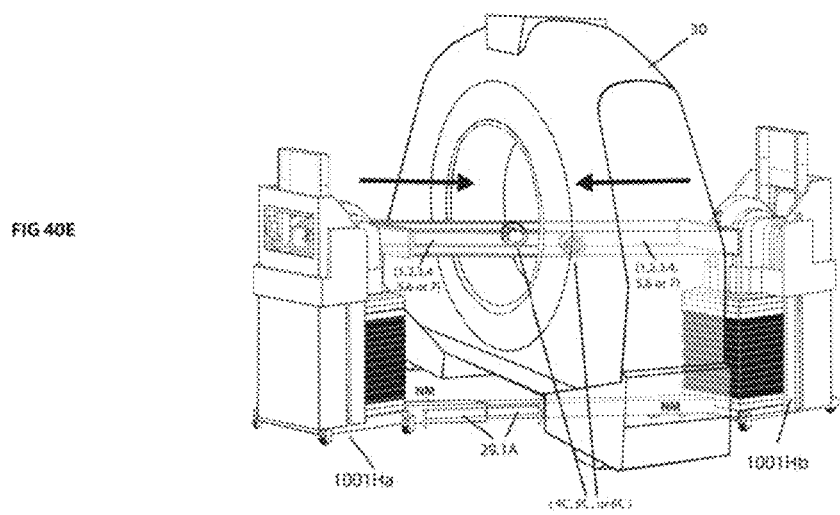

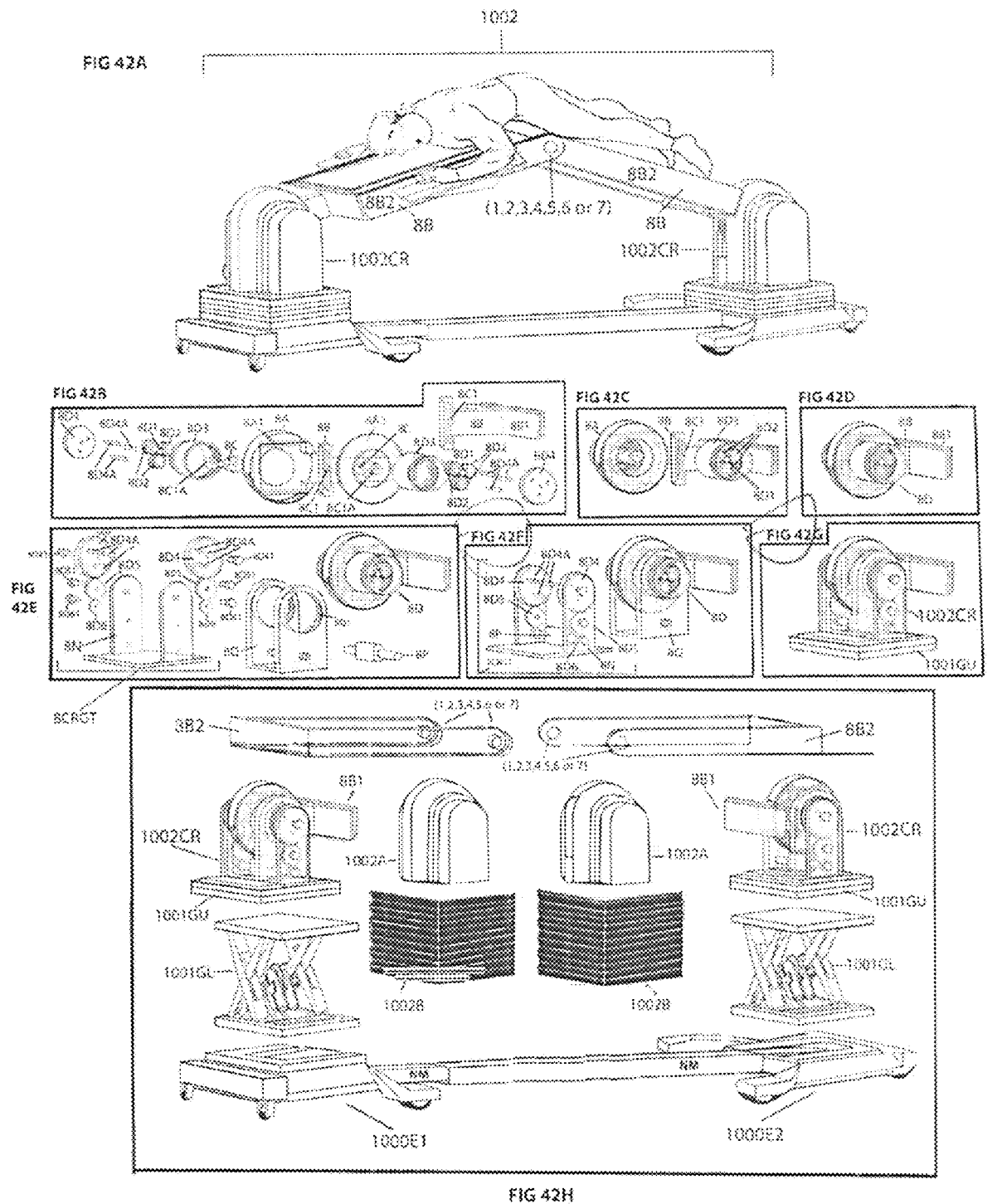

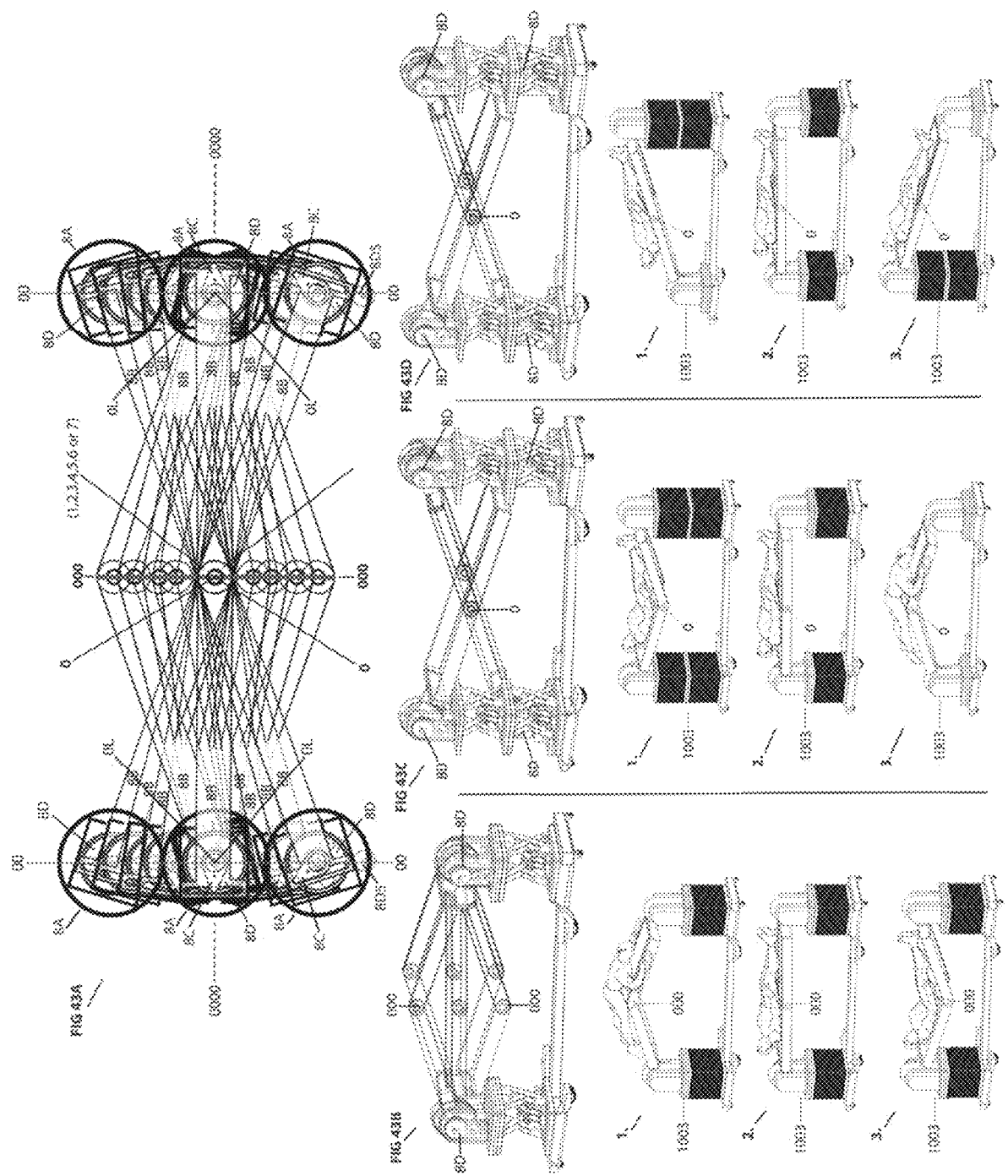

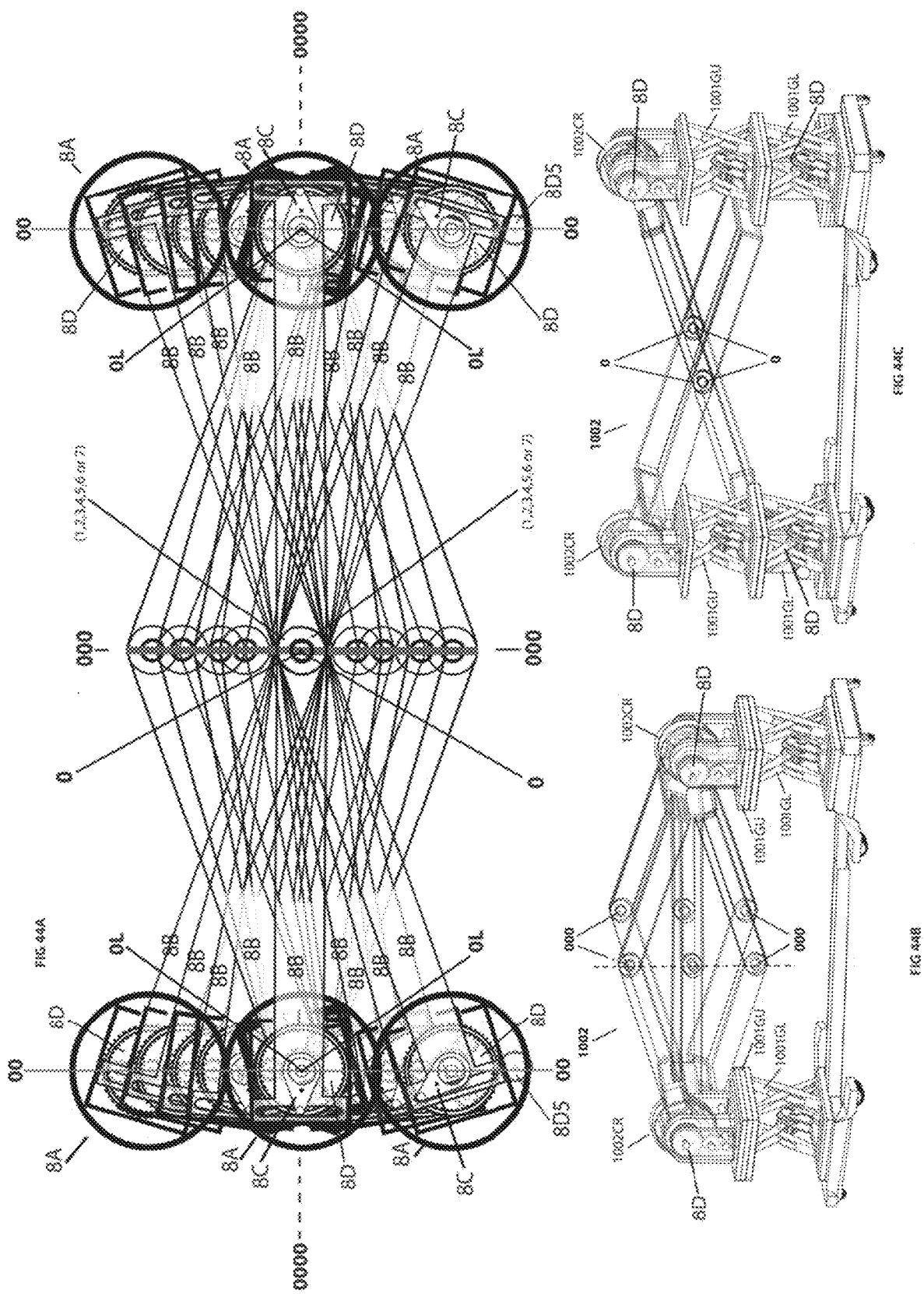

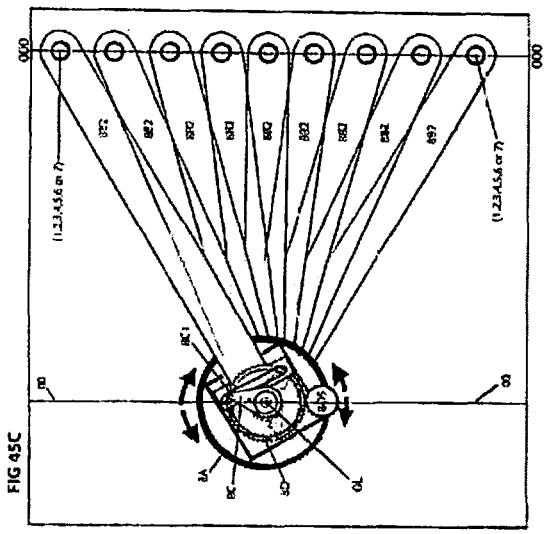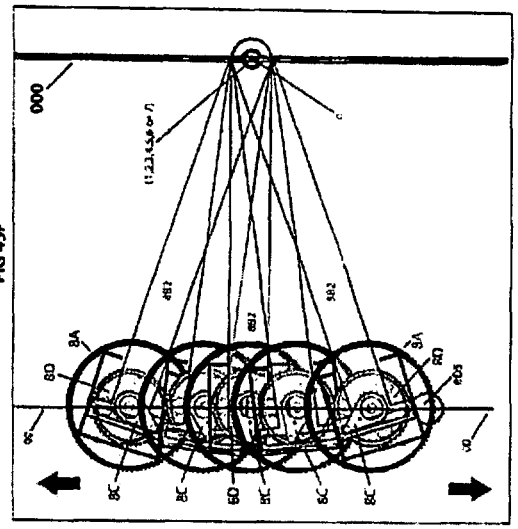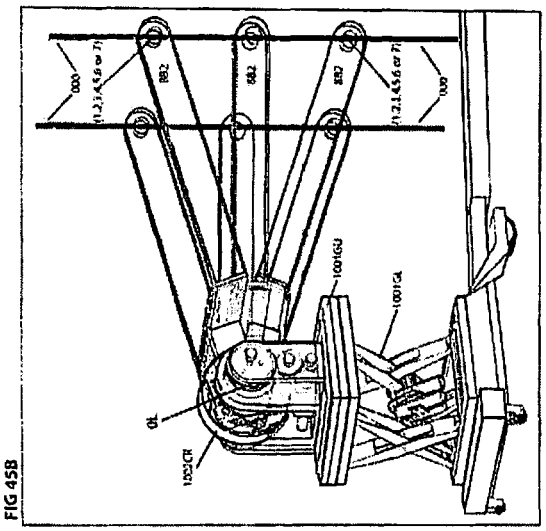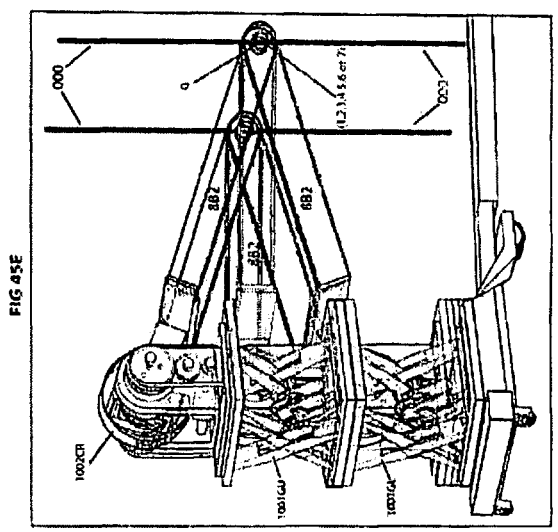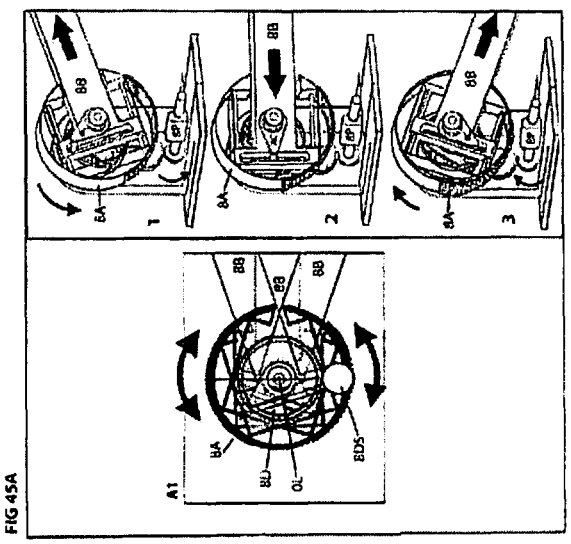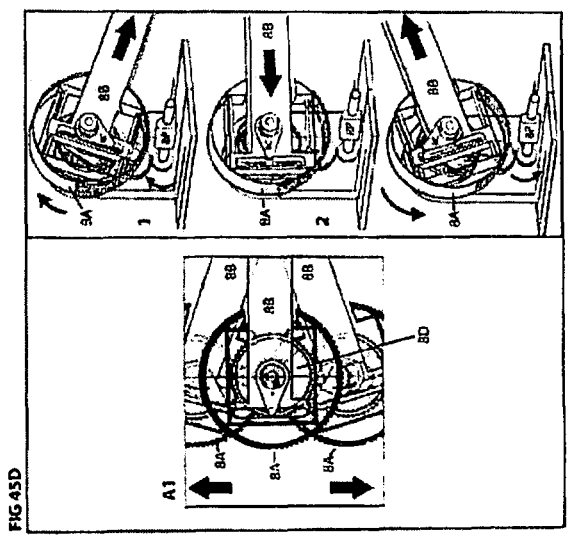

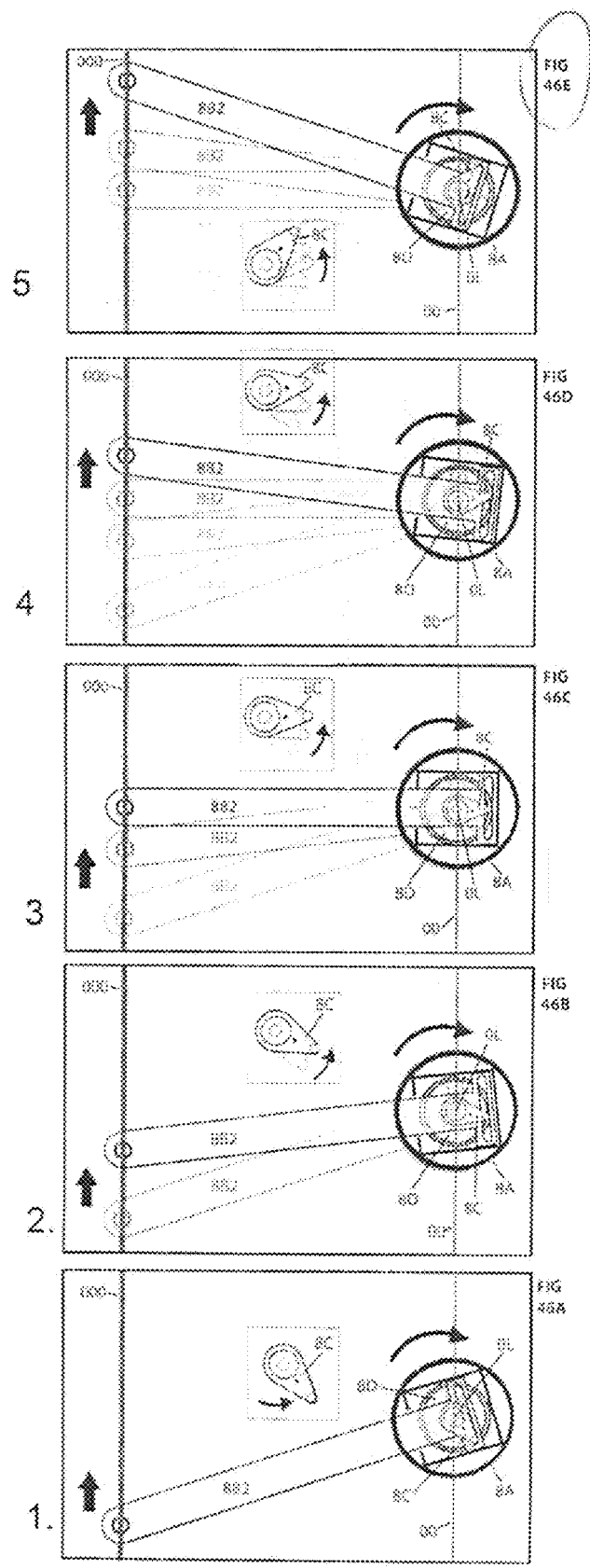
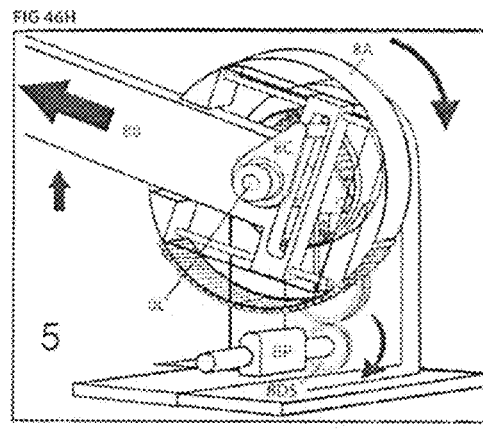
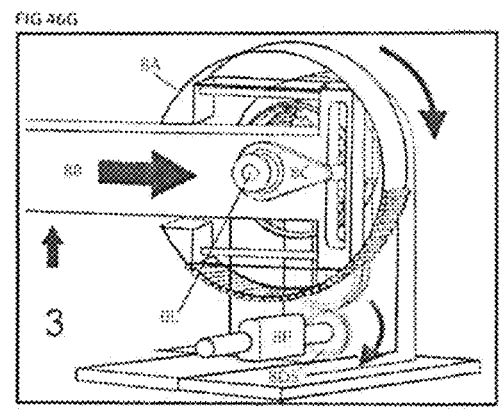
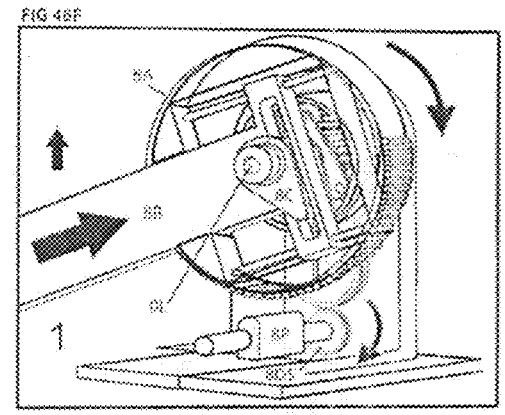

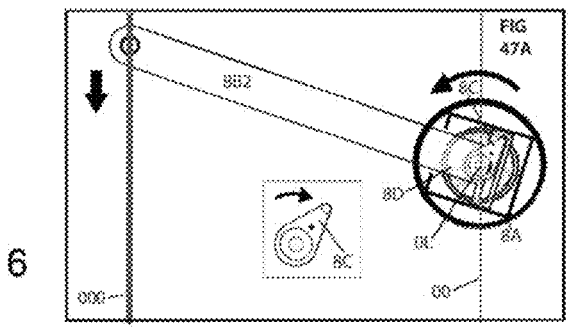
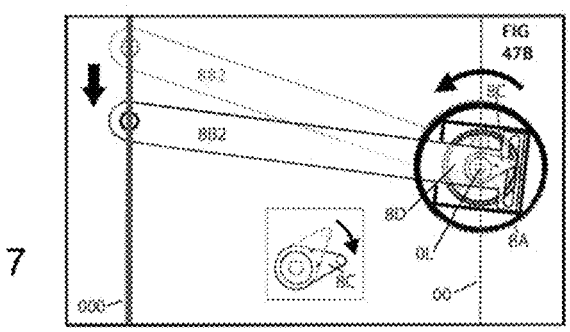
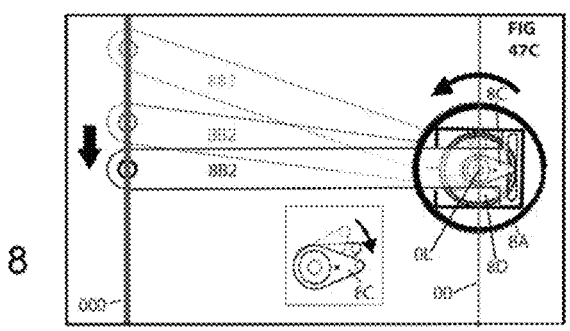
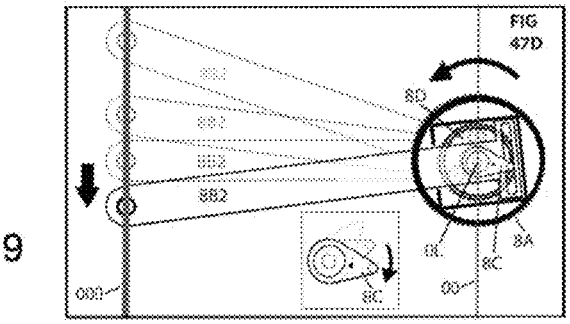
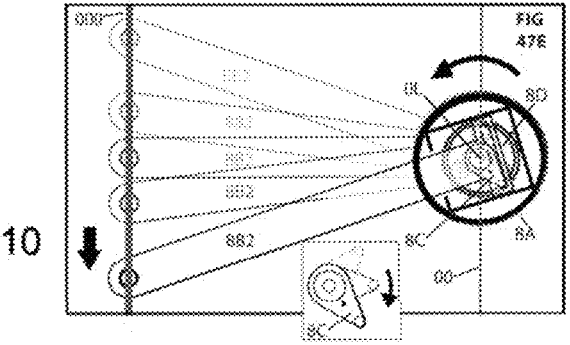
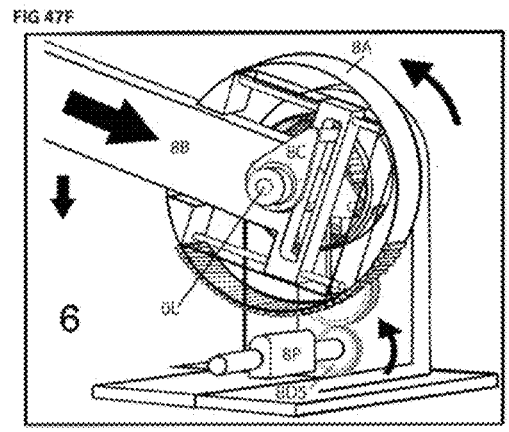
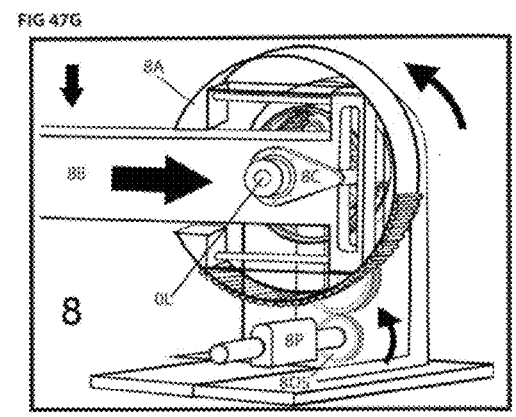
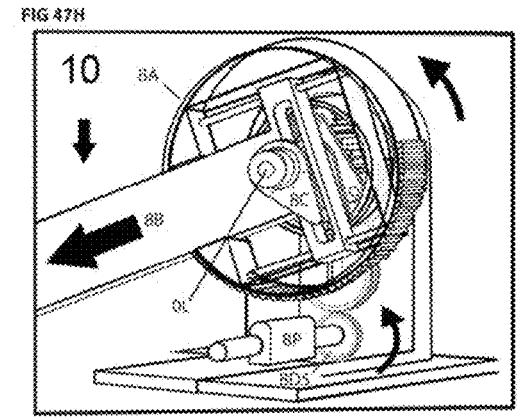

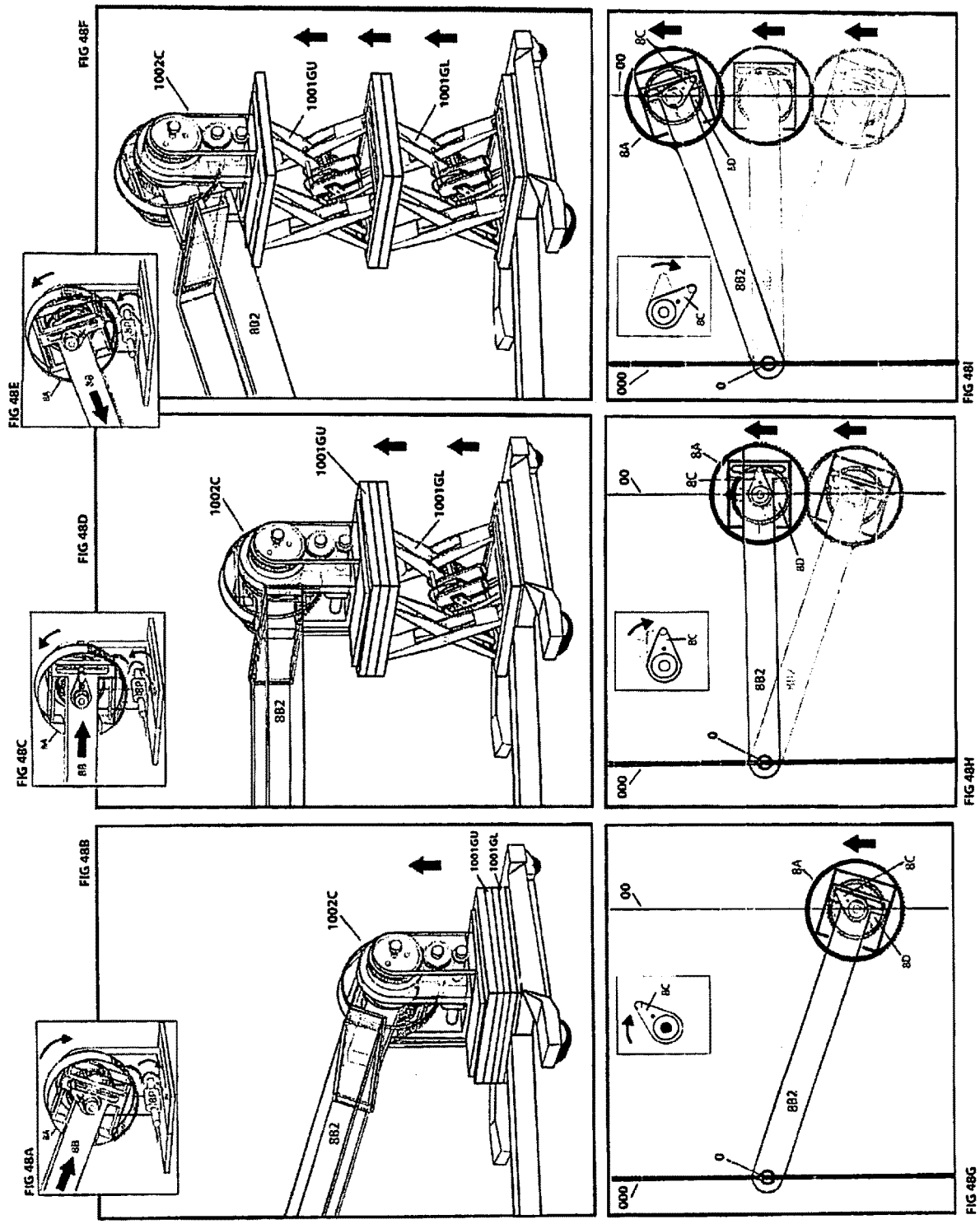

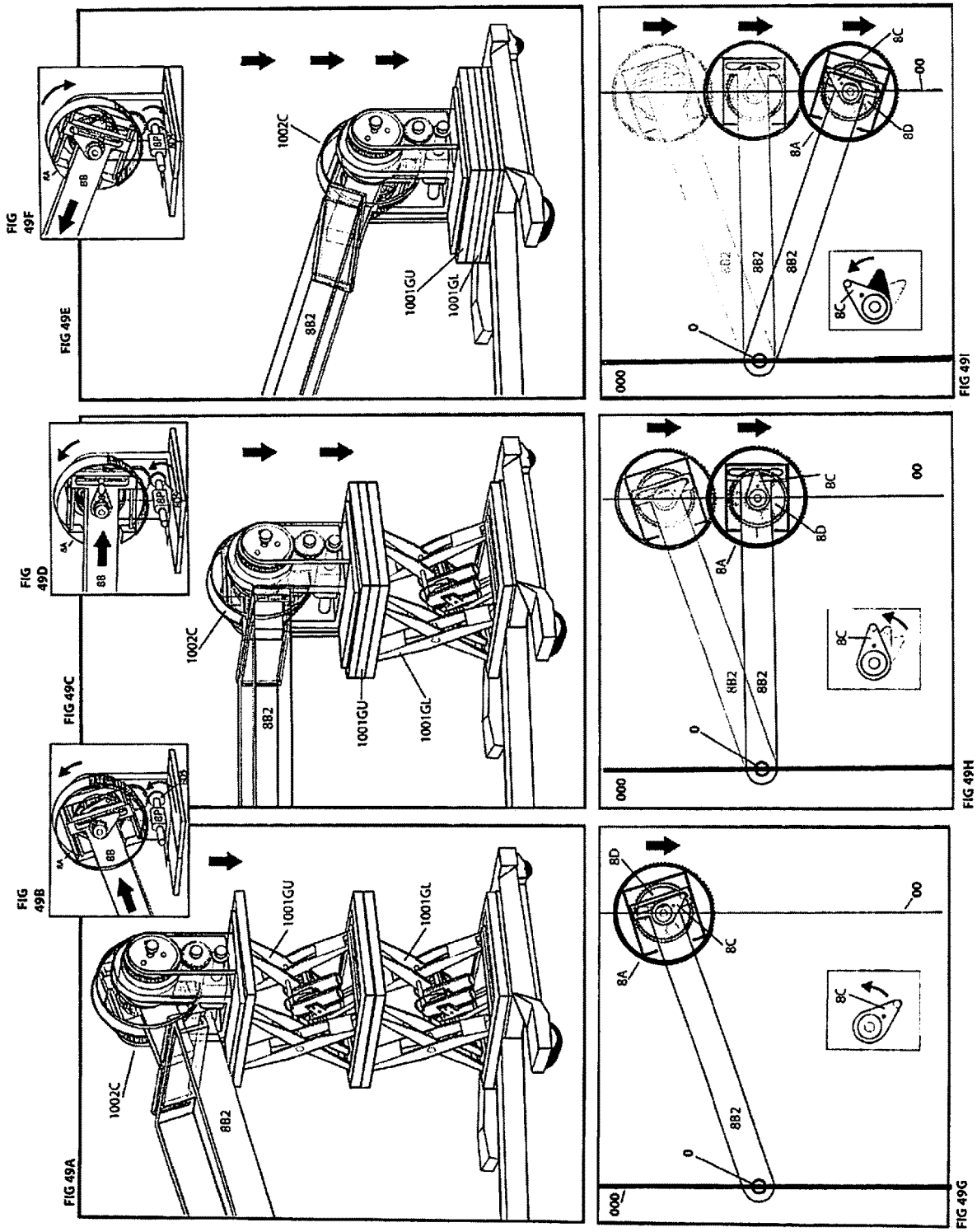

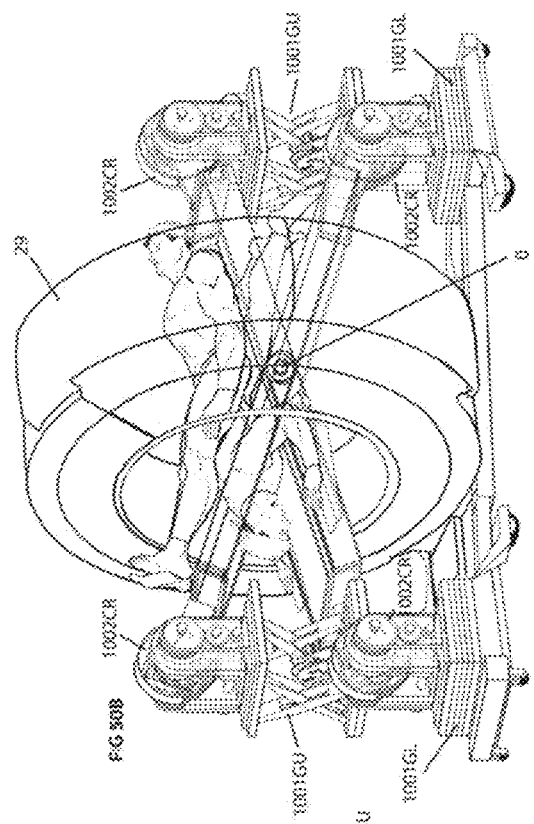
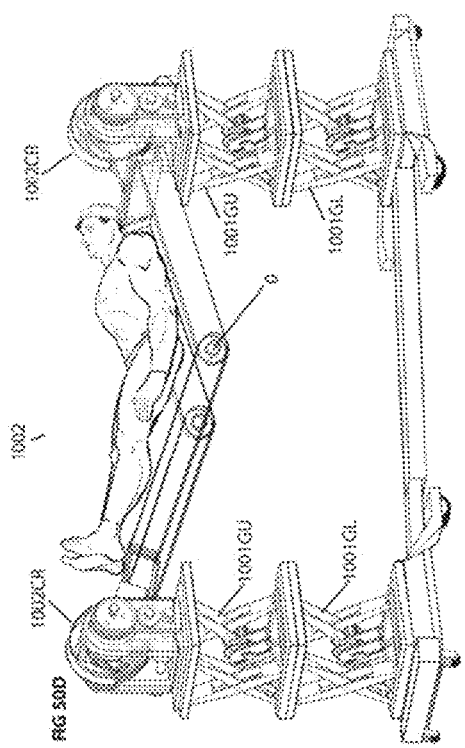
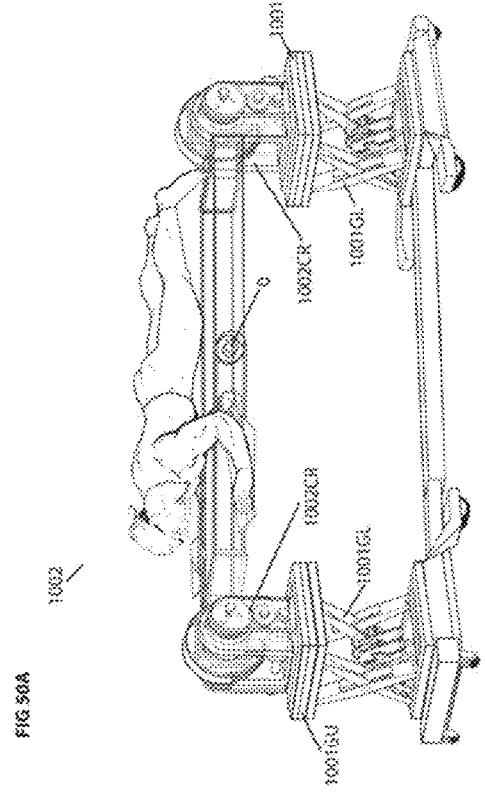
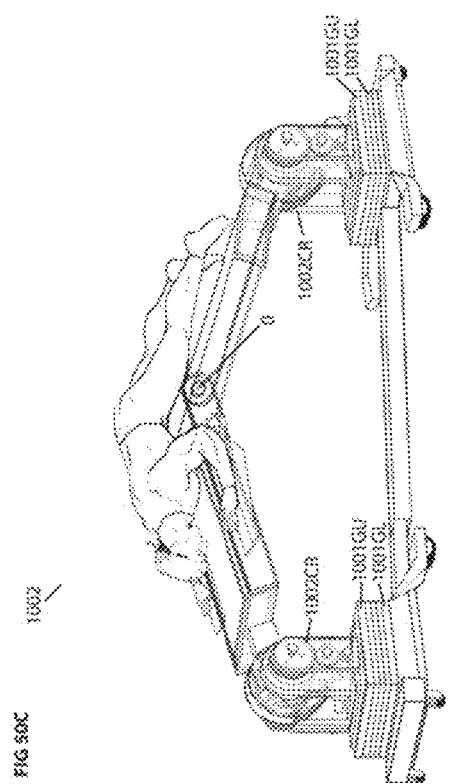

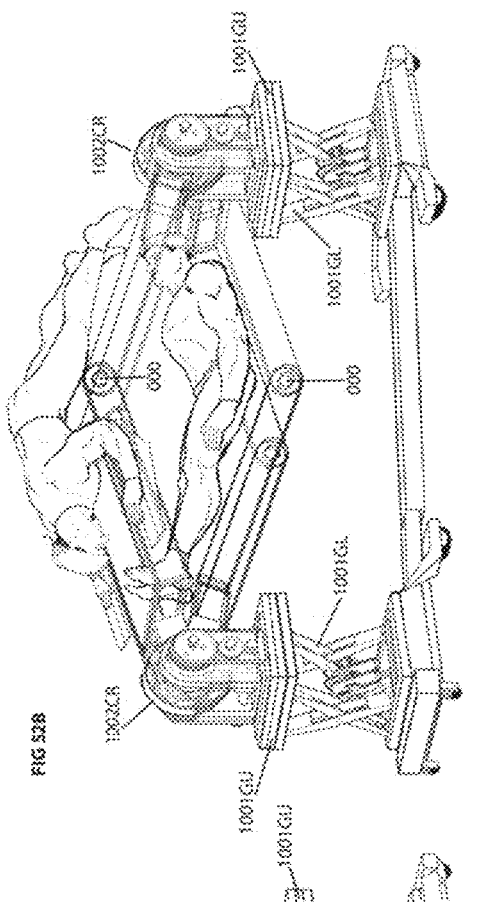

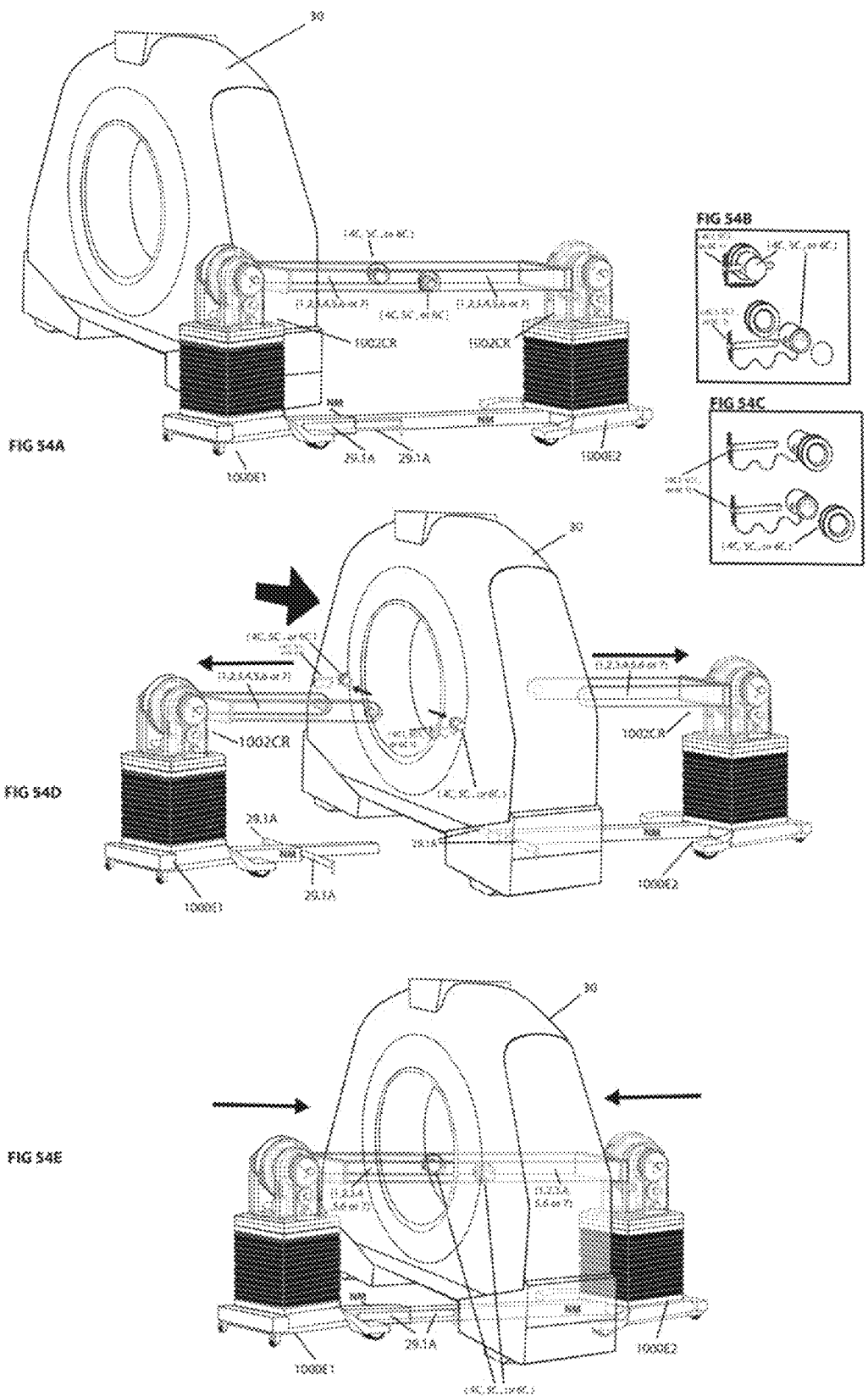

PATIENT PLATFORM, WITH COORDINATION VIA BILATERAL STRAIGHT-LINE MECHANISM

RELATED APPLICATIONS

This application claims priority to U.S. Provisional Application No. 63/062,846, titled PATIENT PLATFORM, WITH COORDINATION VIA BILATERAL STRAIGHT-LINE MECHANISM, filed on Aug. 7, 2020, and is incorporated in its entirety herein. This application also claims priority to U.S. Provisional Application No. 63/038,743, titled MEDICAL IMAGING COMPATIBLE RADIOLUCENT ACTUATION OF TRANSLATION ROTATION ARTICULATION CIRCUMDUCTION, filed on Jun. 12, 2020 and is incorporated in its entirety herein.

TECHNICAL FIELD

This application relates to patient platforms and, more particularly, to bilateral straight-line mechanisms used in patent platforms.

BACKGROUND

Surgical and imaging specific load-bearing patient platforms are incapable of the medically imaging compatible radiolucent flexion extension of a patient within the live magnetic and radiographic imaging bores without contributing significant radiographic and magnetic artifact to the resulting images, and thereby rendering such images as clinically unusable. The present invention teaches a method and apparatus for the medically imaging compatible radiolucent flexion/extension of the patient within the live magnetic and radiographic imaging arrays and incorporates by reference of U.S. Pat. No. 13/252,985 for Radiolucent One Degree of Freedom Flexion Extension of Patient Care Platforms designed for either the entire human (or animal) anatomy of the patient or specific portions thereof of said entire anatomy. Currently, approaches and solutions are available but have not solved the problem of radiolucent flexion/extension within said magnetic and radiographic imaging bores. Whereas, a need exists for a controlled safe and stable flexion/extension of a patient within the live magnetic and radiographic imaging bores and variably enables radiolucent imaging compatible flexion, Trendelenburg, reverse Trendelenburg, extension, fowlers positioning, and lateral decubitus positioning of an entire patient, with the full spectrum of positioning of the patient in any combination across the entire continuum thereof, in concert with a radiolucent flexion extension joint. Thus, a table is needed that is radiolucent and imaging compatible and able to be easily placed safely and effectively into a live imager while positioning a patient with minimal generation of magnetic or radiographic artifact and thereby enabling the creation and delivery of clinically usable live medical imaging during the controlled and predictable one degree of freedom flexion/extension of a patient within said magnetic and radiographic imaging bores. The present invention presents this solution but can also offer significant surgical and clinical benefit when configured in a non-radiolucent and imaging compatible manner due to the stable, safe, and controlled function of the bilateral straight-line mechanism when configured as a patient care platform.

SUMMARY

The bilateral straight-line mechanism of the present invention, which is comprised of a differential planetary gearbox with reciprocating scotch yoke, is utilized as a means of Coordinating the flexion and extension of radiolucent, medically imaging compatible, one degree of freedom flexion/extension, rotatable hinge joint and radiolucent rotatable joint, when the radiolucent hinge joints are configured as a surgical table platform enabled to be fully inserted and articulated/rotated with a patient in the active magnetic and radiographic medical imaging device. Where the radiographic medical imaging device includes Magnetic Resonance Imaging (MRI), Computerized Tomography (C.T.), the O-arm 3D cone beam fluoroscopy, C-arm fluoroscopy, and Positron Emission Tomography (PET), and hybrid surgical suites, in a radiolucent, magnetic resonance (M.R.) safe, medically imaging compatible manner, demonstrated to neither significantly affect the quality of the diagnostic information nor have its operations affected by the medical imaging system.

The bilateral straight-line mechanism portion of the present invention, as presented herein, is to be used in concert with the radiolucent one degree of freedom flexion extension joint in order to work in proximity to and with radiographic and magnetic resonance imaging bores or within the hybrid operating room. However, due to the significant danger of ferromagnetic metal components becoming fatal projectiles in proximity to the live magnetic resonance imaging bore, iterations of the present invention that are designed to be used in proximity to the MRI (Magnetic Resonance Imaging) bores must be constructed either from non-ferromagnetic metals such as aluminum or stainless steel, or must be constructed from non-metallic means such as Delrin, nylon 6/6, polyacetal, polyphenylene sulfide (PPS), thermoplastic polyester, long fiber reinforced plastic and liquid crystal polymers (LCP), acetal copolymers, thermoplastic polyesters, liquid crystal polymers, linear polyphenylene sulfides, long fiber reinforced plastics, non-crystalline plastics, polycarbonate with glass reinforcement or a solid lubricant such as PTFE to obtain satisfactory lubricity, chemical resistance, and fatigue properties, as well as other materials that offer strength, elastic modulus, thermal expansion, moisture absorption, and friction characteristics equal to the load-bearing task, while also preventing the danger of ferromagnetic metals becoming fatal projectiles in proximity to the live MRI magnetic bore. Iterations of the present may also be constructed of other suitable non-metallic materials which exist and are under development. Whereas the bilateral straight-line mechanism portion of the present invention, if constructed of ferromagnetic metals, may also be utilized in proximity to radiographic only imaging bores. One skilled in the art will readily surmise that cylindrical elongation of the planetary gearing the present invention presented herein will assist in non-metallic load-bearing iterations of the BLSLM.

Other devices, apparatus, systems, methods, features, and advantages of the invention will be or will become apparent to one with skill in the art upon examination of the following figures and detailed description. It is intended that all such additional systems, methods, features, and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views. FIGS. 1-55 are of the embodiments and components of the Bilateral Straight-Line Mechanism used in a patient support device in accordance with an example implementation of the invention.

FIG. 1A is a diagram of a flexion and extension of an imaging compatible radiolucent rotatable hinge joint configured as a patient platform 1000, with coordination via a bilateral straight-line mechanism in accordance with an example implementation.

FIG. 1B is a diagram of another implementation of the imaging compatible radiolucent rotatable hinge joint configured as a patient platform 1001, with coordination via a bilateral straight-line mechanism, in accordance with an example implementation.

FIG. 1C is a diagram of yet another implementation of the imaging compatible radiolucent rotatable hinge joint configured as a patient platform 1002, with coordination via bilateral straight-line mechanism, in accordance with an example implementation.

FIG. 1D is the patient platform 1001 of FIG. 1B supporting a patient within an imager ring 29 in accordance with an example implementation.

FIG. 1E is the patient platform 1002 of FIG. 1C within an imager 32 in accordance with an example implementation.

FIG. 1F is the patient platform 1000 of FIG. 1A positioning a patient between the arms of imager 21 in accordance with an example implementation. The patient platform 100 is a radiolucent flexion/extension spine table fixed rack iteration 1000 of the radiolucent hinge when configured as a radiolucent, imaging compatible, flexion/extension patient platform, spine table utilizing the BSLM for coordination of the mated flexion/extension of radiolucent members 8B which form the radiolucent hinge.

FIG. 1G is the patient platform 1002 of FIG. 1C is depicted being placed through another imager 30 using sensors 35 and controller 36 in accordance with an example implementation.

FIG. 2A is a radiolucent joint 1 illustration with one degree of freedom that may be used in the center joint of the patient platform 1000, 1002, 1003 of FIGS. 1A-1C in accordance with an example implementation.

FIG. 2B is a radiolucent joint 2 illustration with one degree of freedom that may be used in the center joint of the patient platform 1000, 1002, 1003 in accordance with an example implementation.

FIG. 2C is an illustration of another radiolucent joint 3 in accordance with an example implementation.

FIGS. 2D-2F are illustrations of radiolucent laminar buttresses 7 providing support to members 1A, 1B, 2A, 2B, 3A, and 3C in accordance with an example implementation.

FIG. 3A-3F are similar to FIGS. 2A-2F, depicting a rotatable joint 4, 5, 6 made from radiolucent laminar sheeting 4A, 4B, 5A, 5B, 6A, and 6B, each with removable radiolucent pin 4C, 5C, and 6C that enable the respective joints to move and in a respective position "A"-"D" of FIGS. 3A-3C in accordance with an example implementation.

Turning to FIG. 4A, an illustration of a bilateral straight-line mechanism (BSLM) that coordinates the mated flexion/extension of yoked laminar members 8B of the radiolucent hinge when configured as a radiolucent imaging compatible Patient platform insertable into live magnetic and radiographic medical imaging bores in accordance with an example implementation.

FIGS. 4B-4D depict the BSLM of FIG. 4A in a different position in accordance with an example implementation of the invention.

FIGS. 4E-4G depict the operation of different patient supports using the BSLM of FIG. 4A in accordance with example implementations.

In FIGS. 6A-6E, the components of the BSLM 8 are shown in more detail, and its operation is explained in accordance with an example implementation.

FIGS. 7A-7E depict component diagrams of the gear orientation of the BSLM in accordance with an example implementation.

FIGS. 8A-8M depict the differential planetary gear 8D coupled with the slotted scotch yoked radiolucent laminar member 8B in accordance with an example implementation.

FIGS. 9A-9M are depictions of the operation of the differential planetary gear 8D coupled with the slotted scotch yoked radiolucent laminar member 8B in accordance with an example implementation.

FIGS. 10A-10E are depictions of the operation of the differential planetary gear 8D coupled with the slotted scotch yoked radiolucent laminar member 8B show the translation of circular motion to in and out motion in accordance with an example implementation.

FIGS. 11A-11E further depict the operation of the BSLM with the differential planetary gear 8D coupled with the slotted scotch yoked radiolucent laminar member 8B show the translation of circular motion to in and out motion in accordance with an example implementation.

FIGS. 13A-13L are further depictions of the components of the patient support of FIG. 12C employing differential planetary gears 8D in accordance with an implementation of the invention.

FIG. 14A is a depiction of BSLM with embodiments 1000, 1001, and 1002 where sensor 35 monitors the position of the patient positioner via retro-reflective fiducial markers in accordance with an example implementation.

FIG. 14B depicts different graphical images 14a-14l that represent the position of the patient platform after a user using the touch screen caused the movement in accordance with an example implementation.

FIG. 14C is an illustration of a hand controller 38 that may be coupled to controller 36 or to the patient platform by a direct connection or a wireless connection in accordance with an example implementation.

FIGS. 15A-15C, 16A-16C, 17A-17C, and 18A-1B depict additional examples of the BSLM in accordance with example embodiments.

FIGS. 19A-19C, 20A-20H, 21A-21C, 22A-22L, 23A-23I, 24A-24E, 25A-25D, 26A-26D, 27A-27D, 28A-28D, 29A-29E are illustrations of the patient support and components of the patent support are depicted in accordance with an example implementation.

FIGS. 30A-30D, 31A-31H, 32A-32C, 33A-33L, 34A-34F, 35A-35F, 36A-36D, 37A-37D, 38A-38D, 39A-39D are illustrations of additional patient support and components of the patent support are depicted.

FIGS. 40A-40E, 41A-41D, 42A-42D, 43A-43D, 44A-44C, 45A-45F, 46A-46H, 47A-47H, 48A-48I, 49A-49I, 50A-50D, 51A-51D, 52A-52D, 53A-53D, 54A-54E, 55A-

Figure 5A:
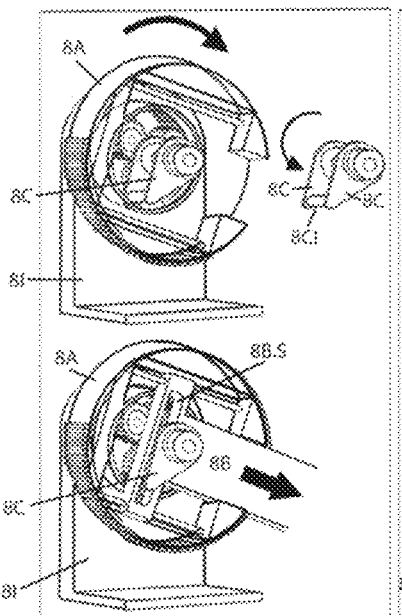
Turning to FIGS. 5A-5F, the operation of the scotch yoke is depicted with the different types of supports 1000, 1001, and 1002 have a depiction of the respective scotch yoke 100FR, 1001RR, and 1002CR in accordance with an example implementation.

55C are illustrations of additional patient support and components of the patent support are depicted.

DETAILED DESCRIPTION

In FIG. 1A, a diagram of a flexion and extension of an imaging compatible radiolucent rotatable hinge joint configured as a patient platform 1000, with coordination via a bilateral straight-line mechanism, is depicted in accordance with an example implementation. Turning to FIG. 1B, a diagram of another implementation of the imaging compatible radiolucent rotatable hinge joint configured as a patient platform 1001, with coordination via bilateral straight-line mechanism, is depicted in accordance with an example implementation. In FIG. 1C, a diagram of yet another implementation of the imaging compatible radiolucent rotatable hinge joint configured as a patient platform 1002, with coordination via a bilateral straight-line mechanism, is depicted in accordance with an example implementation. The different implementations depict that the patient platform may have supports of different heights that are able to lift the straight-line mechanism to aid in patient placement in an imager.

In FIG. 1D, the patient platform 1001 is depicted supporting a patient within an imager ring 29 is depicted. One or more sensors, such as sensor 35, may track the position of the patient platform 1001 and provide that data to a controller, such as a controller 36 configured with a touch screen in this current implementation. Sensor 35 may track or identify the position of the patient platform 1001 by identifying the location and movement of markers located on the patient platform. The controller 36 graphically depicts the location of the patient platform on the screen, and sensors, such as touch sensors in the screen, allow input to the controller to send (wired or wirelessly) signals to the patient platform to change the orientation of the patient platform. In other implementations, controller 36 may be located near the patient platform 1001, one the patient platform 1001, or at a remote location. The remote location may be on earth, with the patient platform 1001 located on a space station, ship, or even another planet.

Turning to FIG. 1E, the patient platform 1002 of FIG. 1C is depicted within an imager 32 in accordance with an example implementation. Sensors 35 (two sensors are depicted) monitor the location of the patient platform 1002 in the imager 32 and provide the data to the controller 36. Similarly, in FIG. 1F, the patient platform 1000 of FIG. 1A positioning a patient between the arms of imager 21 in accordance with an example implementation. The patient platform 1000 is again using at least one sensor 35 to track and monitor the orientation of the patient platform 1000 that is displayed and controlled by controller 36. Turning to FIG. 1G, the patient platform 1002 is depicted as being placed through another imager 30 using sensors 35 and controller 36 to control the orientation of the patient platform 1002 in accordance with an example implementation.

In FIG. 2A, a radiolucent joint 1 with one degree of freedom that may be used in the center joint of the patient platform 1000, 1002, 1003 is depicted in accordance with an example implementation. The radiolucent joint 1 is made up of two members identified as 1A on either side of member 1B. The radiolucent members formed from radiolucent laminar sheeting, having variable angular articulation, and further including a buttress member including a buttress planar portion; an anatomic support member including an anatomic planar portion. A radiolucent pin or pivot point connector (on-metallic) 1C couples the members together, such that they are able to move and flex as depicted in views "A"-"D." The member 1A is a buttress members/female members made from radiolucent laminar sheeting. Member 1B is an anatomic support member/male member made from radiolucent sheeting. The radiolucent joint 1 can be positioned in an "A" position, "B" position, "C" position. The joint 1 may also be reversed from the "B" position as depicted in view "D."

Turning to FIG. 2B, a radiolucent joint 2 with one degree of freedom that may be used in the center joint of the patient platform 1000, 1002, 1003 is depicted in accordance with an example implementation. Two radiolucent members identified as members 2A are dispersed or interweaved between two other radiolucent members identified as members 2B and coupled together by a radiolucent connector pin (non-metal or non-ferrous metal), such that the resulting joint is moveable as depicted in views "A"-"D" of FIG. 2. Other alternate embodiments may comprise a multiplication of the approach of interlocking male and female laminar sheets via an arrangement of any number of said articulating joints working in tandem and varying sizes and arrangements so that these interlocking joints might be arranged side by side in the manner of the blades of a threshing machine.

In FIG. 2C, an illustration of another radiolucent joint 3 that may be used in the center joint of the patient platform 1000, 1002, 1003 in accordance with an example implementation. The radiolucent joint 3 has the members making up the joint 3 set into each of the members as depicted in 3.1. Each member 3A and 3B is made from a respective one-piece sheet of laminar/planar radiolucent material with a concave arch formed from the radiolucent material. The members are preferably made from radiolucent laminar sheeting. The members 3A and 3B are coupled together with a fastener or other radiolucent (non-metal or non-ferrous metal) connector that secures the members in a rotatable alignment and enables the members to move. Different positions of the radiolucent joint 3 are depicted in views "A"-"D" of FIG. 2C.

Turning to FIGS. 2D-2F, radiolucent laminar buttresses 7 are depicted providing support to members 1A, 1B, 2A, 2B, 3A, and 3C in accordance with an example implementation. A radiolucent laminar lateral buttress adds additional support to the rotatable radiolucent joints 1, 2, and 3 of FIGS. 2A-2C and aids in preventing horizontal sway from lateral shear forces.

In FIG. 3A-3F are similar to FIGS. 2A-2F, depicting a rotatable joint 4, 5, 6 made from radiolucent laminar sheeting 4A, 4B, 5A, 5B, 6A, and 6B, each with removable radiolucent pin 4C, 5C, and 6C that enable the respective joints to move and in a respective position "A"-"D" of FIGS. 3A-3C in accordance with an example implementation. The radiolucent removable non-metallic pin 4C, 5C, and 6C is a respective pivot connection point and is secured with a radiolucent removable non-metallic detent clevis pin 4C1, 5C1, and 6C1 in FIGS. 3A-3C, respectively.

Turning to FIG. 4A, an illustration of a bilateral straight-line mechanism (BSLM) that coordinates the mated flexion/extension of yoked laminar members 8B of the radiolucent hinge when configured as radiolucent imaging compatible Patient platform insertable into live magnetic and radiographic medical imaging bores in accordance with an example implementation. A central pivot point 0 at the intersection of medial vertical straight line 000 and horizontal line 0000 around which yoked radiolucent laminar members 8B rotate in the fixed rotational center modality of usage of the BSLM.

Line 00 is a laterally positioned vertical straight line that is a design parameter around which depicts the degree of movement of part of the BSLM. The vertical straight line 000 at midline bisects the distance between lateral straight lines 00 and 00 located on each side of the BSLM. Horizontal Line 0000 is an axis for the movement of the support of the BSLM.

0L is the lateral pivot point(s) at both sides of the horizontal line 0000 around which lateral yoked radiolucent laminar Members 8B rotate in the vertically rising/descending rotational center modality of usage of the BLSM. 7A is a diagrammatic depiction of length expressed as 6.28318 diameters of the planetary gear 8D. A 240 Tooth Vertical Rack 8K is 6.28318 PGD (Planetary gear Diameters) in length in the current example. As such, 240 Tooth vertical rack 8K is 7A in length.

A diagrammatic depiction of length 7A1 expressed as 3.14 diameters of the planetary gear 8D is shown. A 120 tooth vertical rack comprised of 1001DA and 1001DB is 3.14 PGD in length. As such, 120 tooth vertical rack comprised of 1001DA and 1001DB in FIG. 4A is 7A1 in length. As described, exact lengths are dependent upon the size of the gears and teeth rations. But, a person of skill in the art would recognize these dependencies.

A diagrammatic depiction of length 7A2 is expressed as one full rotation of bifurcated 120 tooth gear 8ER, which is equivalent in length to 3.14 diameters in the length of the planetary gear 8D, or 3.14 PGD in length. As such, 120 tooth vertical rack comprised of 1001DA and 1001DB is 7A2 in length and is depicted showing ONE rotation of bifurcated 60 toothed upper and parallel 60 toothed lower outermost gear 8ER.

A diagrammatic depiction of length 7B expressed as 2 Full Rotations of 120 Tooth gear 8E, equivalent in length to 6.28318 diameters in the length of the planetary gear 8D, or 6.28318 PGD in length. As such, 240 tooth vertical rack 8K is 7B in length.

Seventy-two degree bounded continuum has 72 degrees of angulation results in a corresponding seventy-two degrees of rotation of the planetary gear 8D, or, can be expressed as equaling a $\frac{1}{5}^{th}$ rotation of the planetary gear 8D in a planetary gearbox to achieve the full spectrum of angulation available within this seventy-two degree bounded continuum 72, said spectrum expressed to include angulations from the zero degree horizontal 0000 orientation upwards to 36 degrees of inclination, and as declination from the zero degree horizontal orientation downwards to a 36-degree declivity, with all of the angular orientations in-between. (72 degrees is exactly $\frac{1}{5}^{th}$ of the 360 degrees of rotation available). They are also depicted as item 72 in FIGS. 6D and 6E.

PGD Planetary Gear Diameter is a diagrammatic depiction of ONE DIAMETER in Length of Planetary Gear 8D used as a unit of measure. (One of the Initial Design Parameters around which were Conceptualized and Designed the BSLM). PI is a mathematical term with an approximate value of 3.14. R12TU is rotation of annulus/ring 8D3 at a distance of 12 gear teeth upwards from the horizontal line 0000. RHS is the rotation of annulus/ring 8D3 to the horizontal setting at horizontal line 0000. R12TD is the rotation of annulus/ring 8D3 and is a distance of 12 gear teeth downward from the horizontal line 0000.

The outer rotational housing for the scotch yoke mechanism is 8A, configured with 24 gear teeth to enable a $\frac{1}{5}^{th}$ or a 72-degree total range of vertical rotation of the entire housing 8A containing the differential planetary gear assembly 8D with slotted scotch yoke 8B when in mesh with powered 24 toothed gear 8M. The internal translational housing 8A1 has superior and inferior guide rods for the reciprocating linear translation of slotted scotch yoke/radiolucent laminar member 8B within the rotational housing 8A. Slotted scotch yoke/radiolucent Laminar member of the scotch yoke 8B mechanism enabled to piston in and out of rotational housing 8A due to the conversion of the rotational motion of crank 8C and pin/shaft 8C1 into reciprocating translational linear motion via the engagement and circumambulation of the pin 8C1 within the slot of the yoke 8B. The slot of the slotted scotch yoked radiolucent laminar member 8B is 8B.S.

The BSLM 8 is comprised of differential planetary gear 8D and slotted scotch yoke/radiolucent laminar member 8B, The BSLM 8 is a means of coordinating the mated flexion/extension of the imaging compatible radiolucent hinge joint as a flexion/extension patient platform for usage within the magnetic, and radiographic imaging bore, enabled via the conversion of the rotation of the planetary annulus/ring 8D3 of the differential planetary gear 8D into the simultaneous angulation and oscillating linear motion of slotted scotch yokes 8B, such that the yoked first and second radiolucent laminar members 8B automatically and exactly elongate or retract to compensate for the naturally widening or naturally diminishing gap which would normally separate the radiolucent laminar members 8B from being pivotably attached at the radiolucent connection point, in direct proportion to their departure from and return to a horizontal orientation. Arranged as a mirror-imaged pair, BSLM, comprised of planetary differential gearing 8D with incorporated reciprocating slotted scotch yokes/radiolucent laminar members 8B, enable the simultaneous rotational and Reciprocating Translational Linear Motion of the first and second radiolucent laminar members 8B, to coordinate in such a manner that these first and second radiolucent laminar members 8B are enabled to stay connected and mated directly at the radiolucent point of flexion/extension of the radiolucent hinge joint even as the radiolucent hinge joint is articulated from the horizontal into an acute inverted "V" formation, or articulated from the horizontal into a downward "V" formation, or into the anatomical Trendelenburg, the reverse Trendelenburg and even into the lateral Decubitus or Fowler's position as depicted in FIGS. 4B-4D.

The constituent components of the BSLM 8 consisting of the Differential Planetary Gears 8D and Yoked Radiolucent Laminar Members 8B of each iteration 1000, 1001, & 1002 of FIGS. 4E-4G, are identical, and the primary differences from iteration to iteration involve the rotational actuation of the differential planetary gear 8D via either the 10 to 1 Gear Reduction Train 8GT in mesh with either a fixed rack 1000KFR (with fixed rack iteration 1000 in FIGS. 4E-4G) or a rising Rack 1001DA (with Rising Rack iteration 1001 in FIG. 4E-4G) or via the elimination of said gear reduction train 8GT and linear rack entirely in favor of a powered circular rotating rack with 8M to create a controller controlled, such as Microprocessor, application-specific integrated circuit (ASIC), or microcontroller) virtual rack with circular rotating rack iteration 1002 of FIG. 1.

Figure 5B:
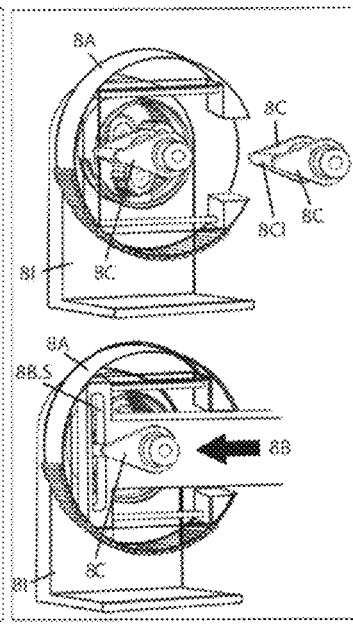
Figure 5C:
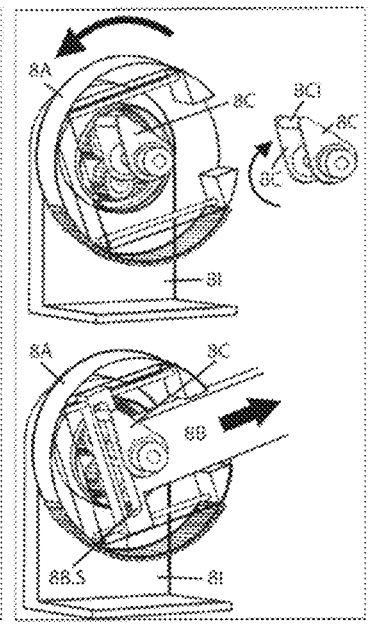
Figure 5D:
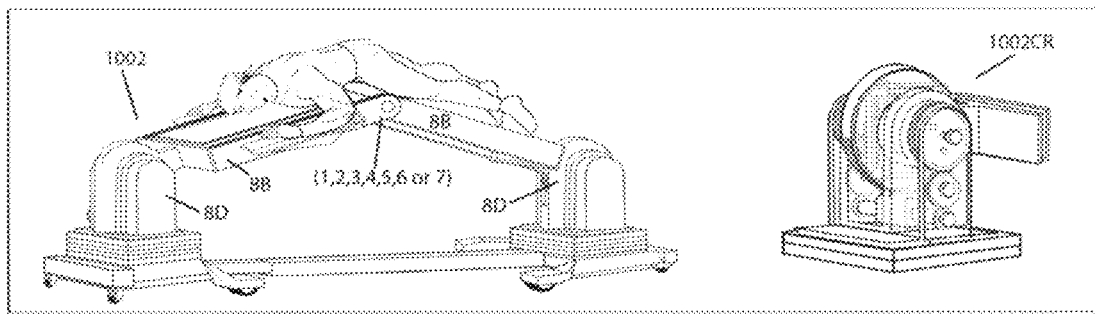
Figure 5E:
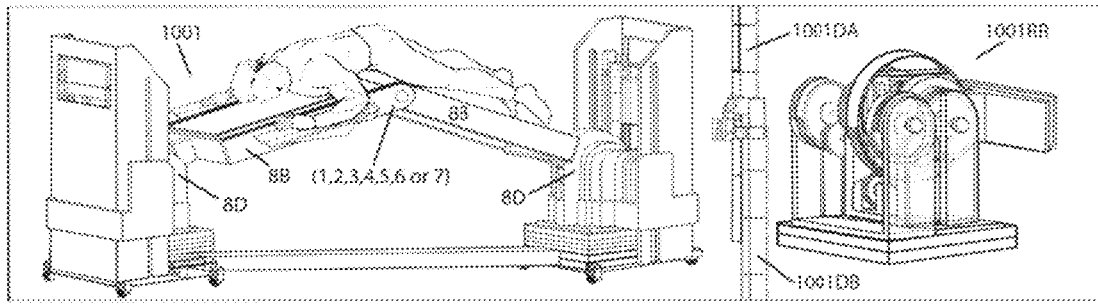
Figure 5F:
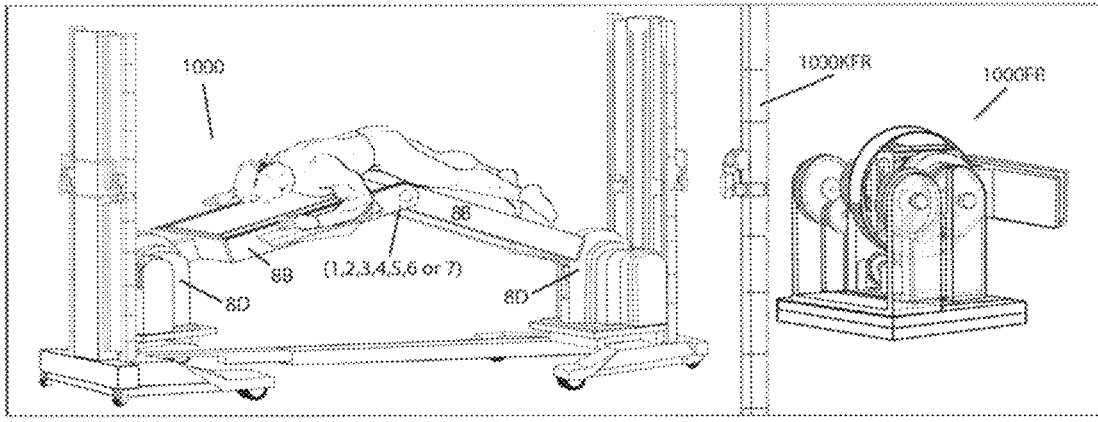

Turning to FIGS. 5A-5F, the operation of the scotch yoke is depicted with the different types of supports 1000, 1001, and 1002 have a depiction of the respective scotch yoke 100FR, 1001RR, and 1002CR in accordance with an example implementation. In FIGS. 5A-5C, vertical rotational swivel mount 8I for vertical rotation of BSLM is shown. Further, in FIG. 5D, the rising rack 1001DA that is part of the vertical rack made up of 1001DA and 1001DB is shown. In FIG. 5E, the single-track vertical rack 1000KFR is depicted. Roller bearings lining the circular rotational fenestrations 8IA (depicted in FIG. 13C) of vertical rotational swivel mount 8I.

In FIGS. 6A-6E, the components of the BSLM 8 are shown in more detail, and its operation is explained in accordance with an example implementation. The outer rotational housing 8A for scotch yoke mechanism, configured with 24 gear teeth to enable a $\frac{1}{5}^{th}$ or a 72-degree total range of vertical rotation of the entire outer rotational housing 8A containing the differential planetary gear assembly 8D with slotted scotch yoke 8B when in mesh with powered 24 toothed gear 8M. (whereas in the present example, vertical rotation of the BSLM 1002CR (FIG. 5D) is driven by the rotation of powered gear 8D6 in mesh with annulus/ring 8D3 of differential planetary gear 8D, and thereby enabling a $\frac{1}{5}^{th}$ or a 72-degree total range of vertical rotation of the entire housing 8A containing the differential planetary gear assembly 8D with slotted scotch yoke 8B. In an alternative embodiment of circular rotating rack iteration 1002, vertical rotation of bilateral straight-line mechanism 1002CR is driven via the same 24 toothed gear 8M of the fixed rack 1000 (FIG. 5F) and rising rack 1001 (FIG. 5E) iterations wherein outer rotational housing 8A is configured with 24 gear teeth to enable a $\frac{1}{5}^{th}$ or a 72-degree total range of vertical rotation of the entire housing 8A containing the differential planetary gear assembly 8D with slotted scotch yoke 8B when in mesh with powered 24 toothed Gear 8M. Internal Translational housing 8A1 with superior and inferior guide rods for the reciprocating linear translation of slotted scotch yoke/radiolucent laminar member 8B within the rotational housing 8A.

As shown in FIGS. 6A-6C, the yoked radiolucent laminar member 8B of the scotch yoke mechanism enabled to piston/move in and out of the rotational housing 8A due to the conversion of the rotational motion of crank 8C and pin/shaft 8C1 into reciprocating translational linear motion via the engagement and circumambulation of the pin 8C1 within the slot of the yoke 8B configurable as a one-piece iteration or as a compound iteration.

Radiolucent laminar member 8B in a one-piece iteration approach has a slotted yoke portion for coupling to differential planetary gear 8D via insertion of pin 8C1 thru slot 8B.S forming a radiolucent hinge. The radiolucent laminar member 8B compound iteration approach also has a slotted yoke portion for coupling to differential planetary gear 8D via insertion of pin 8C1 thru slot 8B.S, and consisting of a separate radiolucent laminar member 8B2 (see FIG. 22F), a separate slotted yoke portion 8B (which may be constructed of non-ferromagnetic metal) and a separate (which may be constructed of non-ferromagnetic metal) bracket portion 8B1 for mounting separate radiolucent laminar member 8B2.

A summary of the elements follows:

8B Slotted Yoke portion for COUPLING to Differential Planetary Gear 8D VIA Insertion of PIN 8C1 thru SLOT 8B.S.

8B2 Radiolucent Laminar Member Portions which FORM the Radiolucent Hinge.

8B1 U-Shaped Mounting Bracket Portion.

8B.S SLOT in Slotted Yoke in the Slotted Yoke portion for COUPLING to Differential Planetary Gear 8D VIA Insertion of PIN 8C1 thru SLOT 8B.S Radiolucent Laminar Member 8B of the slotted scotch yoke mechanism is enabled to piston in and out of rotational housing 8A due to the conversion of the rotational motion of crank 8C and pin/shaft 8C1 into reciprocating translational linear motion via the engagement and circumambulation of the pin 8C1 within the slot of the yoke when coupled via the insertion of pin 8C1 thru slot 8B.S. Rotational crank 8C is driven by the circumferential travel of the 15 toothed sun gear 8D1 of Differential Planetary Gear 8D (also the point of coupling of the slotted sliding yoke 8B and the differential planetary Gear 8D).

Pin 8C1 coupling differential planetary gear 8D to slotted scotch yoked radiolucent laminar member 8B via insertion of pin 8C1 through slot 8BS of the slotted scotch yoked radiolucent laminar member 8B for purposes of converting the rotation of crank 8C sun and gear 8D1 into the reciprocating linear motion of slotted Sliding yoke 8B via engagement with and circumambulation within the slot of the sliding yoke 8B, with the result that the slotted sliding yoke is made to translate with a reciprocating linear motion within rotational housing 8A as crank 8C rotates (also the point of coupling of the slotted sliding yoke 8B and the Differential planetary Gear 8D).

Turning to FIGS. 7A-7E, depict component diagrams of the gear orientation of the BSLM in accordance with an example implementation. The individual parts can be seen in a cut-away view. In FIGS. 8A-8M, the differential planetary gear 8D coupled with the slotted scotch yoked radiolucent laminar member 8B is depicted in accordance with an example implementation.

Turning to FIGS. 9A-9M is another depiction of the operation of the differential planetary gear 8D coupled with the slotted scotch yoked radiolucent laminar member 8B in accordance with an example implementation. In FIGS. 10A-10E, the operation of the differential planetary gear 8D coupled with the slotted scotch yoked radiolucent laminar member 8B show the translation of circular motion to in and out motion in accordance with an example implementation.

Figure 12A:
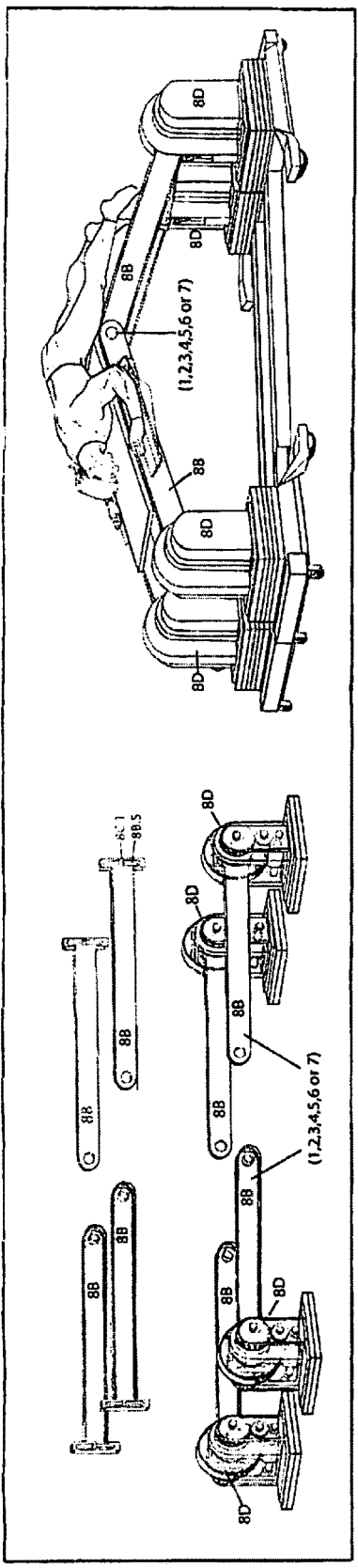
FIGS. 12A-12C are illustrations of additional approaches to forming the patient supports using two or more differential planetary gears 8D in accordance with an example implementation.
Figure 12B:
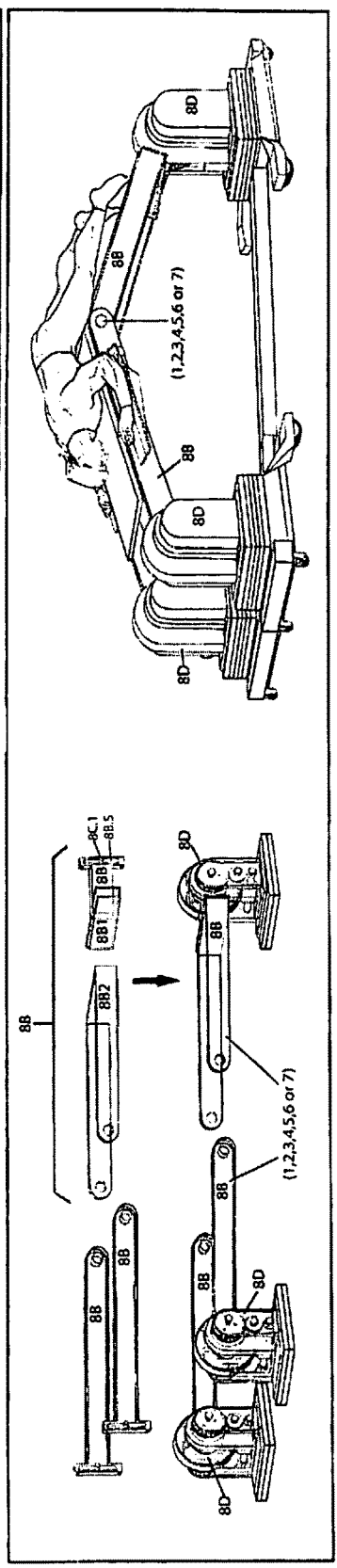
Figure 12C:
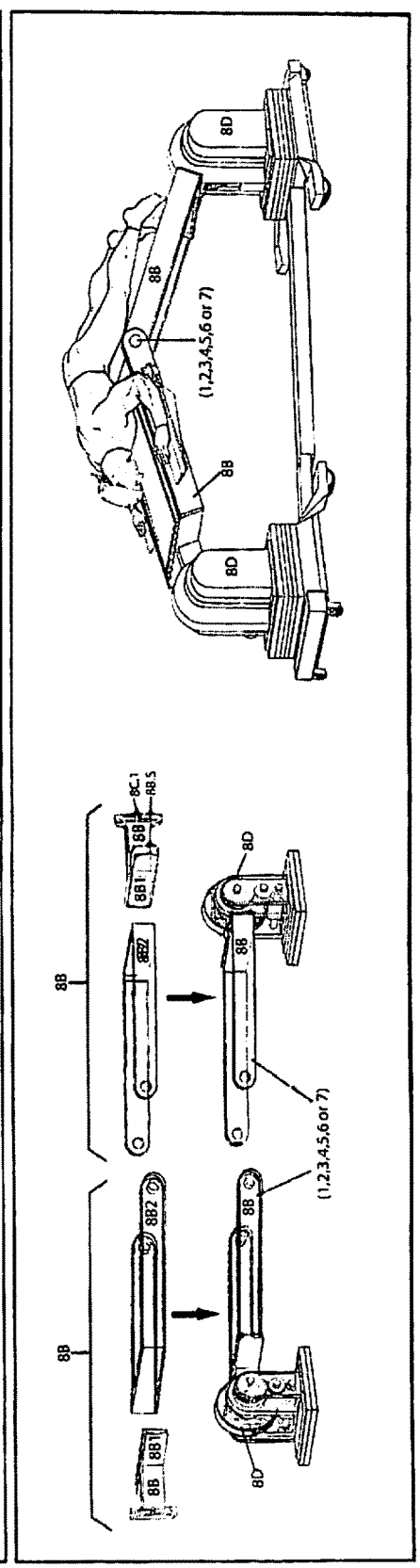
Figure 25B:
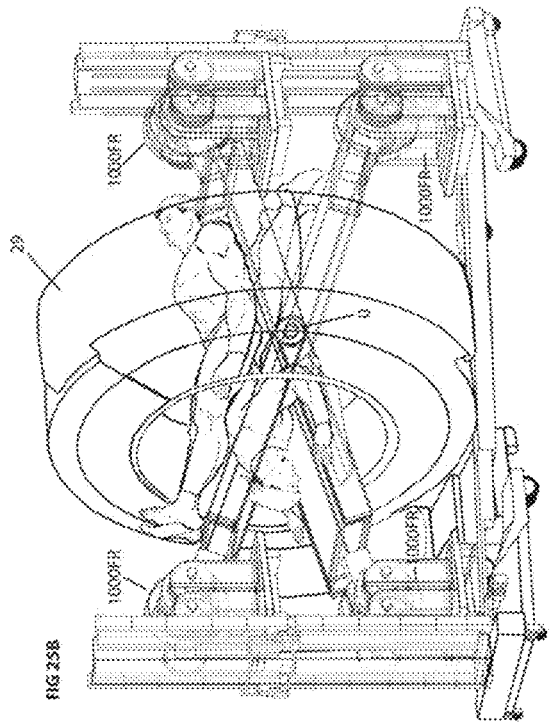
Figure 25D:
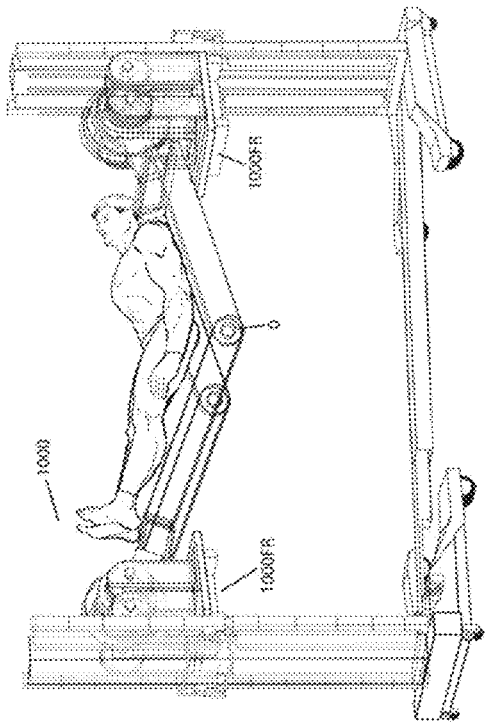
Figure 25A:
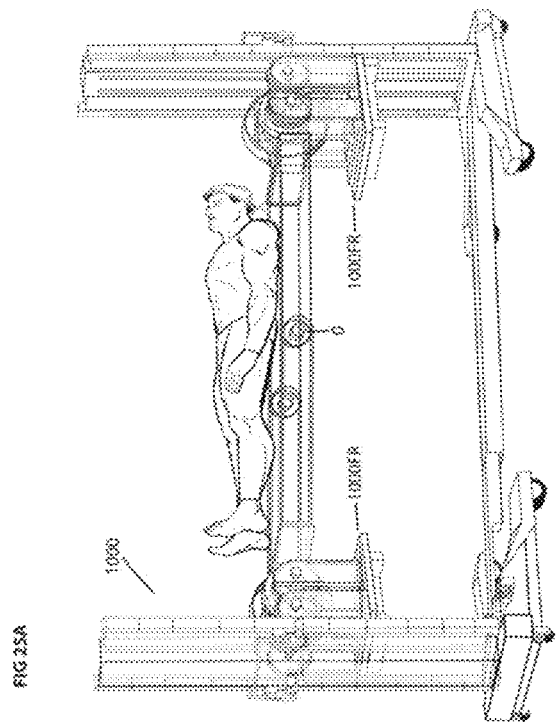
Figure 25C:
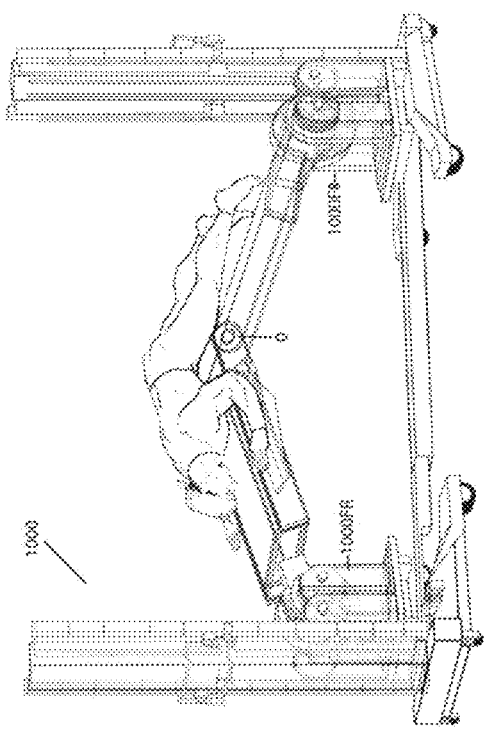
Figure 26B:
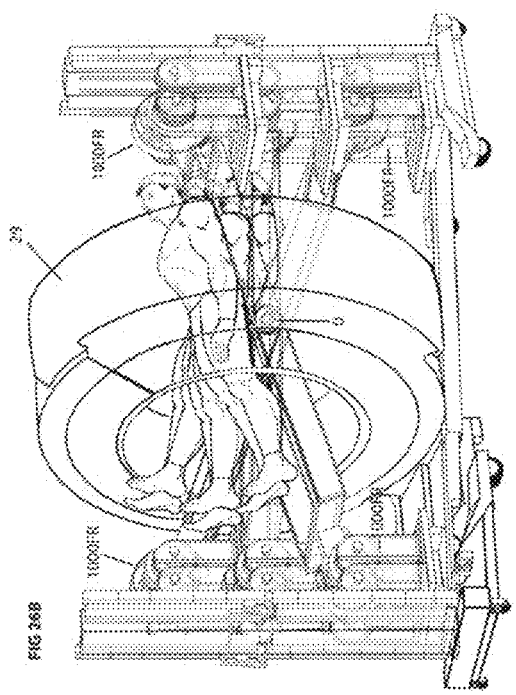
Figure 26D:
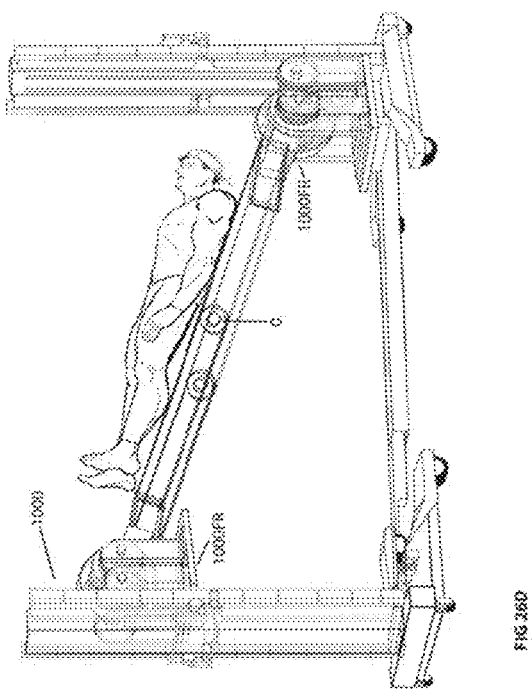
Figure 26A:
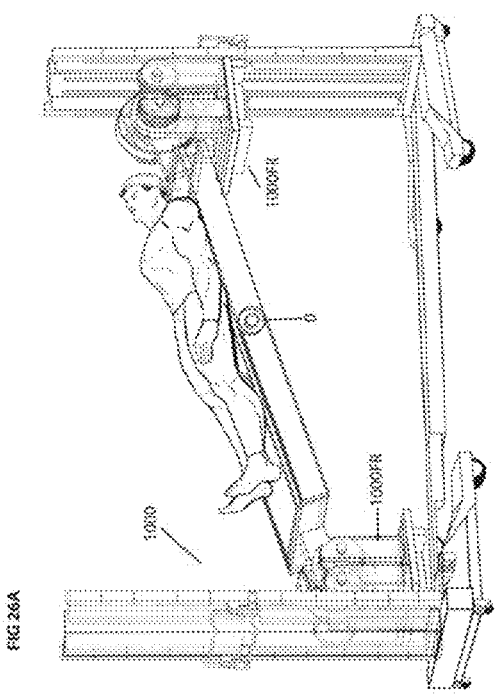
Figure 26C:
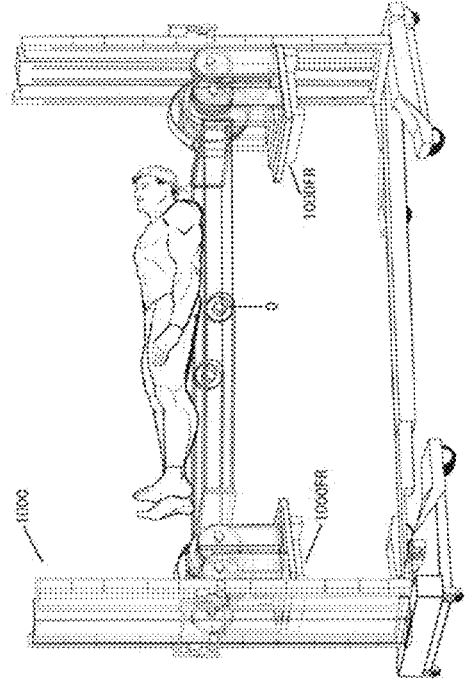
Figure 28B:
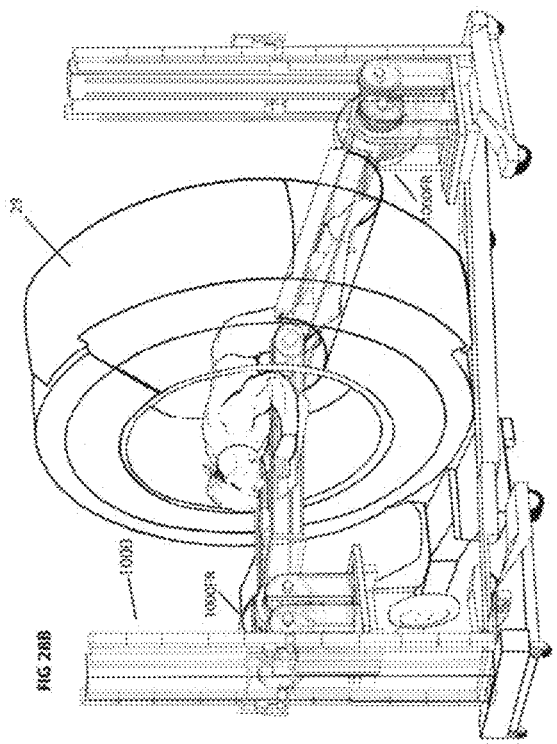
Figure 28D:
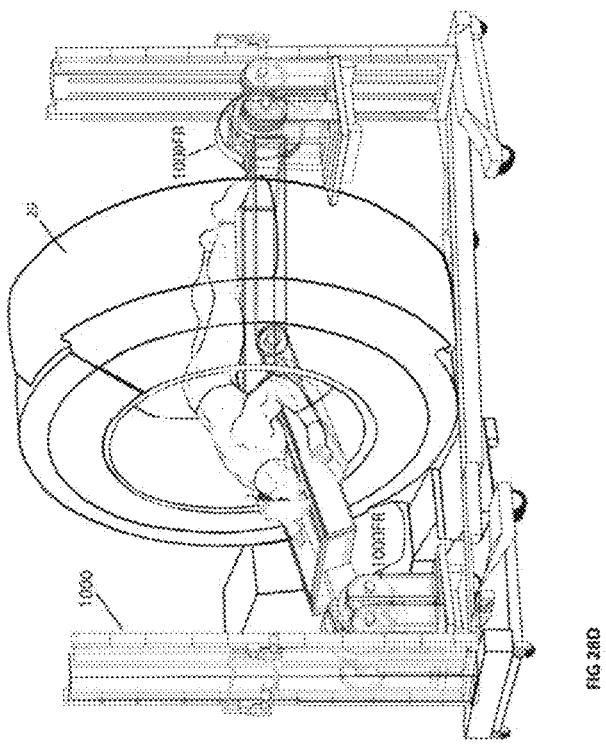
Figure 28B:
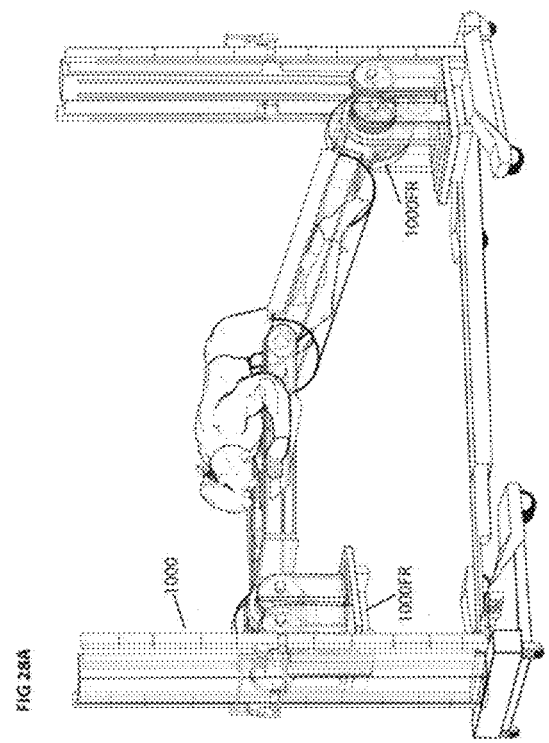
Figure 28C:
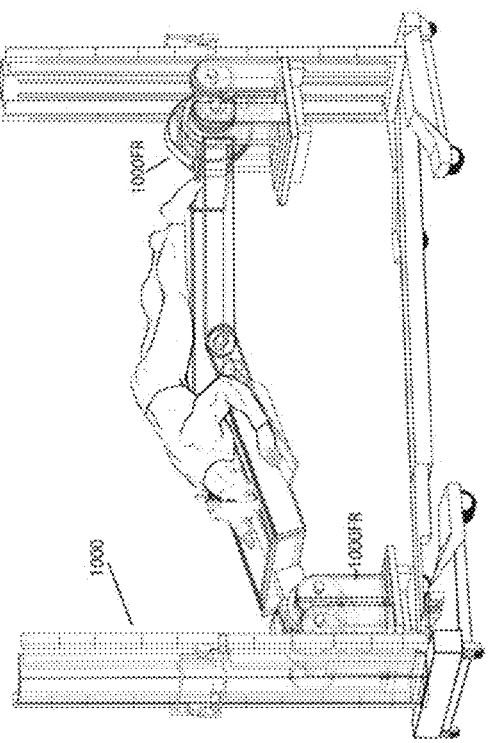
Figure 36A:
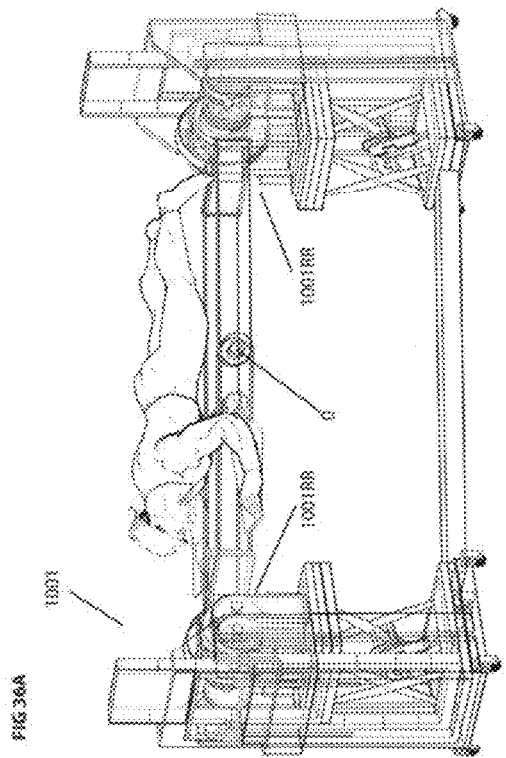
Figure 36B:
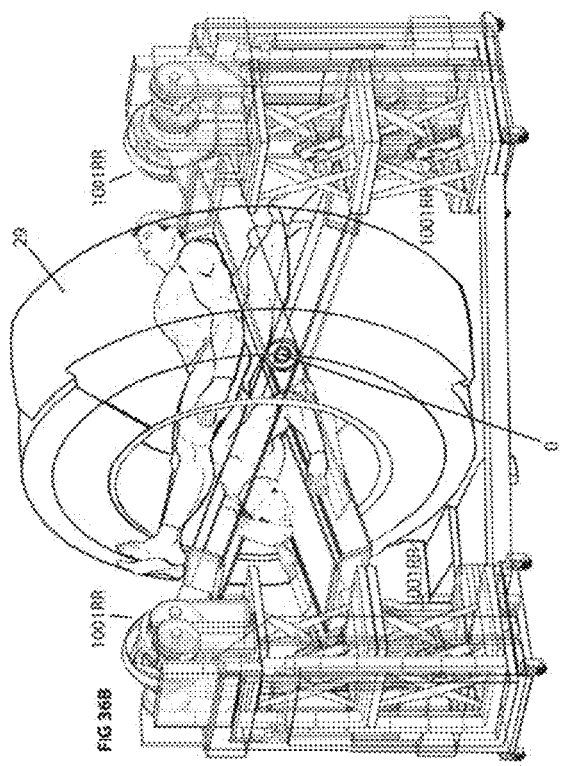
Figure 36C:
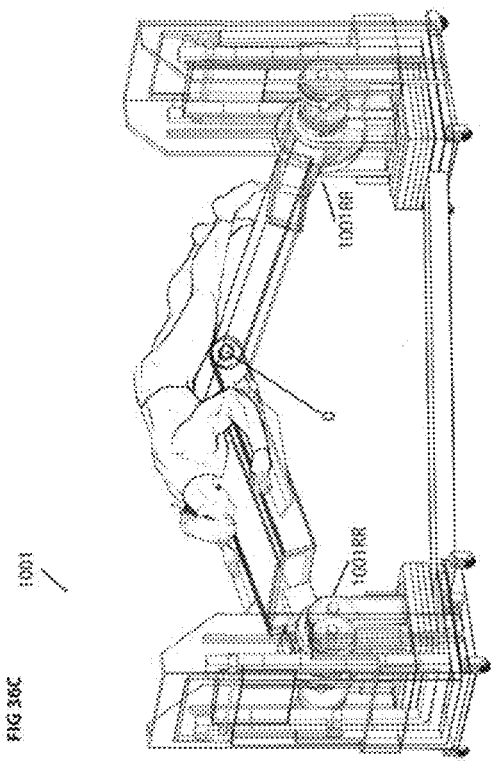
Figure 36D:
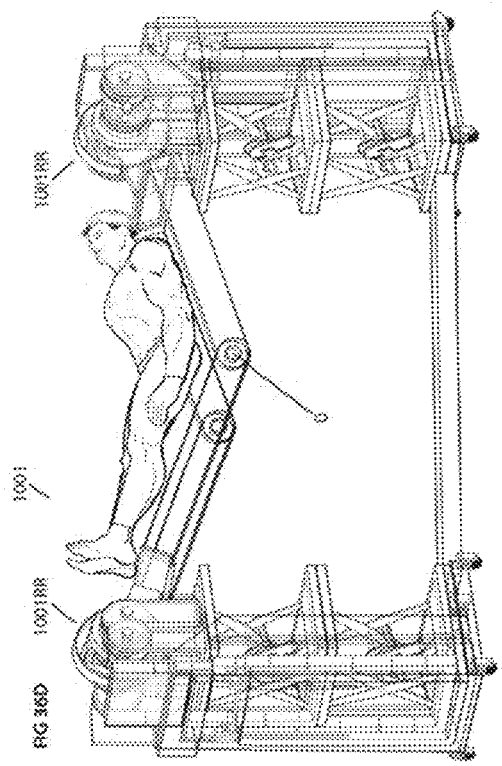
Figure 38B:
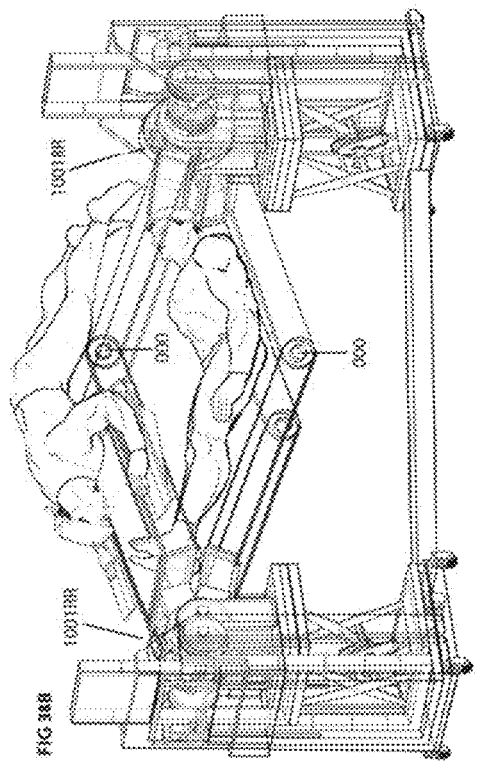
Figure 38D:
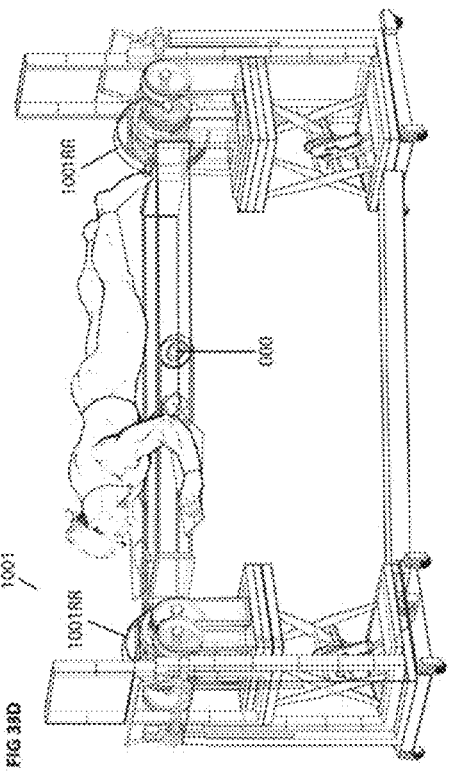
Figure 38A:
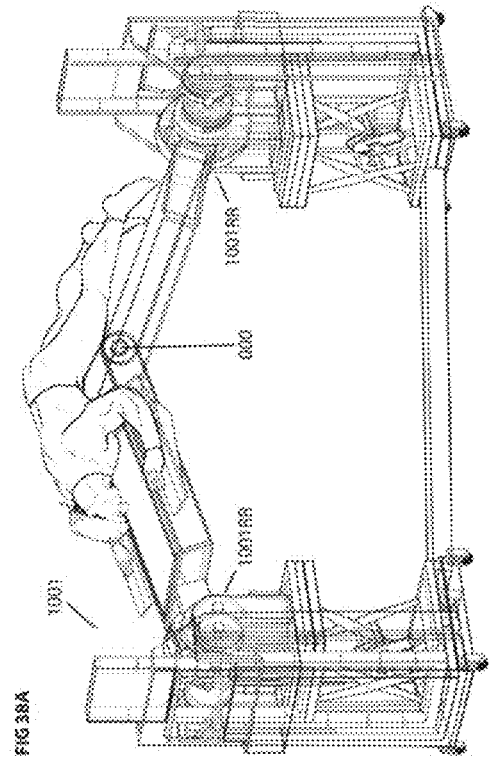
Figure 38C:
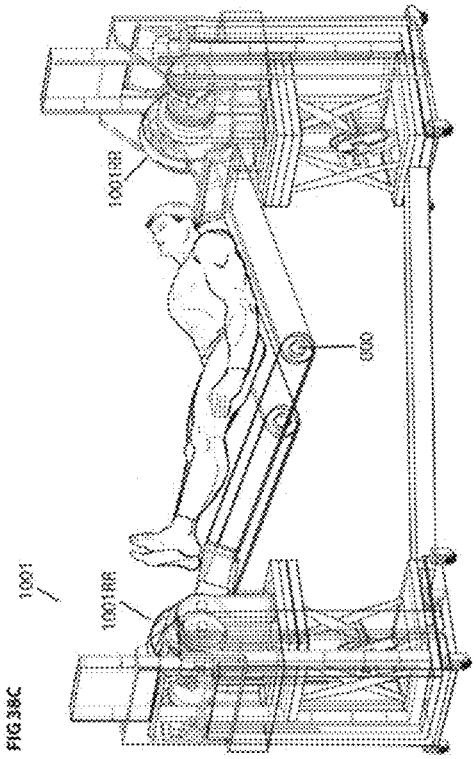
Figure 39A:
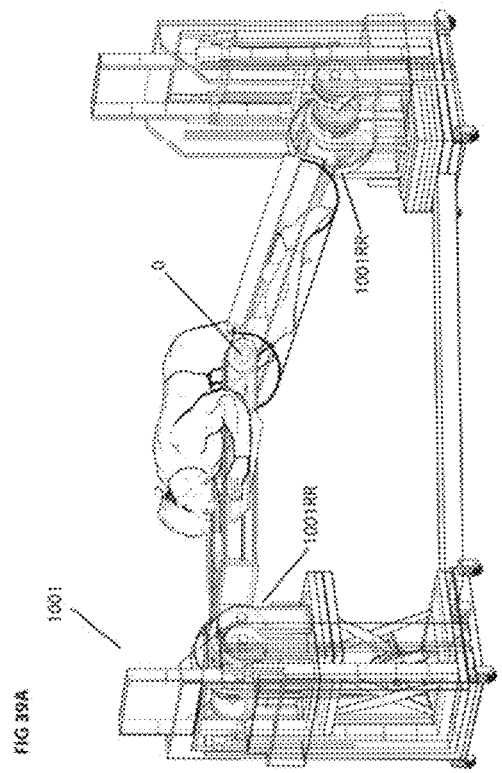
Figure 39B:
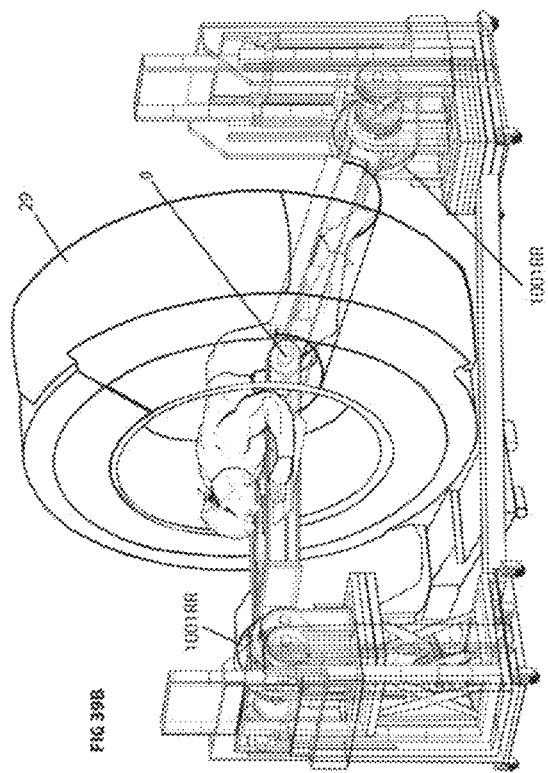
Figure 39C:
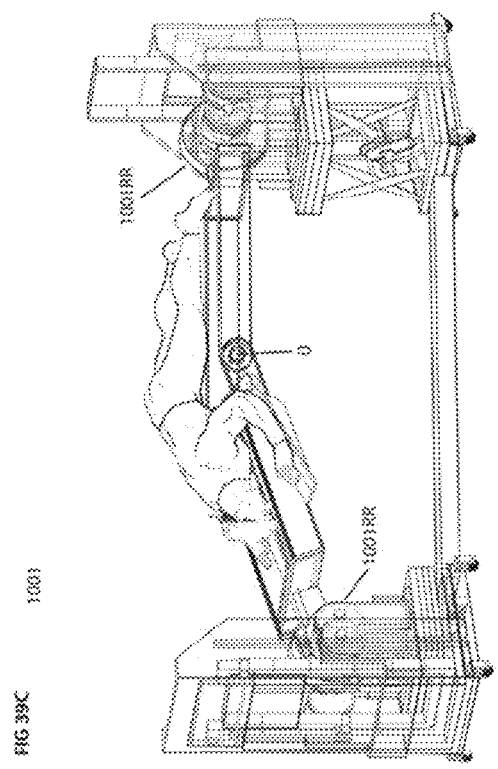
Figure 39D:
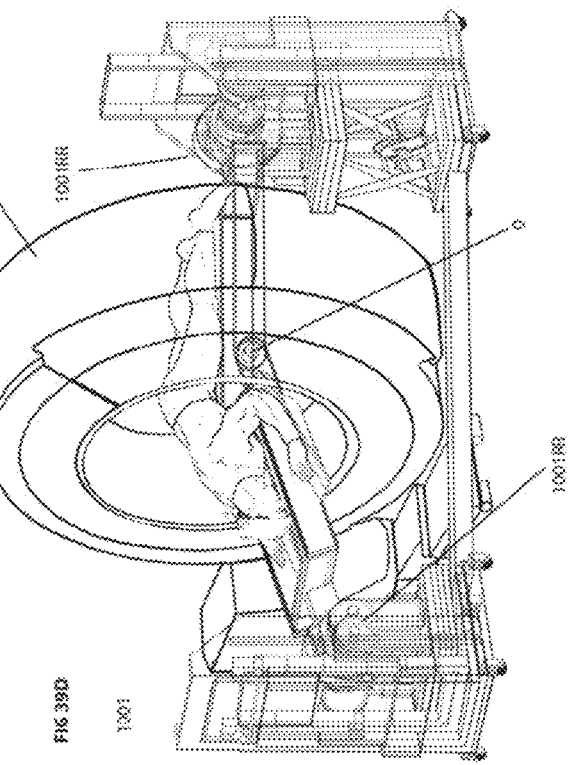
Figure 41A:
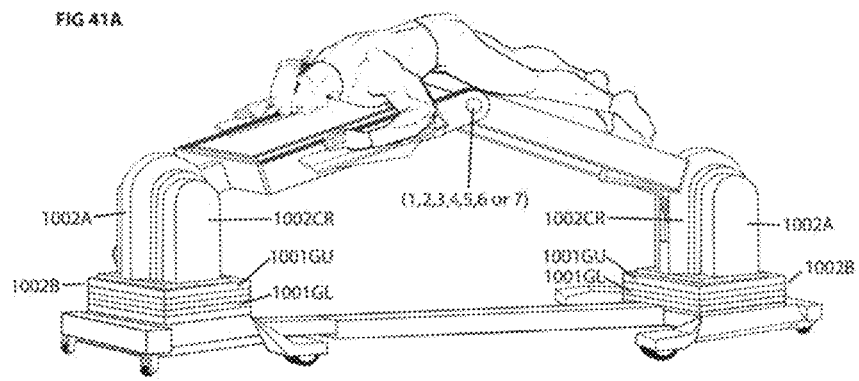
Figure 41B:
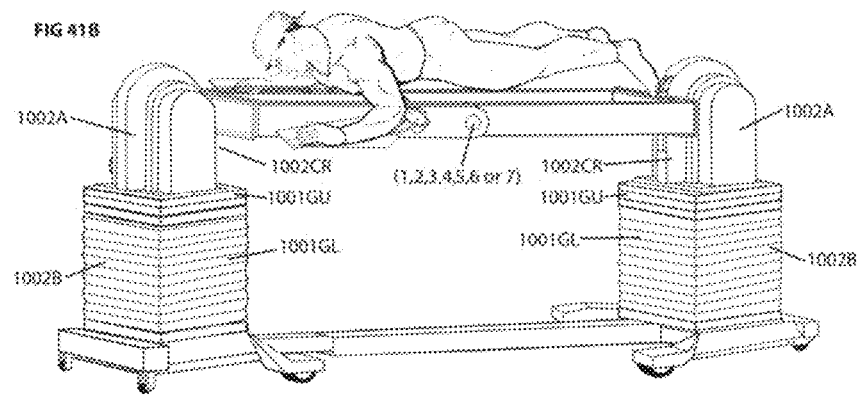
Figure 41C:
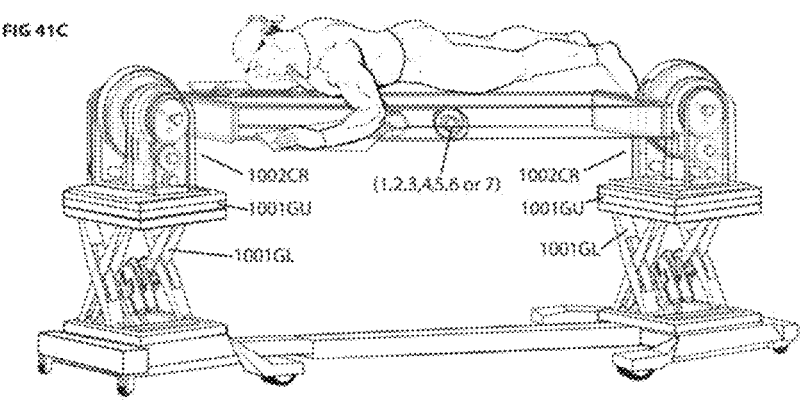
Figure 41D:
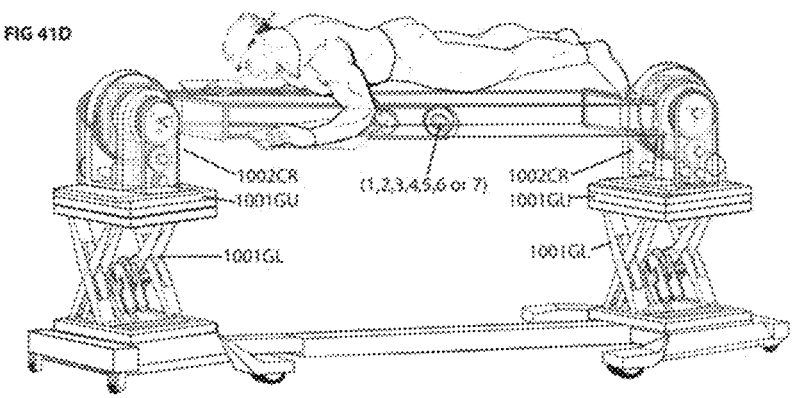
Figure 51A:
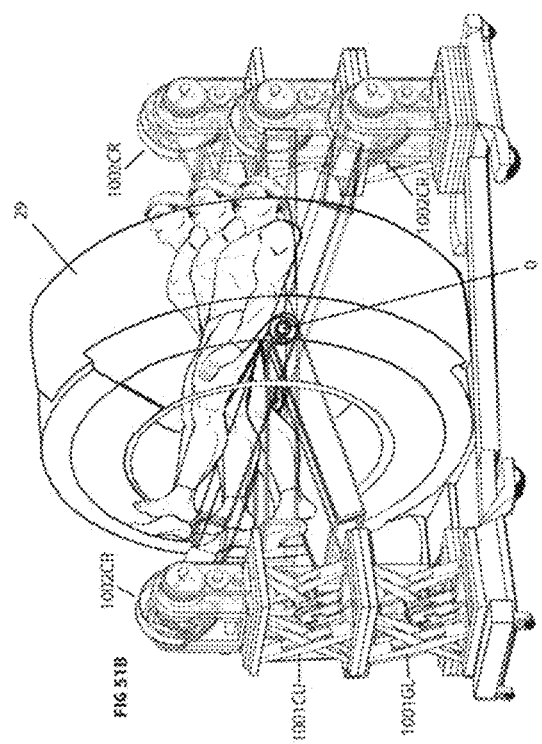
Figure 51B:
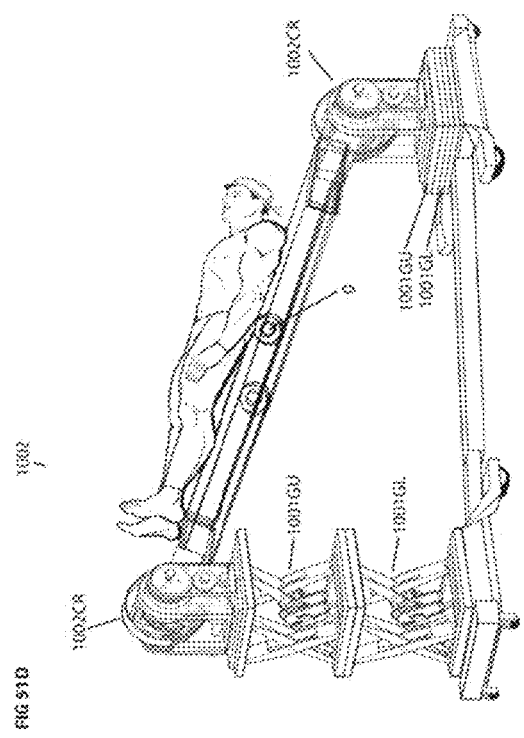
Figure 51C:
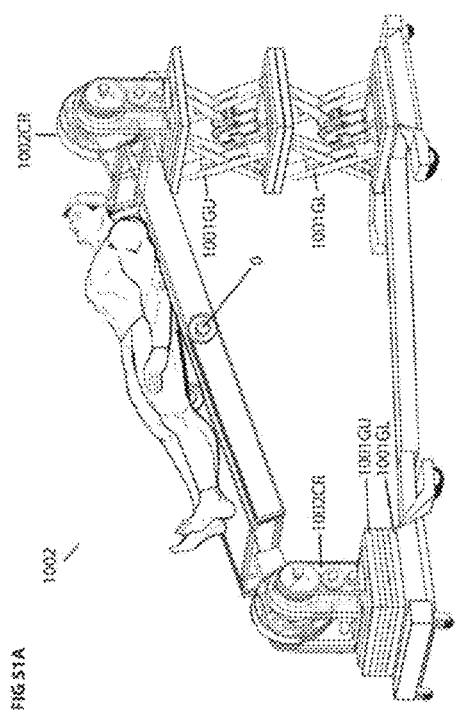
Figure 51D:
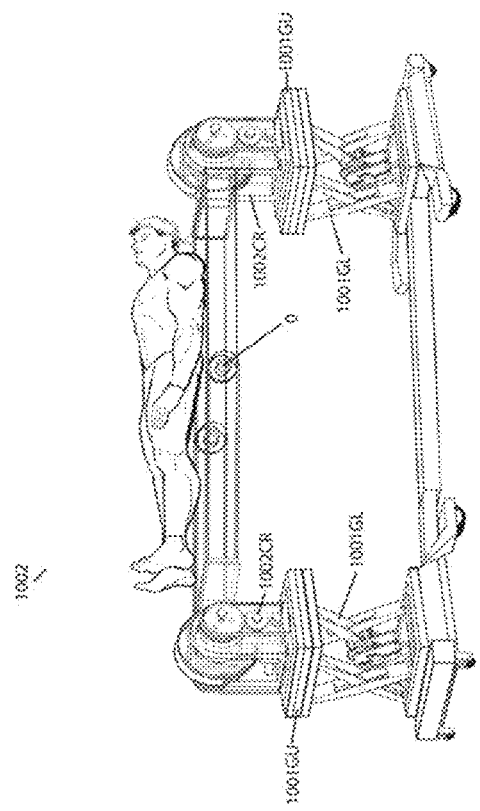
Figure 53A:
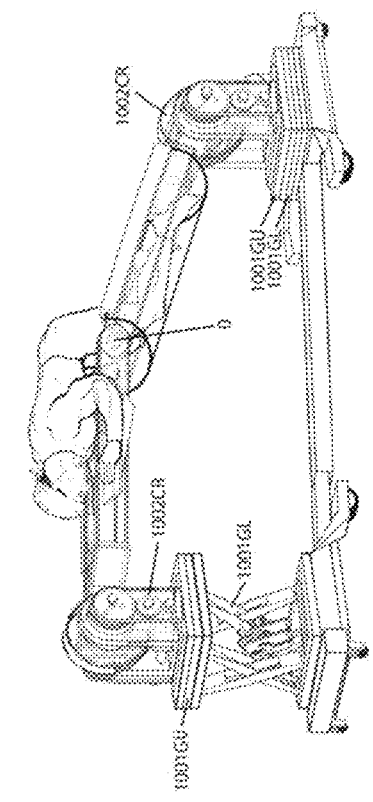
Figure 53B:
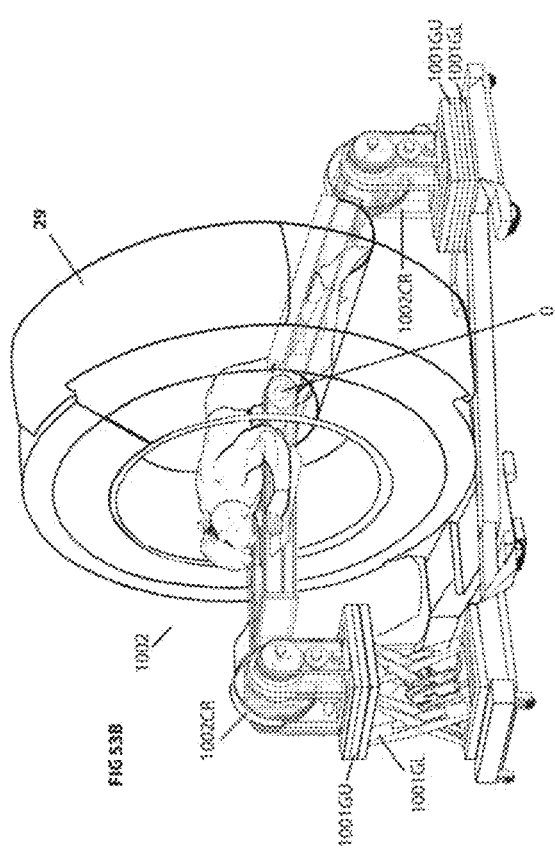
Figure 53C:
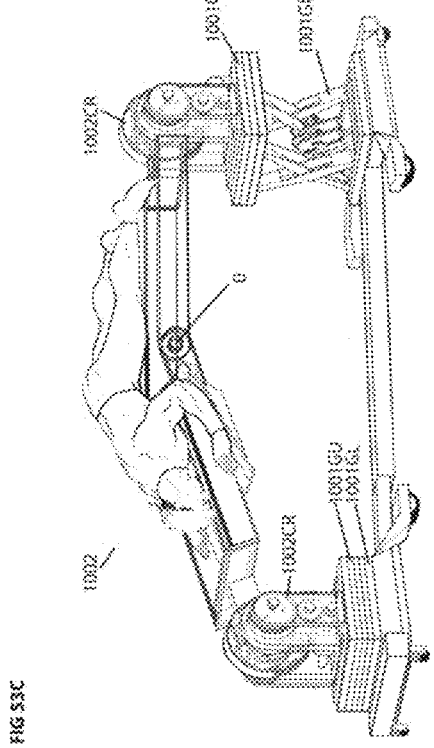
Figure 53D:
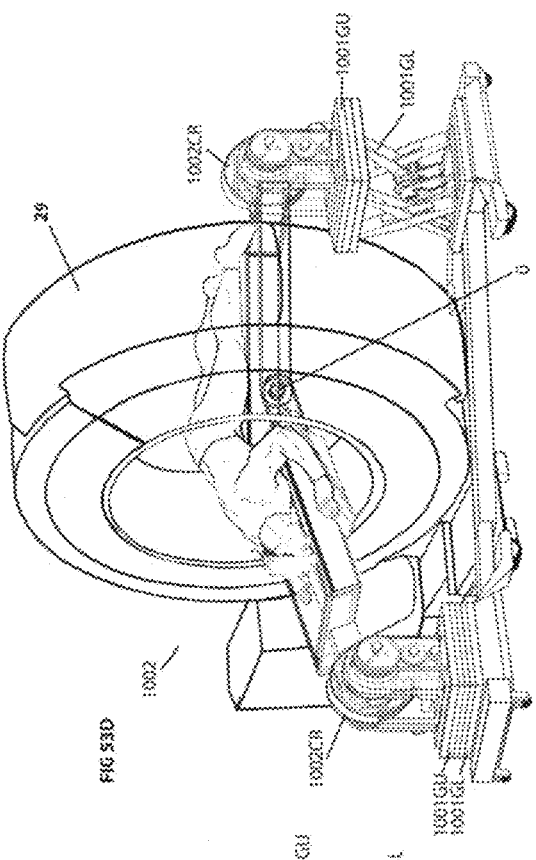
Figure 55A:
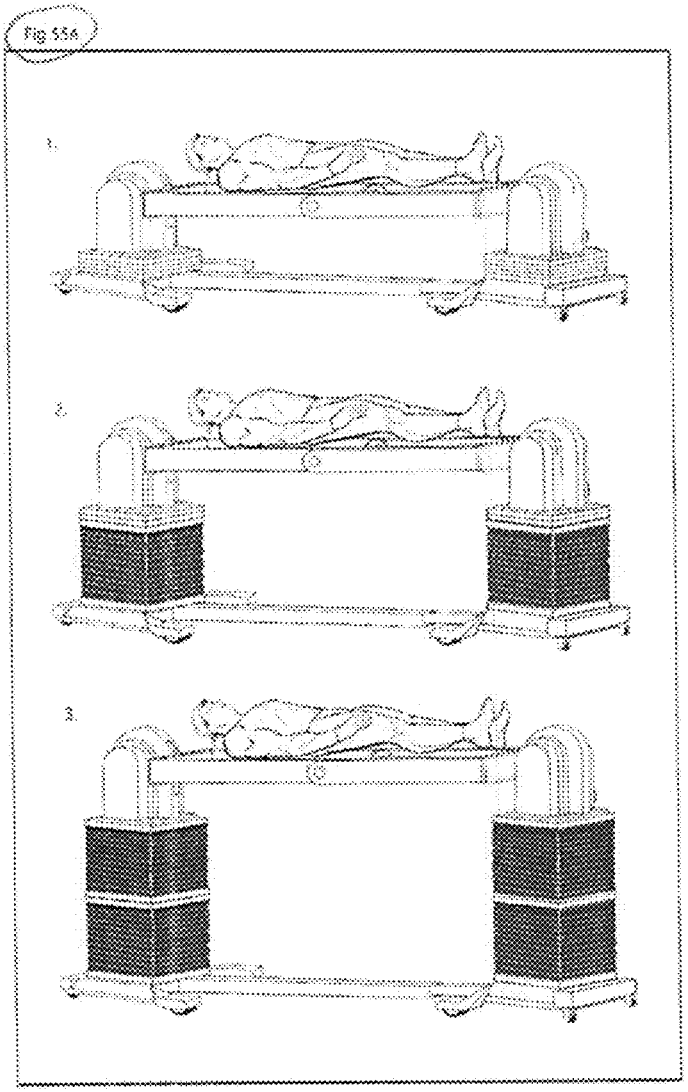
Figure 55B:
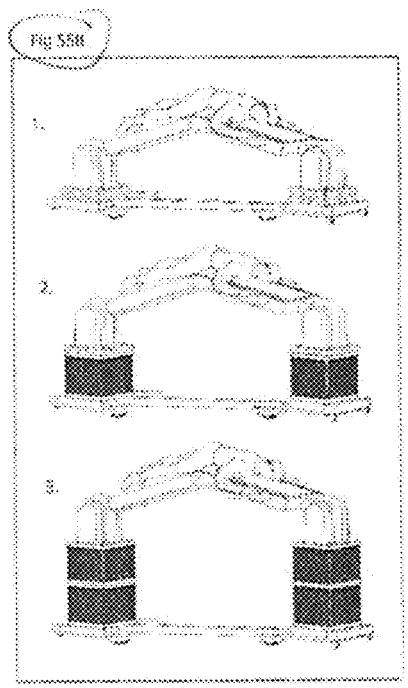
Figure 55C:
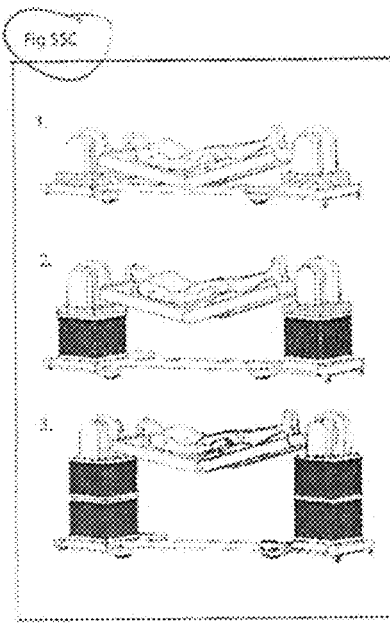

Turning to FIGS. 11A-11E, yet more depictions of the operation of the BSLM with the differential planetary gear 8D coupled with the slotted scotch yoked radiolucent laminar member 8B show the translation of circular motion to in and out motion in accordance with an example implementation. In FIGS. 12A-12C, illustrations of additional approaches to forming the patient supports using two or more differential planetary gears 8D are depicted in accordance with an example implementation. Turning to FIGS. 13A-13L, further depictions of the components of the patient support of FIG. 12C employing differential planetary gears 8D are provided in accordance with an implementation of the invention.

Circular rack gear train 8CRGT utilized with circular rotating rack iteration 1002 (FIG. 5D), comprised of the following Constituent Components . . .

8D6 24 toothed gear powered by motor 8P.

8D61 axel for 24 toothed gear 8D6.

8D5 48 toothed idler gear.

8D5 axel for 48 toothed idler gear 8D5.

8N mount for circular rack gear train 8CRGT.

The differential planetary Gear 8D, is a specialized planetary gear with no stationary elements, necessitating that in addition to the annulus/ring 8D3 and the sun gear 8D1 rotates freely, and the planets 8D2 and planet carrier 8D4 are also enabled to orbit the sun in the same direction as the travel of the annulus/ring 8D3 (as opposed to remaining Stationary) with the resulting "precession" of these planets 8D4 (precession noun/the slow and continuous change in the rotation (i.e. movement around a fixed point) of a planet, star, etc. that is spinning around another planet, star_, etc.) serving as an integral element enabling continuous bilateral straight line functionality across the entire seventy-two degree range of angulation 72.

Differential Planetary Gear 8D is comprised of the following constituent components:

8D1 Sun Gear with 15 Teeth.

8D2 Planet Gear(s) with 52 Teeth.

8D3 Annulus/Ring Gear with 120 external teeth and 120 internal teeth, said internal teeth set and said external teeth sets positioned lateral to one another and separated by a solid offset so that the internal 120 toothed and the external 120 toothed sets have the exact same circumference and therefore transmit exactly equivalent degrees of rotation from gears in mesh with the external set to gears in mesh with the internal set, and vice versa. As such, the diameter and circumference of 120 toothed gear 8D3 is also equal to the diameter and circumference of 120 toothed gear 8E of gear train 8GT.

8D4 Planet Carrier.

8D41 Axel for planet carrier 8D4.

8D4A Planet carrier rods attached to planet carrier for planet gear(s) with 52 teeth.

8I Vertical rotational swivel mount for vertical rotation of BSLM 8.

8IA Roller bearings lining the circular rotational fenestrations of vertical rotational swivel mount 8

8A Outer rotational housing for scotch yoke mechanism, configured with 24 gear teeth to enable a $\frac{1}{5}^{th}$ or a seventy-two degree total range of vertical rotation of the entire housing 8A containing the differential planetary gear assembly 8D with slotted scotch yoke 8B when in mesh with powered 24 toothed gear 8M.

8A1 Internal translational housing with superior and inferior guide rods for the reciprocating linear translation of slotted scotch yoke/radiolucent laminar member 8B within the rotational housing 8A.

8D1 Sun gear with 15 teeth.

8D2 Planet gear(s) with 52 teeth.

8D3 Annulus/ring gear with 120 external teeth and 120 internal teeth, said internal teeth set and said external teeth sets positioned lateral to one another and separated by a solid offset so that the internal 120 toothed and the external 120 toothed sets have the exact same circumference and therefore transmit exactly equivalent degrees of rotation from gears in mesh with the external set to gears in mesh with the internal set, and vice versa. As such, the diameter and circumference of 120 toothed gear 8D3 is also equal to the diameter and circumference of 120 toothed gear 8E of ear train 8GT.

8D4 Planet carrier.

8D41 Axel for planet carrier 8D4.

8D4A Planet carrier rods attached to planet carrier for planet gear(s) with 52 Teeth.

8D5 48 toothed gear of rotational gear train RGT driven by motorized actuator 8P for vertical rotation of BSLM for circular rack 1002CR.

8D6 24 toothed gear of rotational gear train CRGT driven by motorized actuator 8P for vertical rotation of BSLM for circular rack 1002CR.

8D61 Axel for 24 toothed gear 8D6.

8DN Mount for rotational gear train RGT comprised of gears 8D5 & 8D6.

8E 120 toothed gear "in mesh" with straight rack 8K.

8ER Bifurcated 60 toothed upper and parallel 60 toothed lower outermost gear of rising rack 1001RR.

8E1 Axel for 120 toothed gear 8E.

8F 30 Toothed COMPOUND Gear attached to 120 Tooth Gear 8E.

8F1 Axel for 30 toothed gear 8F.

8G 60 Toothed gear in engagement with 30 tooth gear 8F

8GT Gear train with 10-to-1 reduction when in engagement with 240 tooth gear rack 8K, and configured as a gear reducer to drive differential planetary gear 8D a total of 24 teeth for every 240 tooth movement of 120 toothed gear 8E, when 120 toothed gear 8E is vertically translated in mesh with 240 toothed gear rack 8K. Used with fixed rack table iteration 1000.

Gear Train 8GT is comprised of the Following Constituent Component:

8E 120 toothed gear (of the 10-to-1 reduction gear train 8GT) "in mesh" with straight rack 8K.

8E1 Axel for 120 toothed gear 8E.

8F 30 toothed compound gear attached to 120 tooth gear 8E.

8F1 Axel for 30 toothed gear 8F.

8G 60 Toothed gear in engagement with 30 tooth gear 8F.

8H 24 Toothed Idler Gear in engagement with Planetary Gear 8D.

8J Gear train mount for 10-to-1 reduction gear train 8GT.

8M Powered 24 tooth Gear for Vertical Rotation of Outer Rotational Housing 8A.

8I Vertical rotational swivel mount for vertical rotation of BSLM.

8IA Roller bearings lining the circular rotational fenestrations of vertical rotational swivel mount 8I.

8J Gear train mount for 10 to 1 reduction gear train 8GT.

8K The 240 tooth vertical rack 8K allows for two entire rotations of the 120 tooth gear 8E across the Entire 240 Tooth Vertical Rack 8K or also Enables ONE Full 120 tooth rotation upwards from the exact centerline 0000 of the 240 tooth vertical rack, and one full rotation downwards from the exact centerline 0000 of the 240 tooth vertical rack 8K. (1000KFR is the fixed rack iteration of the 240 tooth vertical rack 8K used with table 1000, whereas 1001DA, and 1001DB are the rising rack iterations of the vertical rack 8K used with patient table 1001.)

8M Winch/powered gear 8M in engagement with 24 toothed portion of outer rotational housing 8A. (powered gear 8M is utilized only in the vertically rising/descending rotational center modality when the planetary gear has been taken out of mesh with the fixed rack. In the fixed rotational center modality, the powered gear 8M is placed in a "Free Spin" modality without power and cannot be powered until planetary gear 8D is stationary at horizontal line 0000)

8P Motorized actuator of 24 toothed gear 8D6 of the rotational gear train (RGT) for vertical rotation of outer rotational housing 8A.

8Q Vertical rotational swivel mount for vertical rotation of BSLM.

8Q1 Roller bearings lining the circular rotational fenestrations of vertical rotational swivel mount 8I.

In FIG. 14A, a depiction of BSLM with embodiments 1000, 1001, and 1002 where sensor 35 monitors the position of the patient positioner via retro-reflective fiducial markers 34 (which are non-metallic) in accordance with an example implementation. A computer-assisted guidance system 36 for remote manipulation, articulation, position, control, and braking of the movements of the radiolucent image-guided surgical table/patient platform communicates control signals to the patient platform. The communication is either wired or wireless (WIFI, Bluetooth to give but a few examples). The patient platform moves in response to the control signals. It is noted that the controller has a processor, memory, power supply, wired network interface, wireless network interface a (wired or wireless) connection to sensor 35 (serial, parallel, Bluetooth, etc.) connected together via a data/power bus. A display device (touch screen in the example implementation) enables a graphical display of the patient positioner to be displayed. A user simply moves the graphical image, and the patient positioner moves to that position as verified by the fiducial markers 34. FIG. 14B depicts different graphical images 14a-14l that represent the position of the patient platform after a user using the touch screen caused the movement in accordance with an example implementation. The sensor 35 may be an optical or laser tracking array for capturing the motion of the non-metallic fiducial markers 34 within and outside of an imaging bore in the current implementation.

Turning to FIG. 14C, a hand controller 38 may be coupled to the controller 36 or the patient platform by a direct connection or a wireless connection in accordance with an example implementation. The hand controller 38 may have touchscreen or input buttons to control the movement of the patient platform. In some implementations, both hand controller 38 and controller 36 may be employed. The display of the hand controller is able to depict the position of the patient platform as shown in graphical depictions 14m-14y. FIGS. 15A-15C, 16A-16C, 17A-17C, and 18A-1B depict additional examples of the BSLM in accordance with example embodiments. It is noted that controller 36 displays different images 13a-j on the touch screen display coupled to controller 36.

In FIGS. 19A-19C, 20A-20H, 21A-21C, 22A-22L, 23A-23I, 24A-24E, 25A-25D, 26A-26D, 27A-27D, 28A-28D, 29A-29E, illustrations of the patient support and components of the patent support are depicted in accordance with an example implementation.

Turning to FIGS. 30A-30D, 31A-31H, 32A-32C, 33A-33L, 34A-34F, 35A-35F, 36A-36D, 37A-37D, 38A-38D, 39A-39D, illustrations of additional patient support and components of the patent support are depicted.

In FIGS. 40A-40E, 41A-41D, 42A-42H, 43A-43D, 44A-44C, 45A-45F, 46A-46H, 47A-47H, 48A-48I, 49A-49I, 50A-50D, 51A-51D, 52A-52D, 53A-53D, 54A-54E, 55A-55C illustrations of additional patient support and components of the patent support are depicted.

Housing 1000A for fixed rack 1000FR of the BSLM. Vertical superstructure 1000B for 240 toothed fixed vertical rack with internal means of actuation of vertically elevating platform 1000c. (elevating approach operable with pneumatic, hydraulic, electric, or manual actuation via cable, belt, piston, screw-jack, shuttle, pawl and ratchet, crank or any other conventional means of elevation.) Vertically Elevating Platform 1000C which raises and lowers bilateral straight-line mechanism 1000fr and 10-to-1 gear reduction train 8gt in mesh with 240 toothed vertical rack 1000KFR.

Retractable toothed component 1000d of fixed rack table 1000 retractable fixed rack gear tooth portion with control lever. For purposes of clarity of understanding of function, right side retractable fixed rack tooth portion with control lever 1000d is depicted with toothed portion retracted via control lever pulled outwards from the superstructure 1000b, and the left side retractable fixed rack tooth portion is depicted with toothed portion advanced and in line with the teeth of the fixed rack 1000kfr via control lever pushed inwards towards superstructure 1000d. The lever can be configured as lockable and unlockable. toothed portion 1000d is retracted for usage of the bilateral straight-line mechanism 1000fr in the vertically rising/descending rotational center modality, and toothed portion 1000d is advanced in line with the teeth of the fixed rack 1000kfr for usage of the bilateral straight-line mechanism 1000fr in the fixed rotational center modality.

Retractable toothed component 1001d of rising rack table 1001 retractable gear tooth portion of rising rack iteration lower segment with control lever. For purposes of clarity of understanding of function, right side retractable tooth portion with control lever 1001d is depicted with toothed portions retracted via control lever pulled outwards from the superstructure 1000b, and the left side retractable tooth portions is depicted with toothed portions advanced and in line with the teeth of the lower rack portions 1001db via control lever pushed inwards towards superstructure 1001E. The lever can be configured as lockable and unlockable. toothed portion 1001d is retracted for usage of the bilateral straight-line mechanism 1001n in the vertically rising/descending rotational center modality, and toothed portion 1001d is advanced in line with the teeth of the rising rack lower portion 1001db for usage of the bilateral straight-line mechanism 1001rr in the fixed rotational center modality.

1001E outer vertical translation superstructure which guides the vertical translation of upper and lower scissor lifts 1001GL (lower) and 1001GU (upper). Vertical Translation Buttress 1001F elevates and descends in concert with bilateral straight-line mechanism 1001RR while tethering the bilateral straight-line mechanism to the outer vertical translation superstructure 1001e to maintain lateral straight-line functionality. The base for vertical superstructure 1000e1 of 240 toothed fixed rack/left (with non-metallic portions NM for insertion into open MRI bore 32.) Base for vertical superstructure 1000E2 of 240 toothed fixed rack/right (with non-metallic portions nm for insertion into open MRI bore 32) BSLM 1000FR for fixed rack 1000FR.

The fixed rack iteration 1000KFR of the 240 tooth vertical rack 8k used with fixed rack table 1000. The 240 tooth vertical rack 8K allows for 240 entire rotations of the 120 tooth gear 8E across the entire 240 tooth vertical rack 8K or also enables one full 120 tooth rotation upwards from the exact center line 0000 of the 240 tooth vertical rack, and one full rotation downwards from the exact center line 0000 of the 240 tooth vertical rack 8K. The radiolucent flexion/extension spine table rising rack iteration 1001 utilizes the established fixed rack 1000 iteration design parameters, yet reduces the vertical dimensions of the mechanism via bifurcating the fixed rack into a stationary lower rack segment 1001DB and a parallel rising secondary rack segment 1001DA, such that as the bilateral straight line mechanism 1001RR elevates or descends atop lower scissor lift 1001G, it carries the parallel secondary rack segment 1001A with it. In the rising rack 1001 iteration, the planetary gear 8D is nearly identical to the fixed rack planetary gear 8D, with the sole and only Change to the BSLM of the rising rack 1001 iteration (named 1001RR) from the fixed rack BSLM (named 1000FR), being the bifurcation of the upper and lower halves of the 120 toothed gear 8E and the parallel placement of these said resulting 60 toothed upper and 60 toothed lower half mirror imaged toothed gear portions of the resulting outer gear 8ER of the 10-to-1 gear train 8GT, such that the secondary outer gear 8ER is enabled to transition at horizontal line 0000 from Being in mesh with lower rack segment 1001DB to being in mesh with rising secondary rack segment 1001DA as it crosses the moment of equilibrium at horizontal line 0000 as the lower scissor-lift 1001G attains it's maximum height at 0000 and the bilateral straight line mechanism transitions from being in mesh with the lower rack segment 1001DB to being in mesh with the secondary rack segment 1001DA. The above recited transition at the passing thru of the moment of equilibrium at horizontal line 0000 is fully visually depicted on figural page 35 for purposes of clarity of understanding.

Housing 1001A for rising rack 1001RR of a BSLM. Upper Scissor Lift 1001GU is operable with either, pneumatic, hydraulic, electric, or any other conventional means of actuation. The lower scissor lift 1001GL is also operable with either, pneumatic, hydraulic, electric, or any other conventional means of actuation. The upper rising rack segment 1001da, attached to upper scissor lift 1001GU upon which is mounted the rising rack iteration of BSLM 10001RR, such that as the upper scissor lift 1001GU travels vertically, upper rising rack segment 1001DA also travels in unison. The lower fixed vertical rack segment 1001DB with maximum tooth height at horizontal line 0000.

Inner vertical translation superstructure 1001C, upon which is mounted lower scissor lift 1001GL. The inner vertical translation superstructure 1001C is also the translation guide for rising vertical rack segment 1001DA. Retractable gear tooth portion of rising rack iteration lower segment 1001D with control lever. for purposes of clarity of understanding of function, right side retractable tooth portion with control lever 1001D is depicted with toothed portions retracted via control lever pulled outwards from the superstructure 1000B, and the left side retractable tooth portions is depicted with toothed portions advanced and in line with the teeth of the lower rack portions 1001DB via control lever pushed inwards towards superstructure 1001E. The control lever can be configured as lockable and unlockable. The toothed portion 1001D is retracted for usage of the BSLM 1001RR in the vertically rising/descending rotational center modality, and toothed portion 1001D is advanced in line with the teeth of the rising rack lower portion 1001DB for usage of the BSLM 1001RR in the fixed rotational center modality.

The outer vertical translation superstructure 1001E guides the vertical translation of upper and lower scissor lifts 1001GL (lower scissor lift) and 1001GU (upper scissor lift).

The base for scissor lifts left 1001E1 with non-metallic portions NM for insertion into open MRI bore 32. The base for scissor lifts right 1001E2 with non-metallic portions NM for insertion into open MRI Bore 32. The vertical translation buttress 1001F which elevates and descends in concert with BSLM 1001RR while tethering the BSLM to the outer vertical translation superstructure 1001E to maintain lateral straight-line functionality. Upper Scissor Lift 1001GU is operable with either, pneumatic, hydraulic, electric, or any other conventional means of actuation. The lower scissor lift 1001GL is operable with either, pneumatic, hydraulic, electric, or any other conventional means of actuation.

The base for vertical translation superstructure/left is 1001Ha and the base for vertical translation superstructure/right is 1001Hb. Further, the BSLM for the rising rack iteration 10001 is 1001RR.

The circular rotating rack iteration 1002 of the radiolucent hinge when configured as radiolucent, imaging compatible, flexion/extension patient platform-spine table utilizing the bilateral straight-line mechanism 8BSLM for coordination of the mated flexion/extension of radiolucent members 8b which form said radiolucent hinge via "virtual rack" computer coordination with the real-time elevation of the BSLM 1002cr. the said real-time elevation data may be acquired via analog measurement in concert with optical tracking, or via mounted fiducials tracked via optical or laser tracking, such that BSLM 1002cr may perfectly emulate function of the racked iterations. The constituent components of circular rotating rack iteration 1002 include: housing 1002A for BSLM for circular rack 1002CR, BSLM 1002CR of circular rotating rack iteration 1002. 1002B is an expandable/collapsible sheath for upper and lower scissor lifts.

The BSLM functionality achieves bilateral straight-line functionality via the conversion of the rotation of the differential planetary gear 8D into the coordinated oscillating linear motion of slotted scotch yoked radiolucent laminar members 8B for purposes of the continuously mated flexion/extension of the radiolucent flexion/extension hinge joint configured as a radiolucent, imaging compatible flexion/extension patient platform. Simply stated, a $\frac{1}{5}^{th}$ rotation or 72 degrees total rotation of the annulus/ring 8D3 of the differential planetary gear 8D results in a $\frac{4}{5}^{th}$'s rotation or 288 degrees of total rotation of the sun gear 8D1 (and an equivalent rotation of the crank 8C) in the opposite direction of the rotation of the annulus/ring 8D3, Thereby resulting in the automatic and simultaneous elongation or retraction of the yoked first and second laminar/planar members 8B (the members form the radiolucent hinge) to exactly compensate for the naturally widening or naturally diminishing gap which would normally separate the first and second arms from one another in direct proportion to their departure from and return to a horizontal orientation(i.e. straight line functionality). This automatic and simultaneous compensation in both angulation and length is accomplished via the conversion of the rotation/angulation of the planetary annulus/ring 8D3 of the planetary differential gear 8D into the oscillating linear motion of the slotted scotch yoke 8B across the full continuum of the 72 degrees of rotation.

In the fixed rotational center mode, the fixed pivot point around which the mated flexion/extension of the radiolucent laminar members 8B rotate is at central pivot point 0, with the planetary gears 8D translating vertically along laterally positioned vertical straight lines 00.

In the vertically rising/descending rotational center mode of usage of the bilateral straight line mechanism 8B SLM, it is the lateral pivot point(s) at both sides of horizontal line 0000 around which lateral yoked radiolucent laminar members 8B rotate, thereby enabling the mated flexion/extension point of the radiolucent laminar members 8B to elevate and descend vertically along medial vertical straight line 000, located at the midline bisecting the distance between lateral straight lines 00 and 00.

The "precession" of the planets 8D2 and planet carrier 8D4 is an integral function within the rotating differential planetary 8D of the BSLM 8 as it converts rotation into linear reciprocation of the slotted scotch yoked radiolucent laminar member 8B. differential planetary gear 8D, is a Specialized planetary gear with no stationary elements, necessitating that in addition to the annulus/ring 8D3 and the sun gear 8D1 rotating freely, that the planets 8D2 and planet carrier 8D4 are also enabled to orbit the sun in the same direction as the travel of the annulus/ring 8D3 (as opposed to remaining Stationary) with the resulting "precession" of these planets 8D4 (precession defined as the slow and continuous change in the rotation, such as movement around a fixed point of a planet, star, etc. that is spinning around another planet, star, etc.) serving as an integral element enabling continuous bilateral straight line functionality across the entire seventy two degree range of angulation 72 as originally visualized and conceptualized. This "precession" of the planets 8D2 as they synchronistically orbit in the same direction as the rotation of the outer annulus/ring 8D3, (albeit at a differing orbital speed), with the concomitant counter—rotation of sun gear 8D1 and crank 8c, thereby enables the coordinated conversion of planetary rotation into the linear reciprocation of yoked radiolucent laminar members 8B, VIA the circumferential travel of coupling pin 8C1 within slot 8B.S of radiolucent laminar member 8B, all of said performed automatically, incrementally and in sync with each degree by degree rotation of the differential planetary gear 8D across the full continuum of the seventy-two degrees of angulation 72 as per the design of the bilateral straight line mechanism 8BSLM.

One oscillation cycle equaling a $\frac{1}{5}^{th}$ rotation, or a 24 toothed movement of the 120 toothed annulus/ring 8D1, through the full 72 degrees of rotation available to the differential planetary gear 8D, defined as one entire reciprocation of the slotted yoke/radiolucent laminar member 8B, to include full extension from the rotational housing 8A, full retraction into the rotational housing 8A, and then full extension again from the rotational housing 8A with continuous incremental reciprocation of slotted yoke/radiolucent laminar member 8B occurring as the differential planetary gear 8D rotates degree by degree through the full seventy-two degrees of available rotation or one full oscillation cycle, via a $\frac{1}{5}^{th}$ revolution of the planetary annulus/ring gear, equaling a 24 tooth rotation of 120 toothed annulus ring 8D3, and a resulting 12 tooth, $\frac{4}{5}^{th}$s counter-rotation of 15 toothed sun gear 8D1, with straight line mechanism functionality thereby enabled to occur continuously, automatically, and incrementally, degree by degree, across the full continuum of the seventy-two degrees of available rotation of the planetary differential gear 8D, and the corresponding seventy-two degrees of available angulation of radiolucent laminar members 8B. In the current implementation seventy-two degrees of angulation is used. It is preferred to have at least seventy-degrees of angulation in order to achieve the different patient positions.

It is to be noted that straight line functionality of the mechanism ceases when rotation exceeds the seventy-two degrees of available rotation for the following reason; at 36 degrees of elevation from the horizontal, and correspondingly at 36 degrees of declination from the horizontal, the rotation of the crank 8C and pin 8C1 have achieved their full extension, advancing the length of one planetary gear diameter PGD, with pin 8C1 and crank 8C oriented to point exactly towards the mating point of the radiolucent laminar members 8B (that form the Radiolucent Hinge as described in patent Ser. No. 13/251,985, that is incorporated reference herein), at which point no further coordinated mechanical advancement is possible, as further rotation beyond this point would cross a secondary moment of transition whereby any further rotation would merely result in retraction of the radiolucent laminar member 8D as opposed to further advancement of the radiolucent laminar member 8B, thereby ceasing all straight line functionality of the mechanism. The above holds for both the vertically rising/descending rotational center & the fixed rotational center modalities of usage.

Of note, it is at the 0 degree horizontal orientation that outer gear 8ER is enabled to transition at horizontal line 0000 from being in mesh with lower rack segment 1001DB to being in mesh with rising secondary rack segment 1001DA as it crosses the moment of equilibrium at horizontal line 0000 as the lower scissor-lift 1001G attains its maximum height at 0000 and the Bilateral straight line mechanism transitions from being in mesh with the lower rack segment 1001DB to being in mesh with the secondary rack segment 1001DA. This is accomplished via the usage of outer gear 8ER having been configured with parallel gear teeth which enable the transfer of being "in mesh" with the lower rack segment to being "in mesh" with secondary rack segment, as the moment of equilibrium is crossed.

The partition/separation and re-attachment function of radiolucent, imaging compatible, flexion/extension spine table iterations 1000, 1000, & 1002 is necessitated by the closed torus of the c.t. imaging bore; whereas the o-arm imaging bore 29, and C-ARM imaging bore 31, and open Mill imaging bore 32, Compatible, flexion/extension spine iterations all feature an opening in the imaging bores which can be maneuvered around radiolucent, imaging 1000, 1000, & 1002. C.T. imaging bore 30 is a closed torus, and therefore unable to be utilized with the radiolucent flexion table 1002.

Therefore, for purposes of allowing the usage of radiolucent, imaging compatible, flexion/extension spine table iterations 1000, 1000, & 1002 within closed torus imaging bores such as the C.T. imaging bore 30, iterations 1000, 1000, & 1002 are enabled to partition at the flexion/extension point of radiolucent hinge joint, via usage of radiolucent removable non-metallic pin, pivot connection points 4C, 5C or 6C with radiolucent non-metallic detent clevis pin(s) 4C1, 5C1, or 6C1, for securing removable non-metallic pin, pivot connection points. This partition and re-attachment function thereby enabling insertion of the closed torus imaging bore/C.T. imaging bore 30 into the resultant gap formed by the resultant partition of the radiolucent hinge as patient platform, with re-attachment of the flexion/extension point of the radiolucent hinge joint when configured as a radiolucent anatomic patient positioning platform, within the closed torus imaging bore (C.T. imaging bore 30), thereby allowing usage of radiolucent, imaging compatible, flexion/extension spine table iterations 1000, 1000, & 1002 within closed torus—style imaging bores.

It will be understood and is appreciated by persons skilled in the art, that one or more processes, sub-processes, or process steps described in connection with the figures may be performed by hardware and/or software (machine-readable instructions). If the approach is performed by software, the software may reside in software memory in a suitable electronic processing component or system such as one or more of the functional components or modules schematically depicted in the figures.

The software in software memory of the controller 36 may include an ordered listing of executable instructions for implementing logical functions (that is, "logic" that may be implemented either in digital form such as digital circuitry or source code or in analog form such as analog circuitry or an analog source such an analog electrical, sound or video signal), and may selectively be embodied in any computer-readable medium for use by or in connection with an instruction execution system, apparatus, or device, such as a computer-based system, processor containing system, or other systems that may selectively fetch the instructions from the instruction execution system, apparatus, or device and execute the instructions. In the context of this disclosure, a "computer-readable medium" is any tangible means that may contain or store the program for use by or in connection with the instruction execution system, apparatus, or device. The tangible computer-readable medium may selectively be, for example, but is not limited to, an electronic, magnetic, optical, electromagnetic, or semiconductor system, apparatus or device. More specific examples, but a non-exhaustive list, of tangible computer-readable media, would include the following: a portable computer diskette (magnetic), a RAM (electronic), a read-only memory "ROM" (electronic), an erasable programmable read-only memory (EPROM or Flash memory) (electronic) and a portable compact disc read-only memory "CDROM" (optical). Note that the tangible computer-readable medium may even be paper (punch cards or punch tape) or another suitable medium upon which the instructions may be electronically captured, then compiled, interpreted or otherwise processed in a suitable manner if necessary, and stored in computer memory.

The foregoing detailed description of one or more embodiments of the approach for controlling a patient platform has been presented herein by way of example only and not limitation. It will be recognized that there are advantages to certain individual features and functions described herein that may be obtained without incorporating other features and functions described herein. Moreover, it will be recognized that various alternatives, modifications, variations, or improvements of the above-disclosed embodiments and other features and functions, or alternatives thereof, may be desirably combined into many other different embodiments, systems or applications. Presently unforeseen or unanticipated alternatives, modifications, variations, or improvements therein may be subsequently made by those skilled in the art which are also intended to be encompassed by the appended claims. Therefore, the spirit and scope of any appended claims should not be limited to the description of the embodiments contained herein.

What is claimed is:

1. A patient platform, comprising:
   a first planetary gear contained in a housing with a first scotch yoke;
   a second planetary gear contained in a housing with a second scotch yoke; and
   a first radiolucent laminar member coupled to the first scotch yoke and a second radiolucent laminar member coupled to the second scotch yoke, wherein the first radiolucent laminar member is coupled to the second radiolucent member and the first radiolucent laminar member and the second radiolucent laminar member support a patient platform.

2. The patient platform of claim 1, wherein the first radiolucent laminar member is coupled to the second radiolucent laminar member with a radiolucent connector.

3. The patient platform of claim 2, wherein the radiolucent connector is a removable radiolucent connector.

4. The patient platform of claim 1, wherein the first laminar member has a buttress on at least one side.

5. The patient platform of claim 1 wherein the first scotch yoke has a total range of vertical rotation of a maximum of seventy-two degrees.

6. The patient platform of claim 5 where the second scotch yoke has the same range of vertical rotation as the first scotch yoke.

7. The patient platform of claim 1, further comprising a first support that allows movement of the first scotch yoke vertically, and
   a second support that allows movement of the second scotch yoke vertically.

8. The patient platform of claim 1, where the first radiolucent laminar member and the second radiolucent laminar member have fiducial markers.

9. The patient platform of claim 1, where the first radiolucent laminar member and the second laminar member are set into each other.

10. A patient platform method for support of a patient, including:
    supporting a first planetary gear contained in a housing with a first scotch yoke;
    supporting a second planetary gear contained in a housing with a second scotch yoke; and
    coupling a first radiolucent laminar member attached to the first scotch yoke with a second radiolucent laminar member attached to the second scotch yoke, with a radiolucent connector.

11. The patient platform method of claim 10, wherein the radiolucent connector is a removable radiolucent connector.

12. The patient platform method of claim 10, includes buttressing the first laminar member with a buttress on at least one side of the first laminar member.

13. The patient platform method of claim 10, includes vertically rotating the first scotch yoke at a maximum of seventy-two degrees.

14. The patient platform method of claim 13 where the second scotch yoke has the same range of vertical rotation as the first scotch yoke.

15. The patient platform method of claim 10, further includes supporting with a first support the first scotch yoke and allowing movement vertically, and
    supporting with a second support that allows movement of the second scotch yoke vertically.

16. The patient platform method of claim 10, includes marking the first radiolucent laminar member and the second radiolucent laminar member with fiducial markers.

17. The patient platform method of claim 10, includes setting into the first radiolucent laminar member the second radiolucent laminar member.

* * * * *